(12) United States Patent
Ebbini et al.

(10) Patent No.: US 11,547,384 B2
(45) Date of Patent: Jan. 10, 2023

(54) VASCULAR CHARACTERIZATION USING ULTRASOUND IMAGING

(71) Applicant: REGENTS OF THE UNIVERSITY OF MINNESOTA, Minneapolis, MN (US)

(72) Inventors: Emad S. Ebbini, Edina, MN (US); Dalong Liu, Issaquah, WA (US); Yayun Wan, Bothell, WA (US); Andrew J. Casper, Eau Claire, WI (US)

(73) Assignee: Regents of the University of Minnesota, Minneapolis, MN (US)

( * ) Notice: Subject to any disclaimer, the term of this patent is extended or adjusted under 35 U.S.C. 154(b) by 1290 days.

(21) Appl. No.: 15/475,739

(22) Filed: Mar. 31, 2017

(65) Prior Publication Data

US 2017/0296140 A1    Oct. 19, 2017

Related U.S. Application Data

(62) Division of application No. 13/446,635, filed on Apr. 13, 2012, now Pat. No. 9,610,061.
(Continued)

(51) Int. Cl.
*A61B 8/08* (2006.01)
*A61B 8/06* (2006.01)

(52) U.S. Cl.
CPC .............. *A61B 8/0891* (2013.01); *A61B 8/06* (2013.01); *A61B 8/085* (2013.01); *A61B 8/485* (2013.01); *A61B 8/486* (2013.01)

(58) Field of Classification Search
CPC .. A61B 2019/5276; A61B 2018/00404; A61B 8/485; A61B 5/489; A61B 8/0891; A61B 5/026
See application file for complete search history.

(56) References Cited

U.S. PATENT DOCUMENTS 5,694,936 A    12/1997  Fujimoto
5,906,580 A    5/1999   Kline-Schoder
(Continued)

FOREIGN PATENT DOCUMENTS

CN    1001179998 A    5/2008
CN    102788836 A     11/2012
(Continued)

OTHER PUBLICATIONS

Ebbini, Emad S. "Phase-coupled two-dimensional speckle tracking algorithm." IEEE transactions on ultrasonics, ferroelectrics, and frequency control 53.5 (2006): 972-990 (Year: 2006).*
(Continued)

*Primary Examiner* — Sean D Mattson
(74) *Attorney, Agent, or Firm* — Mueting Raasch Group

(57) ABSTRACT

Ultrasound methods provide for the motion tracking of both vessel wall motion and blood flow (e.g., with use of high frame rate ultrasound pulse echo data and speckle tracking both wall motion and flow can be tracked simultaneously). Ultrasound systems provide for the motion tracking of both vessel wall motion and blood flow (e.g., with use of high frame rate ultrasound pulse echo data and speckle tracking both wall motion and flow can be tracked simultaneously).

24 Claims, 19 Drawing Sheets
(13 of 19 Drawing Sheet(s) Filed in Color)

Related U.S. Application Data

(60) Provisional application No. 61/475,550, filed on Apr. 14, 2011.

(56) References Cited

U.S. PATENT DOCUMENTS

| | | | |
|---|---|---|---|
| 6,172,939 B1 | 1/2001 | Cole | |
| 6,277,075 B1 | 8/2001 | Torp | |
| 6,318,179 B1 * | 11/2001 | Hamilton | A61B 8/06 |
| | | | 600/454 |
| 6,492,762 B1 | 12/2002 | Pant | |
| 6,494,839 B1 | 12/2002 | Averkiou | |
| 6,540,677 B1 | 4/2003 | Angelsen | |
| 6,618,493 B1 | 9/2003 | Torp | |
| 6,705,993 B2 | 3/2004 | Ebbini | |
| 6,770,031 B2 | 8/2004 | Hynynen et al. | |
| 6,951,540 B2 | 10/2005 | Ebbini et al. | |
| 7,063,666 B2 | 6/2006 | Weng et al. | |
| 7,686,764 B2 | 3/2010 | Watanabe et al. | |
| 7,901,358 B2 | 3/2011 | Mehi | |
| 8,002,705 B1 | 8/2011 | Napolitano | |
| 8,086,296 B2 | 12/2011 | Bystritsky | |
| 8,591,419 B2 | 11/2013 | Tyler | |
| 8,911,372 B2 | 12/2014 | Yoshikawa et al. | |
| 8,939,909 B2 | 1/2015 | Wegner | |
| 9,144,693 B2 | 9/2015 | Appelman | |
| 9,592,409 B2 | 3/2017 | Yoo | |
| 9,610,061 B2 | 4/2017 | Ebbini et al. | |
| 10,231,712 B2 | 3/2019 | Ebbini et al. | |
| 2001/0017937 A1 | 8/2001 | Bonnefous | |
| 2001/0029336 A1 | 10/2001 | Teo | |
| 2001/0039381 A1 | 11/2001 | Burns | |
| 2003/0000367 A1 | 2/2003 | Davidsen | |
| 2003/0097068 A1 | 5/2003 | Hossack | |
| 2003/0220636 A1 | 11/2003 | Bowman | |
| 2003/0225331 A1 | 12/2003 | Diederich | |
| 2004/0015079 A1 | 1/2004 | Berger | |
| 2004/0106880 A1 | 6/2004 | Weng | |
| 2004/0210135 A1 | 10/2004 | Hynynen | |
| 2005/0070796 A1 | 3/2005 | Tsujita | |
| 2005/0102009 A1 | 5/2005 | Costantino | |
| 2005/0249667 A1 | 11/2005 | Tuszynski | |
| 2005/0267453 A1 | 12/2005 | Wong et al. | |
| 2007/0016040 A1 | 1/2007 | Nita | |
| 2007/0038100 A1 | 2/2007 | Nita | |
| 2007/0055155 A1 | 3/2007 | Owen | |
| 2007/0129633 A1 | 6/2007 | Lee et al. | |
| 2008/0015440 A1 * | 1/2008 | Shandas | G06T 7/20 |
| | | | 600/458 |
| 2008/0027320 A1 | 1/2008 | Bolorforosh | |
| 2008/0045882 A1 | 2/2008 | Finsterwald | |
| 2008/0221448 A1 | 9/2008 | Khuri-Yakub et al. | |
| 2008/0228075 A1 | 9/2008 | Fraser | |
| 2009/0048546 A1 | 2/2009 | Appelman et al. | |
| 2009/0069677 A1 | 3/2009 | Chen | |
| 2009/0069680 A1 | 3/2009 | Yasuhiko | |
| 2009/0160309 A1 | 6/2009 | Burth | |
| 2010/0004540 A1 | 1/2010 | Thiele | |
| 2010/0286520 A1 | 11/2010 | Hazard | |
| 2011/0112405 A1 | 5/2011 | Barthe | |
| 2011/0248714 A1 | 10/2011 | Salomir | |
| 2012/0053391 A1 | 3/2012 | Mishelevich | |
| 2012/0083692 A1 | 4/2012 | Stoll et al. | |
| 2012/0283502 A1 | 8/2012 | Mishelevich | |
| 2012/0283564 A1 | 11/2012 | Ebbini | |
| 2012/0289869 A1 | 11/2012 | Tyler | |
| 2013/0123635 A1 | 5/2013 | Wegner | |
| 2013/0144165 A1 | 6/2013 | Ebbini et al. | |
| 2013/0001973 A1 | 8/2013 | Jin | |
| 2014/0343463 A1 | 11/2014 | Mishelevich | |
| 2015/0251025 A1 | 9/2015 | You | |
| 2016/0143617 A1 | 5/2016 | Ebbini et al. | |
| 2017/0080255 A1 | 3/2017 | Law | |
| 2017/0224990 A1 | 8/2017 | Goldwasser | |
| 2019/0269385 A1 | 9/2019 | Ebbini et al. | |
| 2019/0308036 A1 | 10/2019 | Ebbini | |
| 2020/0121960 A1 | 4/2020 | Darrow et al. | |

FOREIGN PATENT DOCUMENTS

| | | |
|---|---|---|
| CN | 102800071 A | 11/2012 |
| EP | 0392743 | 10/1990 |
| EP | 2310094 | 10/2014 |
| WF | WO 2009/050719 | 4/2009 |
| WO | WO 2006/018761 | 2/2006 |
| WO | WO 2006/042201 A1 | 4/2006 |
| WO | WO 2006/090298 A1 | 8/2006 |
| WO | WO 2008/053457 A2 | 5/2008 |
| WO | WO 2009/002492 | 12/2008 |
| WO | WO 2011/156624 A2 | 12/2011 |
| WO | 2012/033584 | 4/2012 |
| WO | WO 2012/142455 A2 | 10/2012 |
| WO | WO 2013/059833 | 4/2013 |
| WO | WO 2015/013196 | 1/2015 |

OTHER PUBLICATIONS

Trahey, Gregg E., John W. Allison, and Olaf T. Von Ramm. "Angle independent ultrasonic detection of blood flow." IEEE Transactions on Biomedical Engineering 12 (1987): 965-967. (Year: 1987).*

U.S. Appl. No. 61/353,096, filed Jun. 9, 2010, Ebbini et al.

U.S. Appl. No. 61/475,550, filed Apr. 14, 2011, Ebbini et al..

Ainsworth et al. "3D ultrasound measurement of change in carotid plaque volume—A tool for rapid evaluation of new therapies," 2005. *Stroke*. 36(9):1904-1909.

Amini et al., "Noninvasive Estimation of Tissue Temperature Via High-Resolution Spectral Analysis Techniques," *IEEE Transactions on Biomedical Engineering*, Feb. 2005; 52(2):221-228.

Arthur et al., "In vivo change in ultrasonic backscattered energy with temperature in motion-compensated images," *International Journal of Hyperthermia*, 2008; 24(5):389-398.

Aubry et al., "Transcostal high-intensity-focuses ultrasound: Ex vivo adaptive focusing feasibility study," *Phys. Med. Biol.*, 2008; 53:2937-2951.

Ballard et al. "Adaptive Transthoracic Refocusing of Dual-Mode Ultrasound Arrays," 2010. *IEEE Transactions on Biomedical Engineering*. 57(1):93-102.

Ballard et al., "Monitoring and Guidance of HIFU Beams with Dual-Mode Ultrasound Arrays," *31st Annual International Conference of the IEEE EMBS*, Minneapolis, MN; Sep. 2-6, 2009:137-140.

Bischof et al. "Rectal Protection During Prostate Cryosurgery: Design and Characterization of an Insulating Probe," *Cryobiology* 1997; 34:80-92.

Blake et al. "A Method to estimate wall shear rate with a clinical ultrasound scanner," 2008. *Ultrasound in Medicine and Biology*. 34(5):760-774.

Blana et al., "First analysis of the long-term results with transrectal HIFU in patients with localized prostate cancer," *Euro Urology*, Jun. 2008; 53(6):1194-1203.

Bohn et al., "An analysis package comparing pid antiwindup strategies," *Control Systems Magazine, IEEE*, Apr. 1995; 15(2):34-40.

Botros et al., "Two-step hybrid virtual array-ray (VAR) technique for focusing through the rib cage," *IEEE Trans. Ultrason. Ferroelectr., Freq. Control*, Jul. 1998; 45(4): 989-1000.

Bracewell et al. "Two-dimensional Imaging". Printice-Hall Signal Processing Series. 1995. Cover page, Title Page, Copyright Page, and Table of Contents. 11 pages total.

Casper et al., "Realtime Control of Multiple-focus Phased Array Heating Patterns Based on Noninvasive Ultrasound Thermography," *IEEE Trans. Biomed. Eng.*, Jan. 2012; 59(1):95-105.

Cespedes et al. "Echo decorrelation from displacement gradients in elasticity and velocity estimation" 1999. *IEEE Trans. UFFC*. 46:791-801.

Chan et al., "An image-guided high intensity focused ultrasound device for uterine fibroids treatment," *Med. Phys.*, 2002; 29:2611-2620.

(56) References Cited

OTHER PUBLICATIONS

Chapelon et al., "New piezoelectric transducers for therapeutic ultrasound," *Ultrasound Med. Biol.*, Jan. 2000; 26(1):153-159.
Chew et al. "Waves and Fields in Inhomogeneous Media". 1990. Van Nostrand Reinhold, New York, NY. Cover Page, Title Page, Copyright Page, and Table of Contents. 12 pages total.
Curiel et al., "1.5-D high intensity focused ultrasound array for non-invasive prostate cancer surgery," *IEEE Trans. Ultrason., Ferroelectr., Freq. Control*, Feb. 2002; 49(2):231-242.
Dalong et al., "Viscoelastic property measurement in thin tissue constructs using ultrasound," *IEEE Trans. Ultrason. Ferroelecdt. Freq. Contr.*, 2008; 55(2):368-383.
Ebbini. "Phase-coupled two-dimensional speckle tracking algorithm," 2006. *IEEE Trans. Ultrason. Ferroelect. Freq. Contr.*, 53(5):972-990.
Ebbini et al. "Dual-Mode Ultrasound Phased Arrays for Image-Guided Surgery," 2006. *Ultrasound Imaging*. 28:65-82.
Ebbini et al., "A cylindrical-section ultrasound phased-array applicator for hyperthermia cancer therapy," *IEEE Trans. Ultrasonics, Ferroelectrics, and Frequency Control*, 1988; 35(5): 561-572.
Ebbini et al., "Multiple-focus ultrasound phased array pattern synthesis—Optimal driving signal distributions for hyperthermia," *IEEE Transactions on Ultrasonics Ferroelectrics and Frequency Control*, Sep. 1989; 36(5): 540-548.
Ebbini, "Deep-localized hyperthermia with ultrasound phased arrays using the pseudoinverse pattern synthesis methods," Ph.D. Dissertation, University of Illinois, Urbana, IL; 1990.
Ebbini et al., "Experimental evaluation of a prototype cylindrical section ultrasound hyperthermia phased-array applicator," *IEEE Transactions on Ultrasonics Ferroelectrics and Frequency Control*, Sep. 1991; 38(5):510-520.
Ebbini et al., "Optimization of the intensity gain of multiple-focus phased-array heating patterns," *Int. J. Hyperthermia*, 1991; 7(6): 953-973.
Ebbini et al., "A spherical-section ultrasound phased array applicator for deep localized hyperthermia," *IEEE Trans. Biomedical Engineering*, 1991; 38(7):634-643.
Ebbini et al., "Optimal transversal filter bank for 3D real-time acoustical imaging," *Proc. 26th Annual Asilomar Conference on Signals, Systems and Computers*, 1992; 2:831-835.
Ebbini et al., "Lesion formation and visualization using dual-mode ultrasound phased arrays," *Proc. IEEE Ultrason. Symp.*, Oct. 2001; 2:1351-1354.
Ebbini et al., "Monitoring and Guidance of Minimally-Invasive Thermal Therapy Using Diagnostic Ultrasound," *31st Annual International Conference of the IEEE EMBS*, Minneapolis, MN; Sep. 2-6, 2009:4283-4286.
Ebbini, "Guest Editorial to the Special Issue on Therapeutic Ultrasound: Current Status and Future Directions," *IEEE Transactions on Biomedical Engineering*, Jan. 2010; 57(1):57-60.
Ebbini, "Guest Editorial to the Special Issue on Therapeutic Ultrasound: Trends at the Leading-Edge," *IEEE Transactions on Biomedical Engineering*, Jan. 2010; 57(1):5-6.
Ebbini et al., "Dereverberation of Ultrasound Echo Data in Vascular Imaging Applications," IEEE International Conference on Acoustics, Speech and Signal Processing (ICASSP), May 22-27, 2011:741-744.
Figueroa et al. "A computational framework for fluid-solid-growth modeling in cardiovascular simulations," 2009. *Computer Methods in Applied Mechanics and Engineering*. 198(45-46):3583-3602.
Fink, "Time reversal of ultrasonic fields. I. Basic principles," *IEEE Trans. Ultrason., Ferroelectr., Freq. Control*, Sep. 1992; 39(5):555-566.
Fleury et al., "New piezocomposite transducers capable of producing high-power levels suitable for therapy with reasonably wide bandwidth suitable for imaging," *Proc. 2nd Int. Symp. Ther. Ultrasound*, 2002; 1:428-436.
Fung et al. Biomechanics: Circulation, 2nd Ed. Springer, New York. 1997. Cover Page, Copyright Page, Table of Contents.

Goel et al., "Adjuvant Approaches to Enhance Cryosurgery," *Journal of Biomechanical Engineering*, 2009; 131(7):074003.
Gronningsaeter et al., "Vessel wall detection and blood noise reduction in intravascular ultrasound imaging," *IEEE Transactions on Ultrasonics, Ferroelectrics and Frequency Control*, IEEE, US, May 1, 1996; 43(3): pp. 359-369.
Haddadin et al. "Imaging strongly scattering media using a multiple frequency distorted Born iterative method". 1998. *IEEE Transactions of Ultrasonics Ferroelectrics and Frequency Control*. 45(6):1485-1496.
Haken et al., "Effect of mode conversion on ultrasonic heating oat tissue interfaces," *J. Ultrasound Med.*, 1992; 11:393-405.
Hermus et al. "Advanced carotid plaque imaging". 2010. *European Journ. of Vascular and Endovascular Surgery*. 39(2):125-133.
Hindley et al., "MRI guidance of focused ultrasound therapy of uterine fibroids: Early results," *Am. J. Roentgenology*, Dec. 2004; 183(6):1713-1719.
Hynynen et al., "Trans-skull ultrasound therapy: The feasibility of using image-derived skull thickness information to correct the phase distortion," *IEEE Trans. Ultrason, Ferroelectr., Freq. Control*, May 1999; 46(5): 752-755.
Ibbini et al., "N X N square-element ultrasound phased array applicator: Simulated temperature distributions associated with directly synthesized heating patterns," *IEEE Trans. Ultrason, Ferroelectr., Freq. Control*, 1990; 37(6):491-500.
Insana et al. "Maximum-likelihood approach to strain imaging using ultrasound". 2000. *J. Acoust. Soc. Am.* 107(3):1421-1434.
International Search Report dated Jun. 13, 2013 in the Netherlands, for Patent Application No. PCT/US2012/033584, filed Apr. 13, 2012.
International Preliminary Report on Patentability and Written Opinion dated Dec. 10, 2012, for International Application No. PCT/US2011/039837, filed Jun. 9, 2011; 6 pgs.
International Preliminary Report on Patentability and Written Opinion dated Oct. 15, 2013, for International Application No. PCT/US2012/033584, filed Apr. 13, 2012; 12 pgs.
International Search Report dated Jan. 20, 2012, for International Application No. PCT/US2011/039837, filed Jun. 9, 2011; 4 pgs.
Ishida et al., "Development and animal experiment of variable focusing HIFU system for prostate cancer treatment," *3rd Int. Symp. THer. Ultrasound*, 2003; 1:382-387.
Karimi et al. "Estimation of Nonlinear Mechanical Properties of Vascular Tissues via Elastography," 2008. *Cardiovascular Engineering*. 8(4):191-202.
Kim et al. "Arterial vulnerable plaque characterization using ultrasound-induced thermal strain imaging (TSI)," 2008. *IEEE Transaction on Biomedical engineering*. 55(1):171-180.
Lee et al., "High Intensity Focused Ultrasound Effect on Cardiac Tissues: Potential for Clinical Application," *Echocardiography*, 2000; 17(6):563-566.
Li et al., "A new filter design technique for coded excitation systems," *IEEE Trans. Ultrasonics, Ferroelectrics, and Frequency Control*, 1992; 3 9(6):693-699.
Li et al., "Blocked Element Compensations in Phased Array Imaging," *IEEE Trans. Ultrasonics, Ferroelectrics, and Frequency Control*, 1993; 40(4):283-292.
Liu et al. "Real-Time 2-D Temperature Imaging Using Ultrasound," 2010. *IEEE Transactions on Biomedical Engineering*. 57(1):12-16.
Liu et al. "Viscoelastic property measurement in thin tissue constructs using ultrasound". 2008. *IEEE Trans. Ultrason. Ferroelect. Freq. Contr.* 55(2):368-383.
Lubinski et al. "Speckle tracking methods for ultrasonic elasticity imaging using short-time correlation". *1999. IEEE Trans. UFFC.* 46:82-96.
Maass-Moreno et al., "Noninvasive temperature estimation in tissue via ultrasound echo shifts. Part I. Theoretical model," *The Journal of the Acoustical Society of America*, 1996; 100(2514-2521).
Mahmoud et al. "In vivo vascular wall tissue characterization using a strain tensor measuring (STM) technique for flow-mediated vasodilation analyses". 2009. *Physics in Medicine and Biology*. 54(20):6217-6238.

(56) References Cited

OTHER PUBLICATIONS

Martin et al., "Investigation of HIFU produced emulsion for acoustic hemostasis," *Proc. 3rd Int. Symp. Ther. Ultrasound*, 2003; 1:351-356.

McGough et al., "Direct Computation of ultrasound phased-array driving signals from specified temperature distribution for hyperthermia," *IEEE Trans. Biomedical Engineering*, 1992; 39(8):825-835.

McGough et al., "Mode scanning: heating pattern synthesis with ultrasound phased arrays," *Int. Journal of Hyperthermia*, 1994; 10(3):433-442.

Miller et al., "Fundamental limitations of noninvasive temperature imaging by means of ultrasound echo strain estimation," *Ultrasound in Medicine and Biology*, 2002; 28:1319-1333.

Mougenot et al., "Automatic spatial and temporal temperature control for MR-guided focused ultrasound using fast 3D MR thermometry and multispiral trajectory of the focal point," *Magnetic Resonance in Medicine*, Nov. 2004; 52(5):1005-1015.

Mougenot et al., "Three-dimensional spatial and temporal temperature control with MR thermometry-guided focused ultrasound (mrghifu)," *Magnetic Resonance in Medicine*, 2009; 61:603-614.

Moyle et al. "Inlet conditions for image-based CFD models of the Carotid bifurcation: Is it reasonable to assume fully developed flow?" 2006. *Journ. of Biomechanical Engr. Transactions of the ASME*. 128(3):371-379.

Nightingale et al., "On the feasibility of remote palpation using acoustic radiation force," *J. Acoust. Soc. Amer.*, Jul. 2001; 110:625-634.

Pernot et al., "High power density prototype for high precision transcranial therapy," *Proc. 3rd Int. Symp. Ther. Ultrasound*, 2003; 1:405-410.

Pernot et al., "Temperature estimation using ultrasonic spatial compounding," *IEEE Trans. Ultrason., Ferroelect., Freq. Contr.*, 2004; 51(5):606-615.

Pesavento et al. "A time efficient and accurate strain estimation concept for ultrasonic elastography using iterative phase zero estimation". 1999. *IEEE Trans. UFFC*. 46(5): 1057-1067.

Poissonnier et al., "Control of prostate cancer by transrectal HIFU in 227 patients," *Eur. Urol.*, 2007; 51:381-387.

Prada et al., "The iterative time reversal process: Analysis of the convergence," *J. Acoust. Soc. Amer.*, 1995; 95:62-71.

Pramanik et al., "Thermoacoustic and photoacoustic sensing of temperature," *Journal of Biomedical Optics*, 2009; 14(5).

Rabben et al. "Ultrasound-based vessel wall tracking: An auto-correlation technique with RF center frequency estimation". 2002. *Ultrasound in Medicine and Biology*. 28(4):507-517.

Rabben et al. "An ultrasound-based method for determining pulse wave velocity in superficial arteries". 2004. *Journ. Of Biomechanics* . 37(10):1615-1622.

Raghupathy et al. "Generalized Anisotropic Inverse Mechanics for Soft Tissues". 2010. *J. Biomech. Eng*. 132. Accepted 2010.

Revell et al., "Ultrasound Speckle Tracking For Strain Estimation," University of Bristol Department of Computer Science; Dec. 2003: 4pgs.

Ribbers et al. "Noninvasive two-dimensional strain imaging of arteries: Validation in phantoms and preliminary experience in carotid arteries in vivo". 2007. *Ultrasound in Medicine and Biology*. 33(4):530-540.

Salomir et al., "Hyperthermia by MR-guided focuses ultrasound: Accurate temperature control based on fast MRI and a physical model of local energy deposition and heat conduction," *Magnetic Resonance in Medicine*, 2000; 43:342-347.

Sanghvi et al., "Noninvasive surgery of prostate tissue by high-intensity focused ultrasound," *IEEE Trans. Ultrason., Ferroelectr., Freq. Contr.*, Nov. 1996; 43(6):1099-1110.

Sanghvi et al., "New developments in therapeutic ultrasound," *IEEE Eng. Med. Biol. Mag.*, Nov./Dec. 1996; 15(6):83-92.

Sapareto et al., "Thermal dose determination in cancer therapy," *Int. J. Rad. Onc. Biol. Phys.*, 1984; 10(6):787-800.

Schoenhagen et al. "Coronary imaging: Angiography shows the stenosis, but IVUS, CT, and MRI show the plaque". 2003. *Cleveland Clinic Journ. Of Medicine*. 70(8):713-719.

Seip et al., "Characterization of a Needle Hydrophone Array for Acoustic Feedback during Ultrasound Hyperthermia Treatments," *Ultrasonics Symposium Proceedings*, 1992; 2:1265-1269.

Seip et al., "Non-Invasive Detection of Thermal Effects due to Highly Focused Ultrasonic Fields," *Ultrasonics Symposium Proceedings*, 1993; 2:1229-1232.

Seip et al., "Dynamic focusing in ultrasound hyperthermia treatments using implantable hydrophone arrays," *IEEE Trans. Ultrason., Ferroelectr., Freq. Control*, Sep. 1994; 41(5):706-713.

Seip et al., "Invasive and Non-invasive Feedback for Ultrasound Phased Array Thermotherapy," *Ultrasonics Symposium Proceedings*, 1994; 3:1821-1824.

Seip et al., "Non-invasive Spatio-temporal Temperature Change Estimation Using Diagnostic Ultrasound," *Ultrasonics Symposium Proceedings*, 1995.

Seip et al., "Non-invasive estimation of tissue temperature response to heating fields using diagnostic ultrasound," *IEEE Trans. Biomed. Eng.*, 1995; 42(8):828-839.

Seip et al., "Noninvasive real-time multipoint temperature control for ultrasound phased array treatments," *IEEE Transactions on Ultrasonics Ferroelectrics and Frequency Control*, Nov. 1996; 43(6):1063-1073.

Seip et al., "High-intensity focused ultrasound (HIFU) phased arrays: Recent developments in transrectal transducers and driving electronics," *Proc. 3rd Int. Symp. Ther. Ultrasound*, 2003; 1:423-428.

Shen et al., "An Optimal Image Operator Design Technique for Coded-Excitation Ultrasound Imaging System," *IEEE Ultrasonics Symposium Proceedings*, 1994.

Shen et al., "Post-Beamforming Processing Technique for Enhancing Conventional Pulse-Echo Ultrasound Imaging Contrast Resolution," *IEEE Ultrasonics Symposium Proceedings*, 1995.

Shen et al. "A New Coded-Excitation Ultrasound Imaging System—Part I: Basic Principles," 1996. *IEEE Transactions on Ultrasonics, Ferroelectrics, and Frequency Control*. 43(1):131-140.

Shen et al. "A New Coded-Excitation Ultrasound Imaging System—Part II: Operator Design," 1996. *IEEE Transactions on Ultrasonics, Ferroelectrics, and Frequency Control*. 43(1):141-148.

Shen et al. "Filter-Based Coded-Excitation System for High-Speed Ultrasonic Imaging," 1998. *IEEE Transactions on Medical Imaging*. 17(6):923-934.

Shung et al. "Scattering of ultrasound by blood". 1976. *IEEE Transactions on Biomedical Engineering*, vol. BME-23. 6:460-467.

Simon et al., "Estimation of Mean Scatterer Spacing Based on Autoregressive Spectral Analysis of Prefiltered Echo Data," *Ultrasonics Symposium Proceedings*, 1995.

Simon et al., "Combined ultrasound image guidance and therapy using a therapeutic phased array," *SPIE Med. Imag.*, May 1998; 3341:89-98.

Simon et al. "Two-Dimensional Temperature Estimation Using Diagnostic Ultrasound," 1998. *IEEE Transactions on Ultrasonics, Ferroelectrics, and Frequency Control*. 45(4):1088-1099.

Smith et al., "Control system for an MRI compatible intracavitary ultrasound array for thermal treatment of prostate disease," *International Journal of Hyperthermia*, May-Jun. 2001; 17(3):271-282.

Souchon et al., "Monitoring the formation of thermal lesions with heat-induces echo-strain imaging: a feasibility study," *Ultrasound in Medicine and Biology*, 2005; 31:251-259.

Steidl et al., "Dual-mode ultrasound phased arrays for noninvasive surgery: Postbeamforming image compounding algorithms for enhanced visualization of thermal lesions," *Proc. IEEE Int. Symp. Biomed. Imag.*, Jul. 2002; 429-432.

Steinman et al. "Flow imaging and computing: Large artery hemodynamics," 2005. *Annals of Biomedical Engineering*. 33(12):1704-1709.

Sumi, C. "Fine elasticity imaging utilizing the iterative rf-echo phase matching method". 1999. *IEEE Trans. UFFC*, 46(1):158-166.

Sun et al., "Focusing of therapeutic ultrasound through a human skull: A numerical study," *J. Acoust. Soc. Amer.*, 1998; 104:1705-1715.

(56) References Cited

OTHER PUBLICATIONS

Sun et al., "Adaptive real-time closed-loop temperature control for ultrasound hyperthermia using magnetic resonance thermometry," *Concepts in Magnetic Resonance Part B—Magnetic Resonance Engineering*, Oct. 2005; 27B(1):51-63.
Swillens et al. "Two dimensional flow imaging in the carotid bifurcation using a combined speckle tracking and phase-shift estimator: a study based on ultrasound simulations and in vivo analysis". 2010. *Ultrasound in Medicine and Biology*. 36(10):1722-1735.
Swillens et al. "Two-dimensional blood velocity estimation with ultrasound: speckle tracking versus crossed-beam vector Doppler based on flow simulations in a carotid bifurcation model". 2010. *IEEE Transactions on Ultrasonics Ferroelectrics and Frequency Control*. 57(2):327-339.
Tanter et al., "Focusing and steering through absorbing and aberrating layers: Application to ultrasonic propagation through the skull," *J. Acoust. SOc. Amer.*, 1998; 103:2403-2410.
Taylor et al. "Open problems in computational vascular biomechanics: Hemodynamics and arterial wall mechanics," 2009. *Computer Methods in Applied Mechanics and Engineering*. 198(45-46):3514-3523.
Tempany et al., "MR imaging-guided focuses ultrasound surgery of uterine leiomyomas: A feasibility study," *Radiology*, Nov. 2003;226:897-905.
Thomenius et al., "Evolution of ultrasound beamformers," *Proc. IEEE Ultrason. Symp.*, 1996; 1615-1622.
Trahey et al., "Angle independent ultrasonic blood flow detection by frame-to-frame correlation of B-mode images," *Ultrasonics*, IPC Science and Technology Press Ltd., Guildford, GB, Sep. 1, 1988; 26(5): pp. 271-276.
Tsou et al. "Role of ultrasonic shear rate estimation errors in assessing inflammatory response and vascular risk," 2008. *Ultrasound in Medicine and Biology*. 34(6):963-972.
Uchida et al., "Transrectal high-intensity focused ultrasound for the treatment of localized prostate cancer: Eightyear experience," *Int. J. Urology*, Nov. 2009; 16(11):881-886.
VanBaren et al., "A new algorithm for dynamic focusing of phased-array hyperthermia applicators through tissue inhomogeneities," *IEEE Ultrasonics Symposium Proceedings*, 1993; 2:1221-1224.
VanBaren et al., "Real-time Dynamic Focusing through Tissue Inhomogeneities during Hyperthermia Treatments with Phased Arrays," *Ultrasonics Symposium Proceedings*, 1994; 3:1815-1819.
VanBaren et al., "2D Large Aperture Ultrasound Phased Arrays for Hyperthermia Cancer Therapy: Design, Fabrication, and Experimental Results," *Ultrasonics Symposium Proceedings*, 1995.
VanBaren et al., "Multi-Point Temperature Control During Hyperthermia Treatments: Theory and Simulation," *IEEE Transactions on Biomedical Engineering*, Aug. 1995; 41(5):706-713.
Vanne et al., "MRI feedback temperature control for focused ultrasound surgery," *Physics in Medicine and Biology*, 2003; 48(1):31.
Varghese et al. "Direct strain estimation in elastography using spectral cross-correlation". 2000. *Ultrasound in Med. Biol.* 26(9):1525-1537.
Wan et al., "Ultrasound surgery: Comparison of strategies using phased array systems," *IEEE Trans. UFFC*, Nov. 1996; 43(6):1085-1098.
Wan et al. "Imaging with Concave Large-Aperture Therapeutic Ultrasound Arrays Using Conventional Synthetic-Aperture Beamforming" 2008. *IEEE Transactions on Ultrasound, Ferroelectrics, and Frequency Control*. 55(8):1705-1718.
Wan et al. "Imaging vascular mechanics using ultrasound: Phantom and in vivo results" Apr. 14-17, 2010, 7th IEEE International Symposium on Biomedical Imaging: From Nano to Macro, ISBI 2010, Rotterdam; Netherlands, Article No. 5490152, 980-983.
Wang et al., "Effects of phase quantization errors on field patterns generated by an ultrasound phased array hyperthermia applicator," *IEEE Trans. Ultrasonics Ferroelec. Frequency Control*, 1991; 38(5): 521-531.

Wang et al., "Adaptive 2-D Cylindrical Section Phased Array System for Ultrasonic Hyperthermia," *Ultrasonics Symposium Proceedings*, 1992; 2:1261-1264.
Wang et al., "Phase aberration correction and motion compensation for ultrasonic hyperthermia phased arrays: Experimental results," *IEEE Trans. on Ultrason., Ferroelec., and Freq. Control*, 1994; 41(1):34-43.
Weitzel et al. "High-Resolution Ultrasound Elasticity Imaging to Evaluate Dialysis Fistula Stenosis," 2009. *Seminars in Dialysis*. 22(1):84-89.
Written Opinion/International Preliminary Report on Patentability, dated Jul. 15, 2009, in Europe, Patent Application No. PCT/US2008/007842, filed Jun. 24, 2008.
Wu et al., "Time reversal of ultrasonic fields. II Experimental results," *IEEE Trans. Ultrason., Ferroelectr., Freq. Control*, Sep. 1992; 39(5):567-578.
Wu et al., "Advanced hepatocellular carcinoma: Treatment with high-intensity focused ultrasound ablation combined with transcatheter arterial embolization," *Radiology*, May 2005; 235(2):659-667.
Wu et al., "Feasibility of US-guided high-intensity focused ultrasound treatment in patients with advanced pancreatic cancer: Initial experience," *Radiology*, Sep. 2005; 236(3):1034-1040.
Yao et al., "Enhanced lesion visualization in image-guided noninvasive surgery with ultrasound phased arrays," *Proc. 23$^{rd}$ Annu. Int. Conf. IEEE Eng, Med. Biol. Soc.*, Oct. 2001; 3:2492-2495.
Yao et al., "Real-time monitoring of the transients of HIFU-induced lesions," *Proc. IEEE Ultrason. Symp.*, Oct. 2003; 1:1006-1009.
Yao et al., "Dual-mode ultrasound phased arrays for imaging and therapy," *Proc. IEEE Int. Symp. Biomed. Imag.*, Apr. 2004; 1:25-28.
Yuh et al., "Delivery of systemic chemotherapeutic agent to tumors by using focused ultrasound: Study in a murine model," *Radiology*, Feb. 2005; 234(2):431-437.
European Search Report and Search Opinion for European Patent Application No. 18193572.7, Sep. 2, 2019, 15 pages.
Golemati, "Carotid artery wall motion estimated from b-mode ultrasound using region tracking and block matching" 2003 *Ultrasound in Med & Biol.*, 29(3):387-399.
European Search Report for European Application No. 20176810.8; dated Jul. 27, 2020.
Aldiabat, "Real-Time Image-Based Transcranial Refocusing of Dual-Mode Ultrasound Arrays" Dissertation, Jan. 2019, 161 pages.
Alonso, "Focal delivery of AAV2/1-transgenes into the rat brain by localized ultrasound-induced BBB opening" 2013 *Mol Ther Nucleic Acids*, 2:e73.
Arvanhis, "Combined ultrasound and mr imag-ing to guide focused ultrasound therapies in the brain" Jul. 2013 *Phys Med Biol*, 58(14):4749-4761.
Aryal, "Multiple treatments with liposomal doxorubicin and ultrasound-induced disruption of blood-tumor and blood-brain barriers improve outcomes in a rat glioma model" Jul. 2013 *J Control Release*, 169(1-2):103-111.
Aubry, "Experimental demonstration of noninvasive transskull adaptive focusing based on prior computed tomography scans" 2013 *The Journal of the Acoustical Society of America*, 113(1):84-93.
Baek, "A review of low-intensity focused ultrasound for neuromodulation" 2017 *Biomed. Eng. Lett.* 7:135-142.
Baker, "A review of therapeutic ultrasound: biophysical effects" 2001 ;*Phys. Ther*. 81, 1351-1358.
Bakker, "The scalable brain atlas: Instant web-based access to public brain atlases and related content" 2015 *Neuroinformatics*, 13(3):353-366.
Ballard, "Dual-mode ultrasound arrays for image-guided targeting of atheromatous plaques" in *AIP Conference Proceedings* 1503, 124-128 (AIP, 2012).
Barber, "The density of tissues in and about the head" 1970 *Acta neurologica scandinavica*, 46(1):85-92.
Barnard, "Small localized ultrasonic lesions in the white and gray matter of the cat brain" 1956 *AMA Archives of Neurology & Psychiatry*, 75(1): 15-35.
Bayat, "Adaptive motion compensation for in vivo ultrasound temperature estimation" in Ultrasonics Symposium (IUS), 2013 IEEE International, pp. 1797-1800.

(56) References Cited

OTHER PUBLICATIONS

Bayat, "Ultrasound thermography in vivo: A new model for calculation of temperature change in the presence of temperature heterogeneity" in *2013 IEEE International Ultrasonics Symposium (IUS)*, pp. 116-119 (ieeexplore.ieee.org, 2013).
Botros, "A Hybrid Computational Model for Ultrasound Phased-Array Heating in Presence of Strongly Scattering Obstacles" Nov. 1997 IEEE Trans Biomed Eng., 44(11): 1039-1050.
Burgess, "Targeted delivery of neural stem cells to the brain using mri-guided focused ultrasound to disrupt the blood-brain barrier" 2011 *PLoS One*, 6(11):e27877.
Byrne, "Epidural cylinder electrodes for presurgical evaluation of intractable epilepsy: technical note" Aug. 2008 Surg Neurol., 70(2): 160-4; discussion 164. doi: 10.1016/j.surneu.2007.04.024. Epub Feb. 8, 2008.
Bystristsky, A review of low-intensity transcranial focused ultrasound for clinical applica-tions. *Curr Behav Neurosci*, 2:60-66, 2015.
Bystritsky, A review of low-intensity focused ultrasound pulsation. *Brain Stimul*, 4(3):125-136, Jul. 2011.
Casper, "Realtime Control of Multiple-focus Phased Array Heating Patterns Based on Noninvasive Ultrasound Thermography," 2010 *IEEE International Ultrasonics Symposium Proceedings*, pp. 467-470.
Casper, "Real-time implementation of a dual-mode ultrasound array system: In vivo results" 2013 IEEE Transactions on Biomedical Engineering, 60(10):2751-2759.
Chan, "Laser-generated focused ultrasound for arbitrary waveforms" 2016 *Appl. Phys. Lett.*, 109:174102.
Chan, Chapter 2 "Basics of Ultrasound Imaging" Narouze (Ed.), Atlas of Ultrasound-Guided Procedures in Interventional Pain Management, Springer: New York, NY; 2011. Cover page, publisher's page and pp. 13-19.
Chang, "Unilateral magnetic resonance guided focused ultrasound thalamotomy for essential tremor: practices and clinicoradiological outcomes" 2015 *J Neurol Neurosurg Psychiatry*, 86(3):257-264.
Chiao, "Coded excitation for diagnostic ultrasound: A system developer's perspective" Feb. 2005 *IEEE Trans. Ultrason., Ferroelect., Freq. Colllr.*, 52(2):160-170.
Chu, "Neuromodulation Accompanying Focused Ultrasound-Induced Blood-Brain Barrier Opening" Oct. 2015 *Scientific Reports* 5:15477; 12 pages.
Clement, "A noninvasive method for focusing ultrasound through the human skull" 2002 *Phys Med Biol.*, 47: 1219-1236.
Coluccia, "First noninvasive thermal ablation of a brain tumor with MR-guided focused ultrasound," 2014, *J Ther Ultrasound*, 2:17.
Constans, "A 200-1380-kHz Quadrifrequency Focused Ultrasound Transducer for Neurostimulation in Rodents and Primates: Transcranial In Vitro Calibration and Numerical Study of the Influence of Skull Cavity" 2017 *IEEE Trans Ultrason Ferroelectr Freq Control.*, 64(4):717-724. doi: 10.1109/TUFFC.2017.2651648. Epub Jan. 1, 20171.
Corl, "A real-time synthetic-aperture imaging system" in Acoustical Imaging vol. 9 Visualization and Characterization, 1980, Plenum Press. Cover page, copyright page and pp. 341-355.
Dallapiazza, "Noninvasive neuromodulation and thalamic mapping with low-intensity focused ultrasound" Apr. 2017, *J Neurosurg.*, 1-10. doi: 10.3171/2016.11.JNS16976. [Epub ahead of print].
Daniels, "Focused Ultrasound-Induced Suppression of Auditory Evoked Potentials in Vivo" 2018 *Ultrasound Med. Biol.* 44, 1022-1030.
Darrow, "Reversible neuroinhibition by focused ultrasound is mediated by a thermal mechanism" Nov.-Dec. 2019 *Brain Stimul.*, 12(6):1439-1447. doi: 10.1016/j.brs.2019.07.015. Epub Jul. 23, 2019. Prepublication.
Darrow, "Transcranial Focused Dual-Mode Ultrasound for Noninvasive Neuromodulation" presentation Sep. 30, 2018, Minnesota Neurological Society meeting; 34 pages.
Darvas, "Toward Deep Brain Monitoring with Superficial EEG Sensors Plus Neuromodulatory Focused Ultrasound" Aug. 2016, *Ultrasound Med Biol.*, 42(8):1834-47. doi: 10.1016/j.ultrasmedbio. 2016.02.020. Epub May 13, 2016.
Davies, "Pulse wave analysis and pulse wave velocity: A critical review of their strengths and weaknesses" Mar. 2003 *J Hypertens.*, 21(3):463-72.
Deffieux, "Low-intensity focused ultrasound modulates monkey visuomotor behavior" *2013 Current Biology*, 23(23):2430-2433.
Deng, "Targeted drug delivery across the blood-brain barrier using ultrasound technique" Dec. 2010 *Ther Deliv*, 1(6):819-848.
Dumas, "Piezocomposite technology an innovative approach to the improvement of ndt performance using ultrasounds" in 8th European Conference on Non Destructive Testing, Jun. 2002, Barcelona, Spain; 2 pages.
Dunmire, "Cross-beam vector doppler ultrasound for angle-independent velocity measurements" Oct. 2000 *Ultrasound Med Biol.*, 26(8):1213-1235.
Ebbini, "Fundamental resolution limits of a coded-excitation system for real-time pulse-echo imaging" in Nov. 1997 Proceedings of the IEEE Ultrasonics Symposium 2, 1997(2):1539-1542.
Ebbini, "A new Svd-based optimal inverse filter design for ultrasonic applications" in Ultrasonics Symposium, 1993. Proceedings., IEEE, 2:1187-1190.
Ebbini, "Real-time ultrasound thermography and thermometry [life sciences]" Mar. 2018 IEEE Signal Processing Magazine, 35:166-174.
Ebbini, "Region-adaptive motion tracking of speckle imagery" 2000 ICASSP, IEEE International Conference on Acoustics, Speech and Signal Processing—Proceedings. 4:2075-2078.
Elias, "A randomized trial of focused ultrasound thalamotomy for essential tremor" Aug. 2016, *New England Journal of Medicine*, 375(8):730-9.
Fisher, "Low-intensity focused ultrasound alters the latency and spatial patterns of sensory-evoked cortical responses in vivo" 2018 *J. Neural Eng.* 15, 035004.
Fry, "Ultrasonic lesions in the mammalian central nervous system" 1955, *Science*, 122(3168):517-518.
Fry, "Acoustical properties of the human skull" 1978 *The Journal of the Acoustical Society of America*, 63(5):1576-1590.
Fry, "Fundamental neurological research and human neurosurgery using intense ultrasound" 1960 *IRE transactions on medical electronics*, 3:166-181.
Fry, "Further studies of the transkull transmission of an intense focused ultrasonic beam: lesion production at 500 khz" 1980 *Ultrasound Med Biol*, 6(1):33-38.
Fry, "Production of focal destructive lesions in the central nervous system with ultrasound" 1954 *Journal of neurosurgery*, 11(5):471-478.
Fry, "Production of reversible changes in the central nervous system by ultrasound" 1958 *Science*, 127(3289):83-84.
Fry, "Transkull transmission of an intense focused ultrasonic beam" 1977 *Ultrasound in Medicine and Biology*, 3(2):183-184.
Fry, "Transkull focal lesions in cat brain produced by ultrasound" May 1981 *J Neurosurg*, 54(5):659-663.
Gelet, "845 Prostate cancer control with transrectal HIFU in 242 consecutive patients: 5-year results" Jan. 2004 *European Urology Supplements* 3(2):214-214.
Goodman, "*Introduction to Fourier Optics*" 2005, Roberts & Company, Greenwood Village, Colorado. Cover page, publisher page, table of contents.
Gulick, "Comparison of Electrical and Ultrasound Neurostimulation in Rat Motor Cortex" 2017 *Ultrasound Med. Biol.*, 43:2824-2833.
Gulick, "Effect of Ultrasound Stimulation on Excised Brain Tissue Impedance" 2013 *IEEE Neural Engineering Short Papers No. 0669*; 1 page.
Guo, "Ultrasound Produces Extensive Brain Activation via a Cochlear Pathway" 2018 *Neuron* 98:1020-1030.e4.
Haddadin, "Ultrasonic focusing through inhomogeneous media by application of the inverse scattering problem" Jul. 1998, *J Acoust Soc Am.*, 104(1): 313-325.
Hakimova, "Ultrasound stimulation inhibits recurrent seizures and improves behavioral outcome in an experimental model of mesial temporal lobe epilepsy" Aug. 2015 *Epilepsy Behav*, 49:26-32.

(56) References Cited

OTHER PUBLICATIONS

Hall, "Phantom materials for elastography" 1997 *IEEE transactions on ultrasonics, ferroelectrics, and frequency control*, 44(6):1355-1365.

Hameroff, "Transcranial ultrasound (TUS) effects on mental states: a pilot study" May 2013 *Brain Stimul.*, 6(3):409-15. doi: 10.1016/j.brs.2012.05.002. Epub May 29, 2012.

Haritonova, "In vivo application and localization of transcranial focused ultrasound using dual-mode ultrasound arrays" 2015 *IEEE transactions on ultrasonics, ferroelectrics, and frequency control*, 62(12):2031-2042.

Hirata, "Pulse wave analysis and pulse wave velocity: a review of blood pressure interpretation 100 years after Korotkov" Oct. 2006 *Circ J.*, 70(10):1231-9.

Hynynen, "Demonstration of potential noninvasive ultrasound brain therapy through an intact skull" 1998 *Ultrasound in medicine & biology*, 24(2):275-283.

Hynynen, "MR imaging-guided focused ultrasound surgery of fibroadenomas in the breast: a feasibility study" 2001 *Radiology*, 219(1):176-185.

Hynynen, "Noninvasive MR imaging-guided focal opening of the blood-brain barrier in rabbits" Sep. 2001 *Radiology*, 220(3):640-646.

Hynynen, "Pre-clinical testing of a phased array ultrasound system for mri-guided noninvasive surgery of the braina primate study" 2006 *European journal of radiology*, 59(2):149-156.

Hynynen, "Ultrasound for drug and gene delivery to the brain" Jun. 2008 *Adv Drug Deliv Rev*, 60(10):1209-1217.

Hynynen, "500-element ultrasound phased array system for noninvasive focal surgery of the brain: a preliminary rabbit study with ex vivo human skulls" 2004 *Magn. Reson. Med.*, 52:100-107.

Hyungmin, "Estimation of the spatial profile of neuromodulation and the temporal latency in motor responses induced by focused ultrasound brain stimulation" May 2014 *Neuroreport*, 25(7):475-479.

International Preliminary Report on Patentability dated Feb. 4, 2016 for International Patent Application No. PCT/US2014/047430, 13 pages.

International Search Report dated Jan. 20, 2015 for International Patent Application No. PCT/US2014/047430, 16 pgs.

Jedrzejewicz, "Two-way continuous transmit and receive focusing in ultrasound imaging" 2013 ZONARE Medical Systems, Inc., Tech. Rep., [Online], Available: http://res.mindray.com/Documents/2016-12-14/d2dd8ebd-a052-482a-8541-b8de227d4ee6/K90127_two_way_transmit_receive.pdf.

Jensen, "Calculation of pressure fields from arbitrarily shaped, apodized, and excited ultrasound transducers" 1992 *IEEE transactions on ultrasonics, ferroelectrics, and frequency control*, 39(2):262-267.

Jensen, "Synthetic aperture ultrasound imaging" 2006 *Ultrasonics*, 44:e5-e15.

Jones, "Comparison of analytical and numerical approaches for ct-based aberration correction in transcranial passive acoustic imaging" 2015 *Physics in Medicine & Biology*, 61(1): 23.

Jossinet, "Impedance Modulation by Pulsed Ultrasound" 1999 *Annals of the New York Academy of Sciences* 873 (1 Electrical BI):396-407.

Kamimura, "Focused ultrasound neuromodulation of cortical and subcortical brain structures using 1.9 MHz" 2016 *Med. Phys.* 43, 5730.

Khanna, "Intracranial Applications of MR Imaging-Guided Focused Ultrasound" 2017 *AJNR Am. J. Neuroradiol.* doi: 10.3174/ajnr.A4902, 426-431.

Khraicele, "Ultrasound induced increase in excitability of single neurons" 2008 *Conf Proc IEEE Eng Med Biol Soc.* 2008:4246-9. doi: 10.1109/IEMBS.2008.4650147.

Kim, "Estimation of the spatial profile of neuromodulation and the temporal latency in motor responses induced by focused ultrasound brain stimulation" 2014 *Neuroreport*, 25(7):475.

Kim "Focused ultrasound-mediated non-invasive brain stimulation: examination of sonication parameters" 2014 *Brain Stimul.*, 7(5):748-56. doi: 10.1016/j brs.2014.06.011. Epub Jul. 2, 2014.

Kim, "Noninvasive transcranial stimulation of rat abducens nerve by focused ultrasound" *Ultrasound in medicine & biology*, 38, No. 9, pp. 1568-1575, 2012.

Kim, "Suppression of EEG visual-evoked potentials in rats through neuromodulatory focused ultrasound" 2015 *Neuroreport* 26:211-215.

King, "Effective parameters for ultrasound-induced in vivo neurostimulation" *Ultrasound in medicine & biology*, 39, No. 2, pp. 312-331, 2013.

King, "Localization of ultrasound induced in vivo neurostimulation in the mouse model" *Ultrasound in medicine & biology*, 40, No. 7, pp. 1512-1522, 2014.

Kinoshita, "Noninvasive localized delivery of herceptin to the mouse brain by mri-guided focused ultrasound-induced blood-brain barrier disruption" *Proceedings of the National Academy of Sciences*, 2006, 103(31):11719-11723.

Konofagou, "Optimization of the ultrasound-induced blood-brain barrier opening" 2012 *Theranostics*, 2(12):1223-1237.

Krishna, "Prospective Tractography-Based Targeting for Improved Safety of Focused Ultrasound Thalamotomy" 2018 *Neurosurgery*. doi:10.1093/neuros/nyy020.

Kyriakou, "A review of numerical and experimental compensation techniques for skull-induced phase aberrations in transcranial focused ultrasound" 2014 *Int. J. Hyperthermia* 30:36-46.

Lalonde, "Field conjugate acoustic lenses for ultrasound hyperthermia" Sep. 1993 *IEEE Transactions on Ultrasonics, Ferroelectrics, and Frequency Control*, 40(5):592-602.

Lalonde, "Variable frequency field conjugate lenses for ultrasound hyperthermia" Sep. 1995 *IEEE Transactions on Ultrasonics, Ferroelectrics, and Frequency Control*, 42(5):825-831.

Legon, "Neuromodulation with single-element transcranial focused ultrasound in human thalamus" 2018 *Hum. Brain Mapp.* 39, 1995-2006.

Legon, "Transcranial focused ultrasound modulates the activity of primary somatosensory cortex in humans" 2014 *Nature Neurosci.*, 17(2):322-329.

Legon, "Transcranial focused ultrasound neuromodulation of the human primary motor cortex" 2018 *Sci. Rep.* 8:10007.

Lele, "The thermal hypothesis of the mechanism of ultrasonic focal destruction in organized tissues" Interaction of ultrasound and biological tissues. FDA, pp. 73-8008, 1972.

Lindsey, "Simultaneous bilateral real-time 3-d transcranial ultrasound imaging at 1 {MHz} through poor acoustic windows" 2013 *Ultrasound in Medicine and Biology*, 39(4) 721-734, 2013.

Lipsman, "MR-guided focused ultrasound thalamotomy for essential tremor: a proof-of-concept study" 2013 *The Lancet Neurology*, 12(5):462-468.

Liu, "Adaptive lesion formation using dual mode ultrasound array system" 2017 *AIP Conf. Proc.* 1821, 060003.

Liu, "In vivo mr quantification of superparamagnetic iron oxide nanoparticle leakage during low-frequency-ultrasound-induced blood-brain barrier opening in swine" Dec. 2011 *J Magn Reson Imaging*, 34(6):1313-1324.

Liu, "Magnetic resonance monitoring of focused ultrasound/magnetic nanoparticle targeting delivery of therapeutic agents to the brain" Aug. 2010 *Proc Natl Acad Sci U S A*, 107(34):15205-15210.

Liu, "Three-dimensional image guidance for transcranial focused ultrasound therapy" Apr. 2017 IEEE 14th International Symposium on Biomedical Imaging (ISBI 2017), 916-919.

Lockwood, "High-speed method for computing the exact solution for the pressure variations in the near field of a baffled piston" *The Journal of the Acoustical Society of America*, 53, No. 3, pp. 735-741:1973.

Luo, "Pulse wave imaging of normal and aneurysmal abdominal aortas in vivo" Apr. 2009 *IEEE Trans Med Imaging.*, 28(4):477-86.

Lynn, "Histology of cerebral lesions produced by focused ultrasound" 1944 *The American journal of pathology*, 20(3):637.

Maimbourg, "3d printed adaptive acoustic lens as a disruptive technology for transcranial ultrasound therapy using single-element transducers" 2018 *Physics in Medicine & Biology*, 63(2):025026.

(56) References Cited

OTHER PUBLICATIONS

Manlapaz, "Effects of ultrasonic radiation in experimental focal epilepsy in the cat" 1964 *Experimental neurology*, 10(4):345-356.
Marquet, "Non-invasive transcranial ultrasound therapy based on a 3d ct scan: protocol validation and in vitro results" May 2009 *Phys Med Biol*, 54(9):2597-2613.
Martin, "High intensity focused ultrasound for noninvasive functional neurosurgery" 2009 *Annals of Neurology: Official Journal of the American Neurological Association and the Child Neurology Society*, 66(6):858-861.
Marty, "Dynamic study of blood-brain barrier closure after its disruption using ultrasound: a quantitative analysis" Oct. 2012 *J Cereb Blood Flow Metab*, 32(10):1948-1958.
McDannold, "Transcranial magnetic resonance imaging-guided focused ultrasound surgery of brain tumors: initial findings in 3 patients" *Neurosurgery*, 66, No. 2, 323-332, 2010.
McGough, "Rapid calculations of time-harmonic nearfield pressures produced by rectangular pistons" *The Journal of the Acoustical Society of America*, 115, No. 5, pp. 1934-1941, 2004.
Mehic, "Increased anatomical specificity of neuromodulation via modulated focused ultrasound" 2014 *PLoS One*, 9(2):e86939.
Meyers, "Early experiences with ultrasonic irradiation of the pallidofugal and nigral complexes in hyperkinetic and hypertonic disorders" Jan. 1959 *J Neurosurg*, 16(1):32-54.
Min, "Focused ultrasound-mediated suppression of chemically-induced acute epileptic EEG activity" 2011 *BMC Neurosci.*, 12:23.
Misaridis, "Use of modulated excitation signals in medical ultrasound, part I: basic concepts and expected benefits" Feb. 2005 *IEEE Trans. Ultrason., Ferroelect., Freq. Colltr.*, 52(2): 177-191.
Montaldo, "Spatio-temporal coding in complex media for optimum beamforming: the iterative time-reversal approach" Feb. 2005 *IEEE Trans. Ultrason., Ferroelect., Freq. Comr.*, 52(2):220-230.
Mucci, "A comparison of efficient beamforming algorithms" 1984 *IEEE Transactions on Acoustics, Speech, and Signal Processing*, 32(3):548-558.
Mueller, "Transcranial Focused Ultrasound Modulates Intrinsic and Evoked EEG Dynamics" 2014 *Brain Stimul.*, 7:900-908.
Naor, "Ultrasonic neuromodulation" 2016 *J. Neural Eng.*, 13:031003.
Nichols, *McDonald's Blood Flow in Arteries*, Hodder Arnold: New York, NY; 2005. Cover page, title page and table of contents.
Ocheltree, "Sound field calculation for rectangular sources" 1989 *IEEE transactions on ultrasonics, ferroelectrics, and frequency control*, 36(2):242-248.
O'Donnell, "Coded excitation for synthetic aperture ultrasound imaging" Feb. 2005 *IEEE Trns. Ultrason., Ferroelect., Freq. Contr.*, 52(2):171-176.
Oppenheim et al., Discrete-time signal processing, Second Edition. Prentice-Hall, Upper Saddle River, New Jersey, 1999; 896 pages.
Patel, "Hard real-time closed-loop electrophysiology with the Real-Time eXperiment Interface (RTXI)" 2017 *PLoS Comput. Biol.*, 13:e1005430.
Paxinos, *"The mouse brain in sterotaxic coordinates"* 2004 Gulf Professional Publishing. Cover page, publisher page, table of contents.
Pinton, "Direct phase projection and transcranial focusing of ultrasound for brain therapy" 2012 *IEEE Trans Ultrason Ferroelectr Freq Control*, 59(6):1149-59.
Podgorski, "Brain heating induced by near-infrared lasers during multiphoton microscopy" 2016 *J. Neurophysiol.* 116:1012-1023.
Prada, "Decomposition of the time reversal operator: Detection and selective focusing on two scatterers" 1996 *The Journal of the Acoustical Society of America*, 99(4):2067-2076.
Raymond, "Ultrasound enhanced delivery of molecular imaging and therapeutic agents in Alzheimer's disease mouse models" 2008 *PLoS One*, 3(5):e2175.
Rezayat, "A Review on Brain Stimulation Using Low Intensity Focused Ultrasound" 2016 *Basic and Clinical Neuroscience*, 7 (3):187-94.

Rieke, "MR thermometry" 2008 *Journal of Magnetic Resonance Imaging: An Official Journal of the International Society for Magnetic Resonance in Medicine*, 27(2):376-390.
Rihaczek, "Radar waveform selection—a simplified approach" Nov. 1971 *IEEE Trans. Aerosp. Electron. Syst.*, AES-7(6):1078-1086.
Rohani, "Focused ultrasound for essential tremor: review of the evidence and discussion of current hurdles" *Tremor and Other Hyper-kinetic Movements*, 2017; 7. doi: 10.7916/D8Z89JN1.
Sakatani, "Somatosensory evoked potentials in rat cerebral cortex before and after middle cerebral artery occlusion" 1990 *Stroke* 21:124-132.
Salomir, "Image-based control of the magnetic resonance imaging guided focused ultrasound thermotherapy" 2006 *Topics in Magnetic Resonance Imaging*, 17(3):139-151.
Sato, "Ultrasonic Neuromodulation Causes Widespread Cortical Activation via an Indirect Auditory Mechanism" 2018 *Neuron* 98:1031-1041.e5.
Savitzky, "Smoothing and differentiation of data by simplified least squares procedures." *Analytical chemistry*, 3 6, No. 8, pp. 1627-1639, 1964.
Sawyer, "Nanoparticle-based evaluation of blood-brain barrier leakage during the foreign body response" *Journal of Neural Engineering*, 10(2013) 016013; 10 pages.
Schiefer, "Moving forward: Advances in the treatment of movement disorders with deep brain stimulation" 2011 *Frontiers in Integrative Neuroscience*, 5:69.
Shapoori, "An ultrasonic-adaptive beamforming method and its application for trans-skull imaging of certain types of head injuries; part i: Transmission mode" *IEEE Transactions on Biomedical Engineering*, 2015, 62(5):1253-1264.
Shehata, "Feasibility of targeting atherosclerotic plaques by high-intensity-focused ultrasound: an in vivo study" Dec. 2013 *J Vasc Interv Radiol*, 24(12):1880-1887.e2.
Shen, "On the design of a transversal filler bank for parallel processing multiple image lines in real-time acoustic imaging" in Acoustics, Speech, and Signal Processing, 1996. ICASSP-96. Conference Proceedings., IEEE International Conference, 6:3109-3112.
Shen, "Real-time 3d pulse-echo ultrasonic imaging with coded-excitation systems" in Image Processing, Oct. 1996. Proceedings. International Conference, 1:717-720.
Souchon, "Ultrasonic elastography using sector scan imaging and a radial compression" 2002 *Ultrasonics*, 40(1-8):867-871.
Szabo, "Diagnostic ultrasound imaging: inside out," Elsevier Academic Press, Burlington, Massachusetts, 2004. Title page, copyright page, and table of contents, 12 pages total.
Tanaka, "Active circulators—the realization of circulators using transistors" 1965 *Proceedings of the IEEE*, 53:260-267.
Ter Haar, "Therapeutic applications of ultrasound" 2007 *Prog. Biophys. Mol. Biol.*, 93:111-129.
Thomenius, "Recent Trends in Ultrasound Beamformation" Sep. 2005 IEEE Ultrasonics Symposium, Rotterdam, The Netherlands, 113 pages.
Treat, "Improved anti-tumor effect of liposomal doxorubicin after targeted blood-brain barrier disruption by MRI-guided focused ultrasound in rat glioma" Oct. 2012 *Ultrasound Med Biol*, 38(10):1716-1725.
Treat, "Targeted delivery of doxorubicin to the rat brain at therapeutic levels using mri-guided focused ultrasound" Aug. 2007 *Int J Cancer*, 121(4):901-907.
Tufail, "Transcranial pulsed ultrasound stimulates intact brain circuits" 2010 *Neuron* 66:681-694.
Tufail, "Ultrasonic neuromodulation by brain stimulation with transcranial ultrasound" Sep 2011 *Nat Protoc*, 6(9):1453-1470.
Tung, "The mechanism of interaction between focused ultrasound and microbubbles in blood-brain barrier opening in mice" Nov. 2011 *J Acoust Soc Am*, 130(5):3059-3067.
Tutwiler, "Ultrasonic beamforming architectures" in Medical Imaging 1998: Ultrasonic Transducer Engineering, 3341, pp. 43-55, *International Society for Optics and Photonics*, 1998.
Tyler, "Noninvasive neuromodulation with ultrasound? A continuum mechanics hypothesis" Feb. 2011*Neuroscientist*, 17(1):25-36.

(56) References Cited

OTHER PUBLICATIONS

Tyler, "Remote excitation of neuronal circuits using low-intensity, low-frequency ultrasound" Oct. 2008 *PLoS One*, 3(10):e3511. doi: 10.1371/journal.pone.0003511. Epub Oct. 29, 2008.
Vyas, "Extension of the angular spectrum method to calculate pressure from a spherically curved acoustic source" Nov. 2011 *J Acoust Soc Am.*, 130:2687-93.
Wagner, "Fundamental correlation lengths of coherent speckle in medical ultrasonic images" Jan. 1988 IEEE *Trans. Ultrason., Ferroelect., Freq. Contr.*, 35(1):34-44.
Wan, "A 2d post-beamforming filter for contrast restoration in medical ultrasound: in vivo results" 2009 *Conf. Proc IEEE Eng Med Biol Soc*, 2009:1945-8.
Wan, "A Post-Beamforming 2-D Pseudoinverse Filter for Coarsely Sampled Ultrasound Arrays" Sep. 2009 *IEEE Trans Ultrason Ferroelectr Freq Control.*, 56(9):1888-1902.
Wan, "Simultaneous imaging of tissue motion and flow velocity using 2D phase-coupled speckle tracking" 2010 *Proceedings—IEEE Ultrasonics Symposium*, 2010:487-490.
Weintraub, "The emerging role of transcranial magnetic resonance imaging-guided focused ultrasound in functional neurosurgery" 2016 *Movement Disorders*, 32(1):20-27.
White, "Effect of the skull in degrading the display of echoencephalographic b and c scans" *The Journal of the Acoustical Society of America*, 44, No. 5, pp. 1339-1345, 1968.
White, "The deformation of the ultrasonic field in passage across the living and cadaver head" *Medical and biological engineering*, 7, No. 6, pp. 607-618, 1969.
White, "Transcranial ultrasound focus reconstruction with phase and amplitude correction" 2005 *IEEE Trans. Ultrason. Ferroelectr. Freq. Control*, 52:1518-1522.
Wright, "Ultrasonic stimulation of peripheral nervous tissue: an investigation into mechanisms" 2015 *J. Phys. Conf. Ser.*, 581:012003.
Wulff, "Effects of ultrasonic vibrations on nerve tissues." *Proceedings of the Society for Experimental Biology and Medicine*, 1951, 76(2):361-366.
Yang, "Neuromodulation of sensory networks in monkey brain by focused ultrasound with MRI guidance and detection" 2018 *Sci. Rep.* 8:7993.
Yang, "Transcranial Ultrasound Stimulation: A Possible Therapeutic Approach to Epilepsy" 2011 *Medical Hypotheses* 76(3):381-83.
Ye, "Frequency Dependence of Ultrasound Neurostimulation in the Mouse Brain" 2016 *Ultrasound Med Biol.*, 42(7):1512-30.
Yin, "A numerical study of transcranial focused ultrasound beam propagation at low frequency" Apr. 2005 *Phys Med Biol*, 50(8):1821-1836.
Yoo, "Focused ultrasound modulates region-specific brain activity" 2011 *NeuroImage*, 56:1267-1275.
Yoshino, "Effects of focused ultrasound sonodynamic treatment on the rat blood-brain barrier" Mar. 2009 *Anticancer Res*, 29(3):889-895.
Younan, "Influence of the pressure field distribution in transcranial ultrasonic neurostimulation" Aug. 2013 *Med Phys*, 40(8):082902.
Zhang, "Defining the optimal age for focal lesioning in a rat model of transcranial hifu" Feb. 2015 *Ultrasound Med Biol*, 41(2):449-455.
English translation of Office Action for Chinese Patent Application No. 201810722985.7, Nov. 24, 2020, 15 pages.

\* cited by examiner

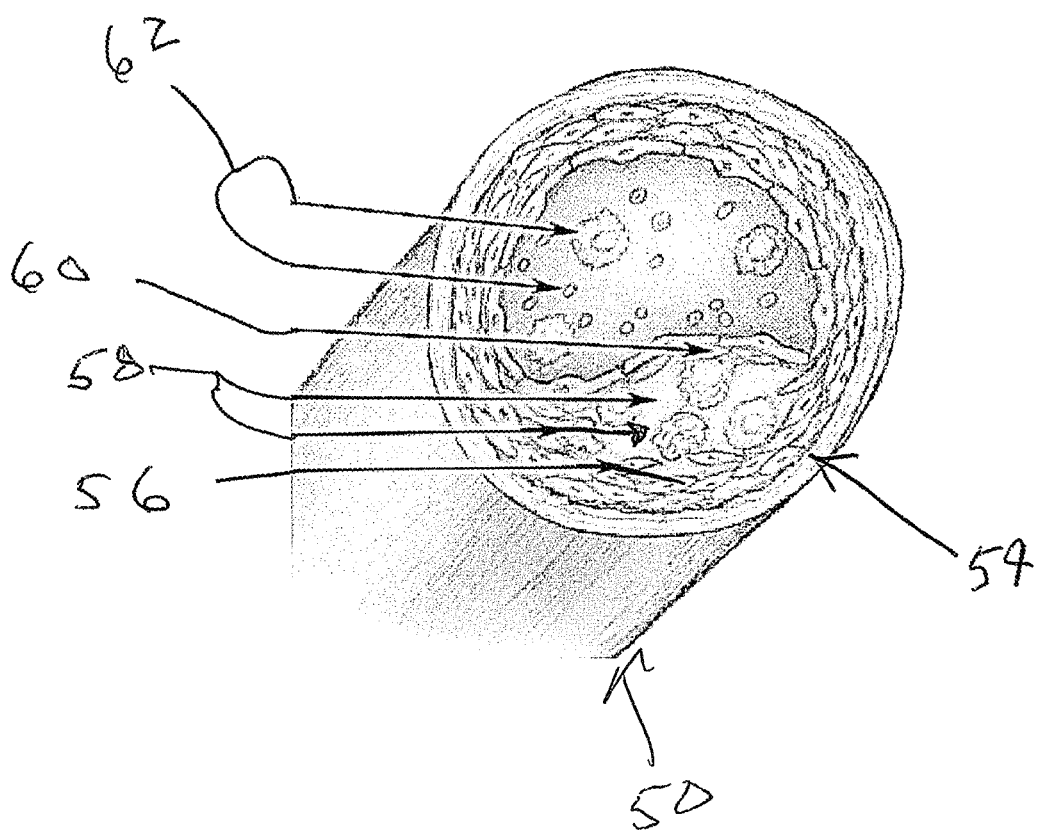

VASCULAR CHARACTERIZATION USING ULTRASOUND IMAGING

CROSS REFERENCE TO RELATED APPLICATIONS

This application is a divisional application of U.S. patent application Ser. No. 13/446,635, filed 13 Apr. 2012, which claims the benefit of U.S. Provisional Application Ser. No. 61/475,550, filed 14 Apr. 2011, entitled "Vascular Characterization Using Ultrasound Imaging," both of which are incorporated herein by reference in their entirety.

STATEMENT REGARDING FEDERALLY SPONSORED RESEARCH OR DEVELOPMENT

This invention was made with government support under EB006893 awarded by the National Institutes of Health. The government has certain rights in the invention.

BACKGROUND

The disclosure herein relates generally to ultrasound imaging. More particularly, the disclosure herein pertains to ultrasound imaging methods and systems for use in, e.g., diagnostic and/or therapy applications (e.g., imaging of blood vessels and/or regions proximate thereto, etc.).

Vascular imaging is gaining increased attention not only as a way to detect cardiovascular diseases, but also for the evaluation of response to new anti-atherosclerotic therapies (see, Ainsworth, et al., "3D ultrasound measurement of change in carotid plaque volume—A tool for rapid evaluation of new therapies," Stroke, vol. 36, no. 9, pp. 1904-1909, September 2005). Intravascular ultrasound (IVUS) has been shown to provide an effective tool in measuring the progression or regression of atherosclerotic disease in response to therapies. However, IVUS is invasive, potentially risky, and more expensive than noninvasive imaging with ultrasound.

Advanced imaging modes on ultrasound scanners have led to increased interest in imaging important quantities like wall shear rate (WSR) using Doppler (see, Blake, et al., "A method to estimate wall shear rate with a clinical ultrasound scanner," *Ultrasound in Medicine and Biology*, vol. 34, no. 5, pp. 760-764, May 2008) and tissue/wall motion (see, Tsou et al., "Role of ultrasonic shear rate estimation errors in assessing inflammatory response and vascular risk," *Ultrasound in Medicine and Biology*, vol. 34, no. 6, pp. 963-972, June 2008; Karimi et al., "Estimation of Nonlinear Mechanical Properties of Vascular Tissues via Elastography," *Cardiovascular Engineering*, vol. 8, no. 4, pp. 191-202, December 2008; and Weitzel, et al., "High-Resolution Ultrasound Elasticity Imaging to Evaluate Dialysis Fistula Stenosis," *Seminars In Dialysis*, vol. 22, no. 1, pp. 84-89, January-February 2009) using speckle tracking.

Recently, there has been increased interest in imaging flow in conjunction with computational fluid dynamic (CFD) modeling the evaluation of large artery hemodynamics (see, Steinman et al., "Flow imaging and computing: Large artery hemodynamics," *ANNALS OF BIOMEDICAL ENGINEERING*, vol. 33, no. 12, pp. 1704-1709, December 2005; Figueroa, et al., "A computational framework for fluid-solid-growth modeling in cardiovascular simulations," *Computer Methods in Applied Mechanics and Engineering*, vol. 198, no. 45-46, pp. 3583-3602, 2009; and Taylor et al., "Open problems in computational vascular biomechanics: Hemodynamics and arterial wall mechanics," *Computer Methods in Applied Mechanics and Engineering*, vol. 198, no. 45-46, pp. 3514-3523, 2009). In this context, modeling fluid-solid interfaces has been defined as a challenge area in vascular mechanics.

SUMMARY

At least one embodiment of this disclosure relates to ultrasound imaging capable of simultaneously imaging both wall tissue motion (e.g., perivascular tissue) and deformation, together with fluid flow. For example, in one embodiment of this disclosure, imaging vascular mechanics using ultrasound is accomplished utilizing speckle tracking (e.g., a 2D phase coupled speckle tracking method suitable for subsample displacement estimation in both axial and lateral directions with minimum interpolation) in conjunction with an imaging mode (e.g., M2D mode imaging) that provides sufficient frame rates for vector displacement tracking in both tissue and fluid simultaneously. For example, M2D imaging may be implemented on a clinical scanner equipped with a research interface for controlling the imaging sequence and streamlining the RF data for performing 2D speckle tracking in a region of interest (e.g., around a blood vessel). Combining 2D speckle tracking with sufficiently high frame rate imaging allows for fine displacement tracking in both lateral and axial directions. Vector displacement fields resulting from such processing are well suited for strain and shear strain calculations with minimum filtering and using relatively small tracking windows (i.e., speckle regions) to maximize resolution. Flow and tissue motion strain fields (e.g., in a tissue/flow application, such as in vivo in the carotid of a patient) may be evaluated (e.g., to identify vascular characteristics or for one or more other purposes, e.g., for use in therapy).

One exemplary embodiment of an imaging method may include providing ultrasound pulse-echo data of a region in which at least one portion of a blood vessel is located (e.g., wherein the pulse-echo data comprises pulse-echo data at a frame rate such that measured displacement of the vessel wall defining the at least one portion of the blood vessel and measured average blood flow through the at least one portion of the blood vessel have a quasi-periodic profile over time to allow motion tracking of both the vessel wall and the blood flow simultaneously) and generating strain and shear strain image data for the region in which the at least one portion of the vessel is located using speckle tracking. For example, the speckle tracking may include using multi-dimensional correlation of pulse-echo data of one or more speckle regions undergoing deformation in the region in which the at least one portion of a blood vessel is located (e.g., wherein the multi-dimensional correlation comprises determining a cross-correlation peak for the sampled pulse-echo data based on phase and magnitude gradients of the cross-correlated pulse-echo data). Further, the method may include identifying at least one vascular characteristic of the region in which at least one portion of a blood vessel is located based on the strain and shear strain image data (e.g., wherein the at least one vascular characteristic comprises at least one of a flow characteristic associated with flow through the blood vessel, a structural characteristic associated with the blood vessel, and a hemodynamic characteristic associated with the blood vessel).

Another exemplary imaging method may include providing ultrasound pulse-echo data of a region in which at least one portion of a blood vessel is located and using speckle tracking of one or more speckle regions of the region in which at least one portion of the blood vessel is located to track motion of both the vessel wall defining the at least one portion of the blood vessel and the blood flow through the at least one portion of the blood vessel. The pulse-echo data is provided at a frame rate such that displacement of the vessel wall defining the at least one portion of the blood vessel and blood flow through the at least one portion of the blood vessel are measurable simultaneously within a same periodic cycle (e.g., corresponding to a cardiac pulse cycle). Further, the method may include identifying at least one vascular characteristic of the region in which at least one portion of a blood vessel is located based on the simultaneously measured displacement of the vessel wall and average blood flow. Such an imaging method may also include generating strain and shear strain image data for the region in which the at least one portion of the vessel is located using the speckle tracking, wherein the speckle tracking comprises using multi-dimensional correlation of sampled pulse-echo data of the one or more speckle regions undergoing deformation in the region in which the at least one portion of a blood vessel is located (e.g., the multi-dimensional correlation may include determining a cross-correlation peak for the sampled pulse-echo data based on phase and magnitude gradients of the cross-correlated sampled pulse-echo data).

In one or more embodiments of methods described herein, identifying at least one vascular characteristic may include identifying one or more vessel wall boundaries; and still speckle tracking of such methods may include modifying a characteristic of at least one of the one or more speckle regions being tracked (e.g., location, size, shape, etc.) based on the one or more vessel wall boundaries identified such that the at least one speckle region is entirely within or outside of the vessel wall.

Further, in one or more embodiments of methods described herein, identifying at least one vascular characteristic may include identifying vessel wall boundaries around the entire blood vessel (e.g., wall boundaries in the entire cross-section view taken along the axis of the vessel); may include measuring tissue property within the one or more vessel wall boundaries (e.g., stiffness or compliance); may include identifying one or more portions of a plaque architecture adjacent the one or more vessel wall boundaries (e.g., such that therapy may be focused on a portion of such a structure; such as the base thereof); and/or may include calculating one or more hemodynamic measurements based on both the motion tracking motion of the vessel wall and the blood flow simultaneously.

Still further, in one or more embodiments of methods described herein, using multi-dimensional correlation of sampled pulse-echo data of one or more speckle regions may include using two-dimensional correlation of sampled pulse-echo data of one or more speckle regions (e.g., to track wall displacement or blood flow), and even three-dimensional correlation.

Yet further, in one or more embodiments of methods described herein, the method may further include delivering therapy to a patient based on the identification of the at least one vascular characteristic of the region in which at least one portion of a blood vessel is located (e.g., using ultrasonic energy to deliver therapy based on the identification of the at least one vascular characteristic of the region in which at least one portion of a blood vessel is located). For example, at least one transducer configured to transmit and receive ultrasonic energy may be provided, wherein the at least one transducer is used to obtain the pulse-echo data (e.g., for image data generation) and to generate ultrasonic energy to deliver therapy.

In one or more other embodiments of methods described herein, generating strain and shear strain image data for the region in which the at least one portion of the vessel is located using two-dimensional speckle tracking may include generating at least one of axial strain and axial shear strain image data and/or lateral strain and lateral shear strain image data. Further, in such methods, providing ultrasound pulse-echo data of a region in which at least one portion of a blood vessel is located may include using coded excitation.

In yet one or more other embodiments of methods described herein, the method may include applying a der-everberation filter to the pulse-echo data from one or more speckle regions in the blood to remove echo components in the pulse-echo data due to reflection at the vessel wall when performing speckle tracking of the pulse-echo data from the one or more speckle regions in the blood.

Another exemplary imaging method may include providing ultrasound pulse-echo data of a region in which at least one portion of a blood vessel is located; using speckle tracking of one or more speckle regions of the region in which the at least one portion of the blood vessel is located to track motion of at least one of the vessel wall defining the at least one portion of the blood vessel and the blood flow through the at least one portion of the blood vessel; identifying one or more vessel wall boundaries based on the speckle tracking of the one or more speckle regions; and modifying at least one characteristic of at least one of the one or more speckle regions being tracked based on the one or more vessel wall boundaries identified such that the at least one speckle region is entirely within or outside of the vessel wall (e.g., the at least one of the one or more speckle regions being tracked may be modified by at least one of location, size, or shape based on the one or more vessel wall boundaries identified such that the at least one speckle region is entirely within or outside of the vessel wall).

In another exemplary imaging method, the method may include providing ultrasound pulse-echo data of a region in which at least one portion of a blood vessel is located; using speckle tracking of one or more speckle regions of the region in which at least one portion of the blood vessel is located to track motion of at least blood flow through the at least one portion of the blood vessel; and removing echo components in the pulse-echo data due to reflection at the vessel wall when performing speckle tracking of the pulse-echo data from the one or more speckle regions in the blood (e.g., removing echo components in the pulse-echo data due to reflection at the vessel wall may include using a time-varying inverse filter to reduce the components in the pulse-echo data due to reflection at the vessel wall).

One exemplary embodiment of a system for vascular imaging may include one or more ultrasound transducers (e.g., wherein the one or more transducers are configured to deliver ultrasound energy to a vascular region resulting in pulse-echo data therefrom) and processing apparatus configured (e.g., operative by execution of one programs, routines, or instructions to cause the performance of one or more functions) to control the capture of pulse-echo data at a frame rate such that measured displacement of a vessel wall defining at least one portion of a blood vessel in the vascular region and measured average blood flow through the at least one portion of the blood vessel have a quasi-periodic profile over time to allow motion tracking of both the vessel wall and the blood flow simultaneously; to generate strain and shear strain image data for the region in which the at least one portion of the vessel is located using speckle tracking (e.g., wherein the speckle tracking may include using multi-dimensional correlation of pulse-echo data of one or more speckle regions undergoing deformation in the region in which the at least one portion of a blood vessel is located; the multi-dimensional correlation may include determining a cross-correlation peak for the sampled pulse-echo data based on phase and magnitude gradients of the cross-correlated pulse-echo data); and to identify at least one vascular characteristic of the vascular region in which at least one portion of a blood vessel is located based on the strain and shear strain image data (e.g., wherein the at least one vascular characteristic comprises at least one of a flow characteristic associated with flow through the blood vessel, a structural characteristic associated with the blood vessel, and a hemodynamic characteristic associated with the blood vessel).

Another exemplary system for vascular imaging may include one or more ultrasound transducers (e.g., wherein the one or more transducers are configured to deliver ultrasound energy to a vascular region resulting in pulse-echo data therefrom) and processing apparatus configured (e.g., operative by execution of one programs, routines, or instructions to cause the performance of one or more functions) to control the capture of pulse-echo data of the vascular region in which at least one portion of a blood vessel is located and use speckle tracking of one or more speckle regions of the vascular region in which at least one portion of the blood vessel is located to track motion of both the vessel wall defining the at least one portion of the blood vessel and the blood flow through the at least one portion of the blood vessel. The pulse-echo data may be captured at a frame rate such that displacement of the vessel wall defining the at least one portion of the blood vessel and blood flow through the at least one portion of the blood vessel are measurable simultaneously within a same periodic cycle corresponding to a cardiac pulse cycle. Further, the processing apparatus may be configured to identify at least one vascular characteristic of the vascular region in which the at least one portion of the blood vessel is located based on the simultaneously measured displacement of the vessel wall and average blood flow. In one embodiment of such a system, the processing apparatus may further be operable to generate strain and shear strain image data for the region in which the at least one portion of the vessel is located using the speckle tracking (e.g., wherein the speckle tracking may include using multi-dimensional correlation of sampled pulse-echo data of the one or more speckle regions undergoing deformation in the region in which the at least one portion of a blood vessel is located; and further wherein the multi-dimensional correlation may include determining a cross-correlation peak for the sampled pulse-echo data based on phase and magnitude gradients of the cross-correlated sampled pulse-echo data).

In one or more embodiments of the exemplary systems provided herein, the processing apparatus may be operable to identify one or more vessel wall boundaries, and still further, the processing apparatus may be operable, when using the speckle tracking, to modify a characteristic of at least one of the one or more speckle regions being tracked (e.g., the location, size, shape, etc.) based on the one or more vessel wall boundaries identified such that the at least one speckle region is entirely within or outside of the vessel wall.

Further, in one or more embodiments of the exemplary systems, the processing apparatus may be operable to identify vessel wall boundaries around the entire blood vessel; the processing apparatus may be operable to measure tissue property within the one or more vessel wall boundaries; the processing apparatus may be operable to identify one or more portions of a plaque architecture adjacent the one or more vessel wall boundaries; and/or the processing apparatus may be operable to calculate one or more hemodynamic measurements based on both the motion tracking motion of the vessel wall and the blood flow simultaneously.

Still further, in one or more embodiments of the exemplary systems provided herein, the processing apparatus may be operable to use two-dimensional correlation of sampled pulse-echo data of one or more speckle regions (e.g., to track speckle regions), and even three-dimensional correlation.

Yet further, in one or more embodiments of the exemplary systems provided herein, the system may further include a therapy apparatus to deliver therapy to a patient based on the identification of the at least one vascular characteristic of the region in which at least one portion of a blood vessel is located (e.g., a device operable to use ultrasonic energy to deliver therapy based on the identification of the at least one vascular characteristic of the region in which at least one portion of a blood vessel is located). For example, the therapy apparatus may include at least one transducer configured to transmit and receive ultrasonic energy, wherein the at least one transducer is operable to provide ultrasonic energy to deliver therapy based on the identification of the at least one vascular characteristic of the region in which at least one portion of a blood vessel is located and the at least one transducer is operable for use in obtaining the pulse-echo data to generate image data.

Still further, in one or more embodiments of the exemplary systems provided herein, the processing apparatus may be operable to generate strain and shear strain image data for the region in which the at least one portion of the vessel is located using two-dimensional speckle tracking, wherein using two-dimensional speckle tracking comprises generating at least one of axial strain and axial shear strain image data and/or lateral strain and lateral shear strain image data. Further, for example, the processing apparatus may be operable to control providing ultrasound pulse-echo data of a region in which at least one portion of a blood vessel is located using coded excitation.

Still further, in another of the one or more embodiments of the exemplary systems provided herein, the processing apparatus may be operable to apply a dereverberation filter to the pulse-echo data from one or more speckle regions in the blood to remove echo components in the pulse-echo data due to reflection at the vessel wall when performing speckle tracking of the pulse-echo data from the one or more speckle regions in the blood.

Another exemplary system for vascular imaging may include one or more ultrasound transducers (e.g., wherein the one or more transducers are configured to deliver ultrasound energy to a vascular region resulting in pulse-echo data therefrom) and processing apparatus configured to control capture of ultrasound pulse-echo data of the vascular region in which at least one portion of a blood vessel is located; use speckle tracking of one or more speckle regions of the vascular region in which the at least one portion of the blood vessel is located to track motion of at least one of the vessel wall defining the at least one portion of the blood vessel and the blood flow through the at least one portion of the blood vessel; identify one or more vessel wall boundaries based on the speckle tracking of the one or more speckle regions; and modify a characteristic of at least one of the one or more speckle regions being tracked based on the one or more vessel wall boundaries identified such that the at least one speckle region is entirely within or outside of the vessel wall. For example, the processing apparatus may be operable to modify at least one of location, size, or shape of the at least one speckle region based on the one or more vessel wall boundaries identified such that the at least one speckle region is entirely within or outside of the vessel wall.

In yet another exemplary system for vascular imaging, the system may include one or more ultrasound transducers (e.g., wherein the one or more transducers are configured to deliver ultrasound energy to a vascular region resulting in pulse-echo data therefrom) and processing apparatus configured to control capture of ultrasound pulse-echo data of the vascular region in which at least one portion of a blood vessel is located; use speckle tracking of one or more speckle regions of the region in which at least one portion of the blood vessel is located to track motion of at least blood flow through the at least one portion of the blood vessel; and remove echo components in the pulse-echo data due to reflection at the vessel wall when performing speckle tracking of the pulse-echo data from the one or more speckle regions in the blood (e.g., using a time-varying inverse filter to reduce the components in the pulse-echo data due to reflection at the vessel wall).

Still further, another exemplary system for vascular imaging may include one or more ultrasound transducers (e.g., wherein the one or more transducers are configured to deliver ultrasound energy to a vascular region resulting in pulse-echo data therefrom); apparatus for controlling the capture of pulse-echo data at a frame rate such that measured displacement of a vessel wall defining at least one portion of a blood vessel in the vascular region and measured average blood flow through the at least one portion of the blood vessel have a quasi-periodic profile over time to allow motion tracking of both the vessel wall and the blood flow simultaneously; apparatus for generating strain and shear strain image data for the region in which the at least one portion of the vessel is located using speckle tracking (e.g., wherein the speckle tracking may include using multi-dimensional correlation of pulse-echo data of one or more speckle regions undergoing deformation in the region in which the at least one portion of a blood vessel is located, and further wherein the multi-dimensional correlation may include determining a cross-correlation peak for the sampled pulse-echo data based on phase and magnitude gradients of the cross-correlated pulse-echo data); and apparatus for identifying at least one vascular characteristic of the vascular region in which at least one portion of a blood vessel is located based on the strain and shear strain image data (e.g., wherein the at least one vascular characteristic comprises at least one of a flow characteristic associated with flow through the blood vessel, a structural characteristic associated with the blood vessel, and a hemodynamic characteristic associated with the blood vessel). Further, for example, the system may include therapy apparatus for delivering therapy to a patient based on the identification of the at least one vascular characteristic of the region in which at least one portion of a blood vessel is located (e.g., ultrasound therapy apparatus).

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 provides an exemplary image of a blood vessel for use in describing one or more methods and/or systems shown generally in FIGS. 1-2 as they relate to vascular diagnostics or vascular therapy.

DETAILED DESCRIPTION OF EXEMPLARY EMBODIMENTS

Figure 1:
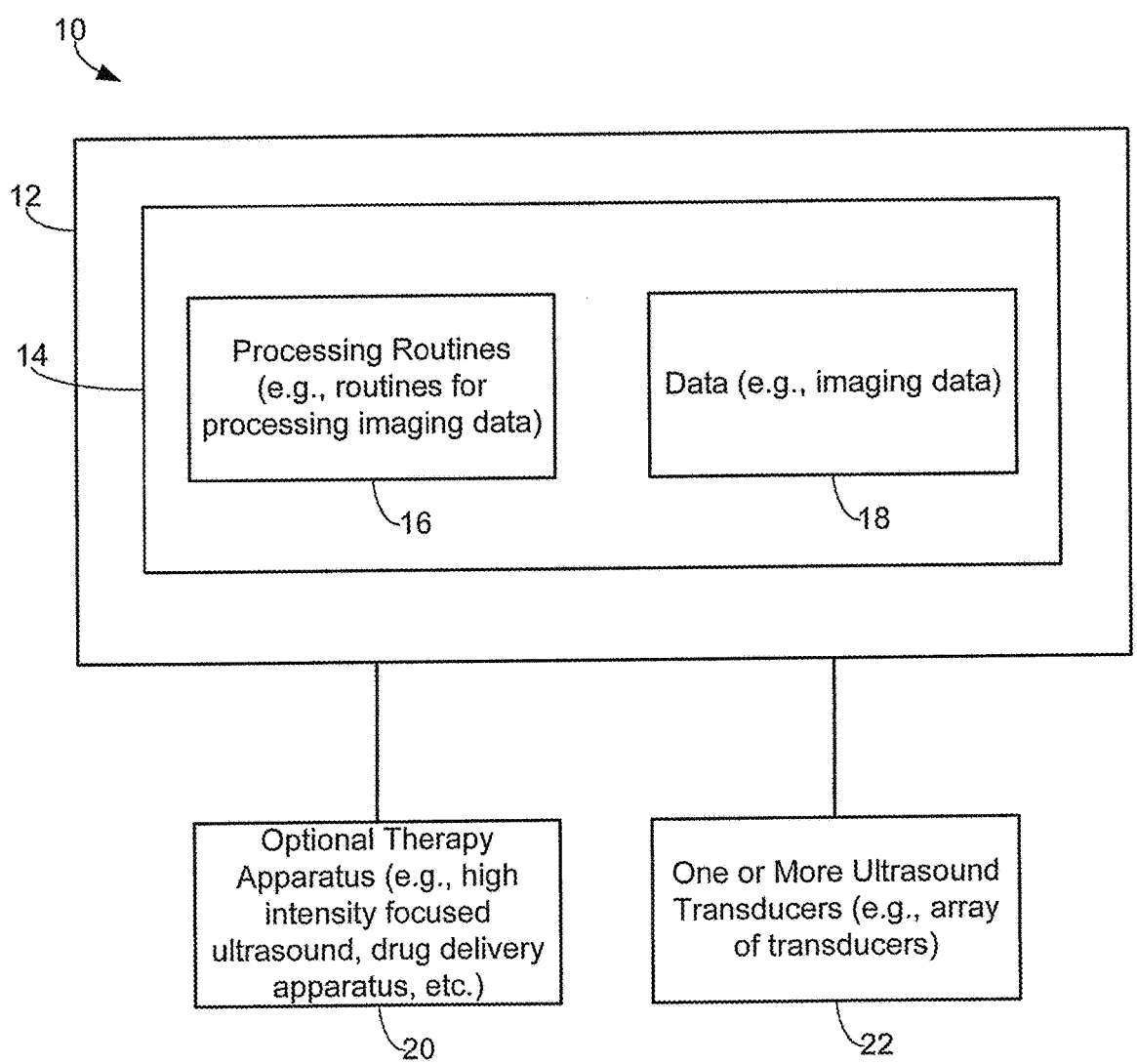
FIG. 1 is a block diagram depicting an exemplary ultrasound imaging system, with an optional therapy system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-19. It will be apparent to one skilled in the art that elements or processes (e.g., including steps thereof) from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 shows an exemplary ultrasound imaging system 10 including processing apparatus (block 12) and one or more ultrasound transducers, such as a transducer array that provides for transmission of pulses and reception of echoes (block 22). The processing apparatus (block 12) may be operably coupled to the one or more transducers (block 22) to facilitate imaging of an object of interest (e.g., capture of pulse-echo data) using the one or more transducers (block 22). Further, the processing apparatus (block 12) includes data storage (block 14). Data storage (block 14) allows for access to processing programs or routines (block 16) and one or more other types of data (block 18) that may be employed to carry out the exemplary imaging methods (e.g., one which is shown generally in the block diagram of FIG. 2).

For example, processing programs or routines (block 16) may include programs or routines for performing computational mathematics, matrix mathematics, compression algorithms (e.g., data compression algorithms), calibration algorithms, image construction algorithms, inversion algorithms, signal processing algorithms, standardization algorithms, comparison algorithms, vector mathematics, or any other processing required to implement one or more embodiments as described herein (e.g., provide imaging, carry out speckle tracking, generate strain images, etc.). Exemplary mathematical formulations/equations that may be used in the systems and methods described herein are more specifically described herein with reference to FIGS. 3-19.

Data (block 18) may include, for example, sampled pulse-echo information (e.g., sampled or collected using the one or more transducers (block 22)), data representative of measurements (e.g., vascular characteristics), results from one or more processing programs or routines employed according to the disclosure herein (e.g., reconstructed strain images of an object of interest, such as a blood vessel or regions around same), or any other data that may be necessary for carrying out the one or more processes or methods described herein.

In one or more embodiments, the system 10 may be implemented using one or more computer programs executed on programmable computers, such as computers that include, for example, processing capabilities (e.g., computer processing units (CPUs), graphical processing units (GPUs)), data storage (e.g., volatile or non-volatile memory and/or storage elements), input devices, and output devices. Program code and/or logic described herein may be applied to input data to perform functionality described herein and generate desired output information (e.g., strain images, vascular characteristics, etc.). The output information may be applied, or otherwise used, as input to, or by, one or more other devices and/or processes as described herein (e.g., one or more therapy apparatus (block 20) such as a drug therapy apparatus, an ultrasound therapy apparatus, etc.).

The program(s) or routine(s) used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer (e.g., processor(s)) when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein.

Likewise, the imaging system 10 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processing apparatus (block 12), may be, for example, any fixed or mobile computer system (e.g., a personal computer or minicomputer, for example, with a CPU, GPU, etc.). The exact configuration of the computing apparatus is not limiting and essentially any device capable of providing suitable computing capabilities and control capabilities (e.g., control the imaging set up configuration and acquire data, such as pulse-echo data) may be used. Further, various peripheral devices, such as a computer display, mouse, keyboard, memory, printer, scanner, etc. are contemplated to be used in combination with the processing apparatus (block 12), such as for visualization of imaging results (e.g., display of strain images, display of therapy delivery in real time such as with use of high intensity focused ultrasound, etc.).

Further, in one or more embodiments, the output (e.g., an image, image data, an image data file, a digital file, a file in user-readable format, etc.) may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus (block 14) described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to reconstruct the images described herein (e.g., from pulse-echo data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, image processing devices, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The imaging system 10 may further be used with, or may form a part of an optional therapy apparatus (block 20). For example, the therapy apparatus (block 20) may use the results of ultrasound imaging to provide one or more therapies. In one or more embodiments, the therapy apparatus (block 20) may be a non-invasive or invasive therapy apparatus such as a drug delivery apparatus or system (delivery of a drug to a particular location), a surgical apparatus or system (e.g., delivery of a stent to a particular position), an ablation apparatus or system (e.g., a high frequency or high intensity focused ultrasound therapy apparatus or system), etc.

In one or more embodiments, the therapy apparatus (block 20) may be a separate system or apparatus that receives an output from the imaging system (e.g., image information) and delivers one or more therapies. In other embodiments, the therapy apparatus (block 20) may be integrated with the imaging system to perform the one or more therapies (e.g., a high intensity focused ultrasound system that uses dual mode ultrasound transducer(s); for diagnostics such as imaging, as well as for treatment, such as ablation). For example, in one or more embodiments, the therapy apparatus (block 20) may include one or more portions of a system such as described in PCT International Publication No. WO2009/002492 entitled "Image Guided Plaque Ablation," published 31 Dec. 2008, and incorporated herein by reference. For example, the ultrasound imaging described herein may be used for reducing vascular plaque non-invasively. For example, the ultrasound imaging described herein may be used to identify flow and vascular characteristics needed to non-invasively perform ablation of plaque as described in PCT International Publication No. WO2009/002492.

For example, the therapy system may be a system for non-invasively elevating the temperature of tissue by ultrasound energy waves including: at least one ultrasound delivery device adapted to deliver ultrasound energy waves to a focal point of targeted tissue; a temperature monitoring device for monitoring the temperature of targeted tissue at the focal point; and a controller for steering and controlling the ultrasound delivery device to deliver ultrasound energy waves at a focal point to elevate the temperature of targeted tissue to a desired temperature.

Further, for example, the therapy system may use one or more imaging systems described herein to produce an image of at least a portion of a mammalian body, e.g., such that the location of at least one vascular plaque in said image can be determined and to ascertain the location of the base of said vascular plaque. For example, ultrasound delivery device may ascertain one or more target locations at the base of the plaque. Still further one or more embodiments of the imaging system provided herein may be used in a method for elevating the temperature at a target location by an energy wave using an ultrasound therapy system (e.g., which may be the same ultrasound system (ultrasound transducers thereof) used for imaging). For example, the method may include delivering a beam of ultrasound energy waves from a source to the target location; monitoring the temperature of the target location; and stopping the delivering of the beam of ultrasound energy waves if a desired temperature at the target location has been reached.

Further, a method of preparing a plan for non-invasively elevating the temperature of tissue in a vessel wall leading to regression of vascular plaques may include imaging at least a portion of a body to produce an image (e.g., using ultrasound imaging as described herein to image a vascular region); determining the location of at least one vascular plaque in said image; ascertaining the location of the base of said vascular plaque and one or more target locations at the base of the plaque (e.g., using the ultrasound generated image); and/or determining the parameters for delivering ultrasound energy waves from a source to a focal point for elevating the temperature of targeted tissue in the vessel wall to a desired temperature, sufficient for reducing or destroying vaso vasorum.

Further, for example, the ultrasound imaging described herein may be used to identify flow and vascular characteristics needed to perform invasive treatments of plaque (e.g., stent delivery, cardiac surgery, etc.)

Still further, in one or more embodiments, the therapy apparatus (block 20) may include one or more portions of a system such as described in U.S. Provisional Patent Application No. 61/353,096, entitled "Dual Mode Ultrasound Transducer (DMUT) System for Monitoring and Control of Lesion Formation Dynamics" filed 9 Jun. 2010, and which is incorporated by reference herein. For example, the ultrasound imaging described herein may be performed with the same or similar transducer arrays described therein which can be used for both imaging (e.g., to monitor a therapy procedure), as well as for delivering therapy (e.g., to deliver high intensity focused ultrasound energy). For example, therapy may be delivered using the ultrasound transducer array, while the imaging modes using the same transducer array may be used to guide the therapeutic beam, assess thermal and mechanical tissue response to estimate doses of therapy (e.g., initial dose of therapy), monitor and characterize tissue response during therapy, and assess the state of the treated tissue at the completion of each exposure to the therapeutic ultrasound energy (e.g., real time monitoring between periods of therapy delivery).

For example, ultrasound imaging as described herein may be used to identify one or more vascular characteristics. An exemplary diagram of a blood vessel 50 is shown in FIG. 7 to facilitate discussion of the use of imaging described herein. The blood vessel 50 shown in FIG. 7 includes a vessel wall 52 having a plaque structure 54 formed on the interior of the vessel wall 52. The plaque architecture of the structure 54 may include, for example, a plaque base 56, a lipid core 58, and a fibrous or calcified cap 60. Blood 62 flows through the blood vessel 50 defined by the vessel wall 52.

One or more embodiments of methods and/or systems described herein may be used to identify one or more vascular characteristics, e.g., flow characteristics associated with the flow through the blood vessel 50, structural characteristics associated with the blood vessel 50, and/or hemodynamic characteristics. For example, flow characteristics may include flow velocity, volume flow, wall shear stress, wall shear rate, etc.

For example, structural characteristics may include determining boundaries of the vessel wall (e.g., outer and inner boundaries, such as in a coordinate system), thickness of the vessel wall, measurement of tissue properties within the vessel wall (e.g., stiffness of tissue, such as, for example, it relates to a diseased state), differentiation of plaque from vessel wall, differentiation of the various components of plaque (e.g., differentiation of base from lipid core, differentiation of base from fibrous cap, differentiation of lipid core from fibrous cap, etc.), etc. For example, in one or more embodiments, upon differentiation of the base from the fibrous cap of the plaque architecture, treatment may be provided to ablate the base to reduce further plaque buildup or growth or provide treatment according to PCT International Publication No. WO2009/002492.

Still further, for example, hemodynamic characteristics may include calculated hemodynamic measurements, such as, for example, arterial pressure, cardiac output, arterial compliance, pulse wave velocity, etc. At least in one embodiment, such hemodynamic measurements may be determined based on parameters relating to both tracking of the blood flow and tracking of vessel wall motion or displacement. As such, to obtain an accurate hemodynamic determination, the parameters or measurements relating to both tracking of the blood flow and tracking of vessel wall motion or displacement must be determined simultaneously, or within a periodic cycle in which both can be determined (e.g., determined effectively). For example, compliance of the vessel may be based on both volume flow which relates to tracking of blood flow and pressure within the vessel which can be determined by tracking vessel displacement.

For example, accurate estimation of the vessel diameter and estimation of the lateral flow within the lumen with high frame rate imaging will allow for useful measurement of the pulse wave velocity (PWV) noninvasively. For example, the time waveforms shown in, for example, FIGS. 5C-5D can be plotted in phase space (volume flow, $Q_A$, vs. vessel area, A). Volume flow can be calculated from the flow data, while the area can be obtained from the vessel wall movement. This measurement must be made during the reflection-free part of the heart cycle in the form of a slope measurement of the form PWV=dQ/dA. With the adequately sampled time waveforms (e.g., using M2D mode imaging), the task of estimating the vessel wall motion and the flow within the vessel can be accomplished.

In other words, both lateral flow velocity and wall motion can be estimated simultaneously thus providing pressure (through vessel diameter) and flow (through vector velocity)). Such measurements can provide the basis for hemodynamic computations that may be used in the assessment of vessel wall compliance, an important indicator of the health of the vessel as described herein. Further, as described herein, axial and lateral displacement fields are well-behaved and allow for strain and shear strain calculations in both tissue and blood. Together with anatomical image information, these velocity/strain fields may provide input for computational fluid dynamic models, which may allow for inverse calculations suitable for the assessment of the health of the vasculature and surrounding tissue (e.g. detection and staging of atherosclerosis).

In one or more embodiments, the ultrasound-enabled quantitative imaging system may be used for assessment of the disease state in atherosclerotic blood vessels. For example, the imaging may be used for the direct estimation of the strain fields in the vicinity of the vessel walls. Such methods may mitigate the deleterious effects of local deformations that could result in loss of correlation, and which may render the correlation-based speckle tracking approach useless in the vicinity of the vessel wall. Such deformations, depending on severity, could result in erroneous estimate in the velocity (and therefore strain) estimation or may even result in loss of accuracy.

A three-pronged approach to the problem of restoring the true velocity/strain estimates may include: 1) A two-step algorithm for direct estimation of the velocity/strain components using a deformed model of the 2D RF data in the vicinity of the wall, 2) A reconstructive approach employing a forward computational fluid dynamics (CFD) model as a regularization filter, and 3) A quantitative inverse reconstruction of the tissue mechanical properties using ultrasound-based velocity/strain fields as observations. As described herein, simultaneous imaging of tissue motion and flow with subsample accuracy in both axial and lateral directions may be implemented. For example, such imaging may include using a phase-coupled 2D speckle tracking approach, which employs the true 2D complex cross correlation to find sub-pixel displacements in both axial and lateral directions. Further, a modified imaging sequence on a Sonix RP scanner to allow high frame rate 2D data collection in a limited field of view covering the region of interest (M2D-mode) may be used. Together with the robust 2D speckle tracking method, M2D imaging allows for capturing the full dynamics of the flow and wall/tissue motion, even when the flow is primarily in the lateral direction (with respect to the imaging beam). The fine vector displacement estimates in both axial and lateral directions are shown to allow for smooth and contiguous strain and shear strain calculations with minimal filtering. The simultaneous imaging of the vector flow field and the wall/tissue motion and the corresponding strains at high spatial and temporal sampling may provide a tool in modeling the fluid-solid interactions between the blood and blood vessel. Such an image-based modeling of the vessel response may allow for the prediction of the disease state and possible evolution of the disease state.

Furthermore, the integration between the observation model and inverse reconstruction of the tissue properties in the vicinity of the vessel wall may allow for quantitative assessment of the plaque composition (e.g. lipid content or calcification). This may provide a reliable noninvasive model for selecting treatment options based on probability of rupture and other risk factors.

In other words, the imaging described herein may be used in conjunction with computational fluid dynamic (CFD) modeling the evaluation of large artery hemodynamics CFD has been shown to produce useful prediction of time-varying, 3D flow fields in large arteries with complex geometries. In this context, modeling fluid-solid interfaces has been defined as a challenge area in vascular mechanics. Imaging methods as described herein capable of capturing both perivascular (and wall) tissue motion and deformations, together with fluid flow may be used to address this issue. Advances in MRI and other imaging modalities have led to increased interest in image-based, patient-specific CFD modeling to monitor disease progression. MRI has excellent soft tissue contrast that may allow the accurate capture of the tissue (solid) model. Although this may be an advantage over diagnostic ultrasound, which does not offer the same level of definition for tissue boundaries and discrimination between tissue types, this limitation may be mitigated, however, by the recent improvements in 3D image acquisition, both freehand and motorized. Therefore, diagnostic ultrasound scanners may provide an attractive alternative for image-based CFD modeling. Based on 3D ultrasound and improved 2D velocity/strain imaging using M2D mode, processes for providing quantitative tissue property images in the vicinity of the vessel wall for the characterization of the disease state may be implemented. The imaging methods described herein address the limitations of existing correlation-based methods for velocity/strain estimation to restore the lost or artifact-ridden estimates in the vicinity of the wall. Further, the integration of our velocity/strain estimation as an observation model in a dynamic, forward/inverse CFD-based model for the reconstruction of the field/tissue property values consistent with the Navier-Stokes equations may be accomplished. For example, the following may be developed: a two-step algorithm for direct strain estimation at the vessel wall using M2D-mode data; a regularized approach for the reconstruction of displacement/strain maps utilizing a forward CFD model obtained from 3D Ultrasound (e.g., the forward model may provide a reconstruction filter to regularize the velocity/strain estimation obtained using the speckle tracking algorithm); and/or an inverse method for the reconstruction of the mechanical properties in the vicinity of the vessel wall based on strain maps obtained using M2D-mode data.

The one or more ultrasound transducers (block 22) may be any apparatus (e.g., transmitting, receiving components, etc.) capable of delivering ultrasound pulses and sampling/collecting ultrasound echo energy contemplated to be used in ultrasound imaging systems and in combination with processing apparatus (block 12) of the system 10. As used herein, such transducers may include a transmitting portion, e.g., to deliver pulse energy, and a receiving portion, e.g., to sample/collect echo or reflected energy, which may or may not be the same portion. During the ultrasound imaging of a target (e.g., a blood vessel, such as a carotid artery, coronary artery, etc.), the one or more transducers (block 22) may be positioned relative to the target so as to be capable of delivering energy to the target resulting in reflected energy (also known as the resultant pulse-echo or echo energy) and also sampling the echo energy.

The one or more transducers (block 22) may include multiple transducers position separately from one another or may be a transducer array. In one or more embodiments, various arrays may have one or more benefits over others. For example, in one or more embodiments, the transducer array may be a segmented concave transducer with multiple sub-apertures to insonify the vessel from multiple angles. This will allow for better definition of the vessel boundaries from more directions. At least one sub-aperture may be used in linear array or phased array mode for initial B-mode and strain imaging of the vessel. The driver of the transducer may be designed to drive the multiple sub-apertures with independent codes. Each sub-aperture may be a one-dimensional or two-dimensional array. Coded excitation may help improve both the data rates (e.g., provide higher frame rates) and echo quality (e.g., by reducing reverberations within the lumen). The receiver may be a multichannel receiver with beamforming and/or pulse compression for coded excitation.

For example, various arrays and operation thereof, are described in Ebbini, et al., "Dual-Mode Ultrasound Phased Arrays for Image-Guided Surgery," *Ultrasound Imaging*, vol. 28, pp. 65-82 (2006); Ballard, et al., "Adaptive Transthoracic Refocusing of Dual-Mode Ultrasound Arrays," *IEEE Transactions on Biomedical Engineering*, vol. 57, no. 1, pp. 93-102 (January 2010); and Wan et al., "Imaging with Concave Large-Aperture Therapeutic Ultrasound Arrays Using Conventional Synthetic-Aperture Beamforming," *IEEE Transactions on Ultrasound, Ferroelectrics, and Frequency Control*, vol. 55, no. 8, pp. 1705-1718 (August 2008), which are all hereby incorporated by reference herein.

Figure 2:
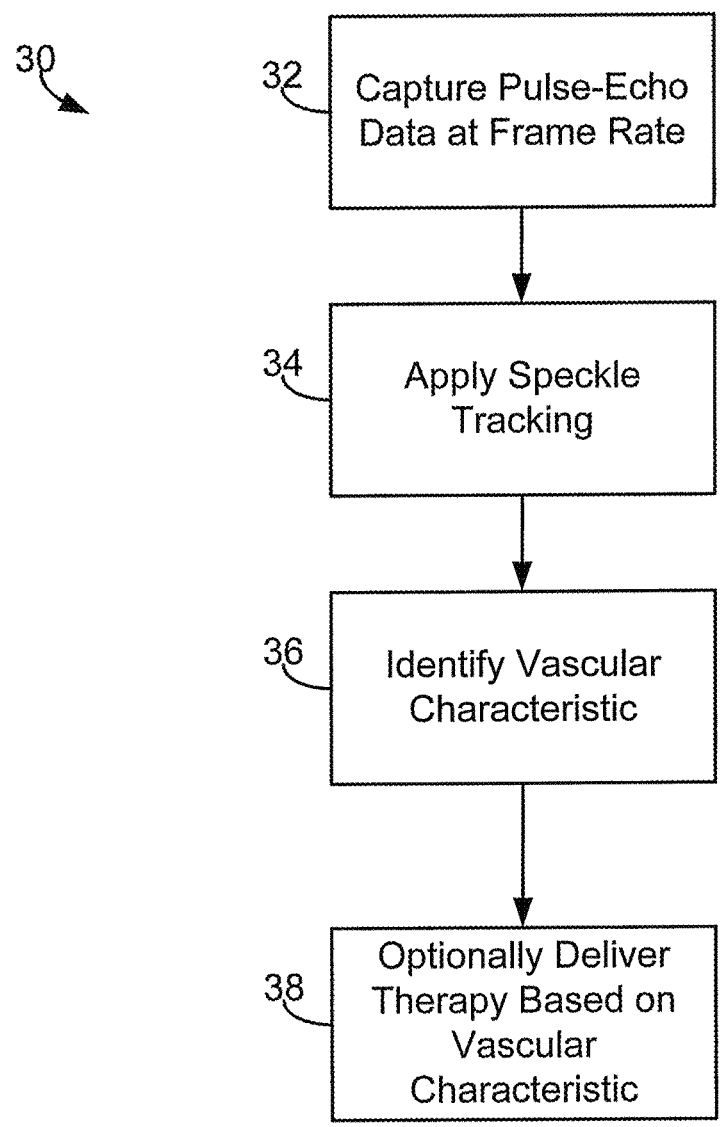
FIG. 2 is a flow chart depicting an exemplary ultrasound imaging method.

A flow chart of an exemplary ultrasound imaging method 30 for vascular imaging is depicted in FIG. 2. One will recognize that one or more of the blocks of functionality described herein may be carried out using one or more programs or routines, and/or any other components of an imaging system (e.g., the imaging system 10 of FIG. 1) and/or therapy system (e.g., the therapy system 20 of FIG. 1).

Generally, the method 30 provides for the capture of pulse-echo data at a sampled frame rate (block 32). In one embodiment, ultrasound pulse-echo data is provided of a region in which at least one portion of a blood vessel is located. For example, the pulse-echo data may be pulse-echo data sampled at a frame rate such that measured displacement of the vessel wall defining the at least one portion of the blood vessel and measured average blood flow through the at least one portion of the blood vessel have a quasi-periodic profile over time to allow motion tracking of both the vessel wall and the blood flow simultaneously. Further, the method includes applying speckle tracking (block 34) to the pulse-echo data to allow, for example, the generation of strain and shear strain image data.

As set forth herein with respect to the system shown in FIG. 1, one or more vascular characteristics, e.g., flow characteristics associated with the flow through the blood vessel 50, structural characteristics associated with the blood vessel 50, and/or hemodynamic characteristics, may be identified (block 36) based on the tracking of motion in the vessel wall and flow. In one embodiment, due the simultaneous capture of displacement fields in both the flow and vessel wall, e.g., during a periodic cycle, such as a cardiac cycle, one or more vascular characteristics which depend on measurements resulting from or relating to both such types of displacements (e.g., such as hemodynamics) may be determined.

Still further, as shown in FIG. 2, optionally the method 30 may include delivering therapy based on one or more vascular characteristics (block 38). For example, as described with respect to the system of FIG. 1, delivery of therapy may take one or more different forms (e.g., drug, ablation, surgical, or any other invasive or non-invasive treatment).

In one or more embodiments, the method may include M2D mode imaging designed to maximize the lateral extent of the imaged region at sufficiently high frame rates to capture the full dynamics of the vessel wall and the flow within the vessel. M2D mode produces 2D beamformed RF echo data from a selected region of the field of view (FoV) of a given probe. The region may be contiguous or comprised of more than one disjoint subsegments. As an example, on the SonixRP scanner (Ultrasonix, BC, Canada), an arbitrary set of A-lines within the FoV can be used to faun the M2D mode image with frame mode approximately $M_B/M_{M2D}$ higher than B-mode imaging, where $M_B$ and $M_{M2D}$ indicate the number of A-lines used to form B-mode and M2D-mode images, respectively.

Figure 4:
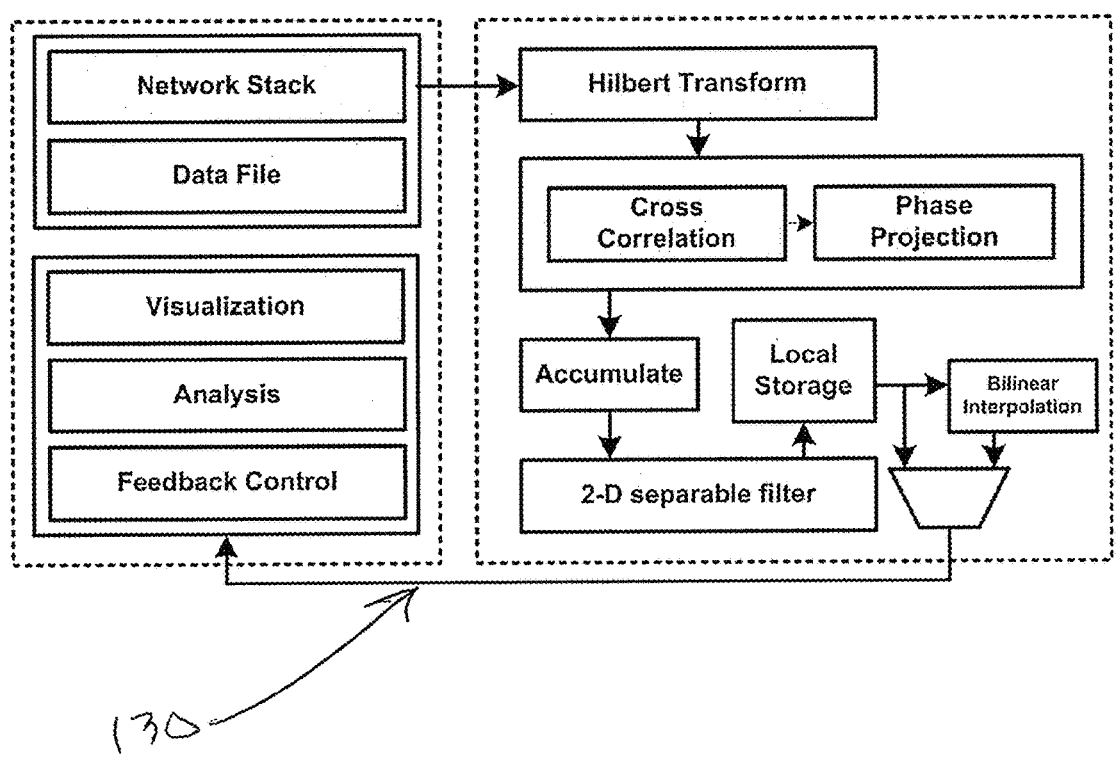
FIG. 4 is a block diagram of one exemplary GPU implementation of an imaging system such as shown in FIG. 3.

As shown in FIG. 4, M2D mode imaging may be enabled by creating a powerful pipelined execution/flow program architecture capable of employing a variety of computational resources for real-time implementation. In addition, the program architecture may allow the user to invoke additional computational resources available on the computer (or generally on the Internet) to achieve other computational tasks. The results from these computations can be integrated seamlessly with the program. For example, the beamformed RF echo data may be transferred in real time through a Gigabit interface to allow real-time 2D axial strain computations using GPU (or FPGA) using 1D speckle tracking. However, the beamformed RF data is available for additional processing using, for example, a pre-installed MATLAB engine. The MATLAB results can be imported back seamlessly to the M2D mode imaging program with minimum latency (e.g., after the completion of the MATLAB calculations). This capability may allow us to perform real-time 2D speckle tracking to enable strain and shear strain in the vicinity of the vessel wall, e.g., heavy-duty MATLAB-based calculations are performed on a small RoI allowing for their incorporation in real time. In at least one embodiment, true 2D speckle tracking approaches may be implemented in real time as is currently the case with 1D speckle tracking. In this way, a pipelined program execution architecture may be implemented to support M2D imaging which allows us to reap the benefits of powerful computational tools for the analysis of the vessel walls in quasi real-time.

The high frame rate M2D mode preserves the correlation to produce well-behaved 2D displacement/velocity profiles to allow for robust strain computation. High quality 2D (+time) strain and shear strain fields produce views of the vessel wall boundaries on both sides of the vessel in the axial view. Further, they may also produce better definition of the wall in the lateral direction in the cross-sectional view. This may allow for measurements of wall thickening, an early sign of atherosclerosis.

Still further, the high quality 2D (+time; i.e., over time) strain and shear strain will allow for tissue property measurements within the vessel wall, e.g. stiffness. Such tissue property measurements will allow for the characterization of the disease state and, given the high resolution, the plaque architecture (e.g., base, lipid core, and fibrous or calcified cap). Therapy or treatments may be delivered based on such information or such information may be used during the delivery of such therapy (e.g., high intensity focused ultrasound treatments that target the base of the plaque without damage to the cap or even the lipid core, continual determination of the response of tissue to therapy, such as between doses of high intensity focused ultrasound, etc.).

Figure 3:
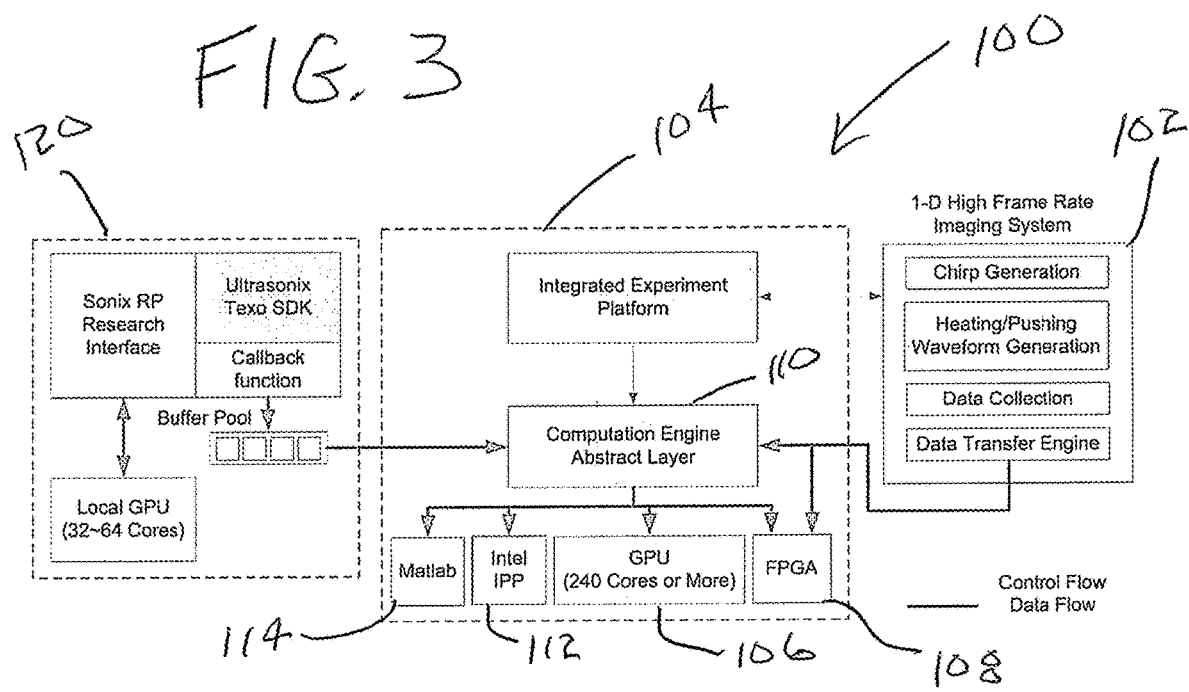
FIG. 3 is a block diagram of one exemplary embodiment of an imaging system shown generally in FIG. 1.

The pulse-echo data may be provided using any imaging system (e.g., the imaging system 10 of FIG. 1), although one or more imaging systems may be advantageous over others. In one or more embodiments, the data acquisition may be performed by an imaging system 100 such as shown in FIGS. 3 and 4. For example, as shown in FIG. 3, the imaging system 100 may be used to acquire and perform real-time processing of such acquired data. The imaging system 100 may include an ultrasound scanner 102 (e.g., a Sonix RP (Ultrasonix, Canada)) loaded with a program used for high frame rate pulse-echo data collection. The ultrasound scanner may include features such as chirp generation, waveform generation, data collection, and data transfer capabilities.

As shown in the exemplary embodiment, collected data may be streamlined to a controller PC 104 through, for example, Gigabit Ethernet for real-time data processing. The data processing computer 104 can handle the intensive computations required by high-resolution (both spatial and temporal) speckle tracking and separable 2-D post-filtering by utilizing a many-core graphics processing unit 106 (e.g., GPU; nVIDIA, Santa Clara, Calif.). The ultrasound scanner 102 may operate in B mode for image guidance (e.g., producing a B-mode image) and in M2D mode for high-frame-rate data collection. The M2D mode achieves high-frame-rate imaging by limiting the number of scan lines to the region of interest (ROI), as defined by the user. M2D data may be used for speckle tracking. For example, in one embodiment, M2D-mode acquisition with 10 A lines per frame at 1000 fps may be performed. For example, a linear array probe (e.g., LA14-5/38) may be used for data collection at a frame rate of 1000 fps in M2D mode by limiting the number of scan lines to 10 and the imaging range to 40 mm. In one or more embodiments with coded excitation, M2D-mode may collect data at frame rates from 2000 to 5000 frames per second or more.

In the embodiment shown in FIG. 3, high intensity focused ultrasound (HIFU) is also possible (e.g., for generating ultrasound for treatment or subtherapeutic mechanical and/or thermal effects). As such, a Virtex2Pro (Xilinx, CA) field-programmable gate array (FPGA) board 108 is dedicated for HIFU source and synchronized frame trigger generation. This implementation allows an interference-free data collection by briefly silencing the HIFU generator while pulse-echo imaging is active.

Speckle tracking used for imaging herein relies on accurate estimation of incremental frame-to-frame time shifts, which are typically much smaller than RF-echo sampling period. In one embodiment, a 2-D complex correlation of two subsequent frames of pulse-echo data is carried out. The real-time data processing engine 110 is based on a GPU 106 with a large number of cores (e.g., a GTX285 GPU with 240 processing cores and designed to take full advantage of its highly parallel architecture). Implementation of real-time processing is supplemented with Integrated Performance Primitives (Intel) and Matlab tools 112, 114. Further, a research interface system 120 is provided for operator control.

FIG. 4 shows an exemplary block diagram of a GPU-based implementation 130 for an imaging system, such as shown in FIG. 3. In one embodiment, for each processing stage, fine-grained partition is performed for the algorithm in a data-independent manner so that all 240 processors are working efficiently on individual blocks of data.

For example, FIG. 4 shows one exemplary embodiment of a real-time signal processing chain of beamformed ultrasound data for strain imaging (e.g., shown for 1D, but which can be generalized to 2D or 3D). The real-time speckle tracking is performed in the axial direction, but axial strain and axial shear strain can be performed in real-time as a first step to identify the vessel boundaries (e.g., this has been tested in vivo on vessels of various diameters (~1 mm in rat) and (~4 mm in swine)). The 2D strain calculations can be performed in a region-of-interest (RoI) around the identified blood vessel. Axial and lateral strains and corresponding shear strains can be calculated in real-time following this step. Furthermore, direct estimation of strains and shear strains in the immediate vicinity of the vessel wall may be provided. For both 1D and 2D versions of the strain calculations, additional processing in the time direction will further define the vessel boundaries and the internal boundaries of the wall. For example, in the context of imaging atherosclerosis, this may yield the internal composition of the plaque.

As shown in FIG. 4, on the CPU side, data can be come from Network Stack (e.g., experimental mode, where data is streamlined from SonixRP scanner) or Data File (e.g., review mode). The processed result can be visualized with a designed UI system (OpenGL based) or exposed to other commercial software for further analysis (e.g., Matlab). The result can be also used in feedback control for real-time temperature control.

On the GPU side, FIG. 4 shows a GPU-based implementation of the algorithm described in (see, e.g., Simon, et al., "Two-Dimensional Temperature Estimation Using Diagnostic Ultrasound," IEEE Transactions on Ultrasonics, Ferroelectronics, and Frequency Control, vol. 45, no. 4, pp. 1088-1099, July 1998). The various blocks shown in FIG. 4 have at least the following functionality: Hilbert transform: computes the analytic signal of the RF echo using an FIR Hilbert Transformer; Cross correlation/Phase projection/Accumulate: implements 1D version of speckle tracking; 2D Separable Filter: allows temperature estimation (e.g., thermal strain computation); Bilinear Interpolation: provides hardware accelerated interpolation for data visualization; and Local Storage: provides data management in GPU domain.

In other words, in one or more embodiments, a system for vascular imaging is provided herein that includes one or more ultrasound transducers (e.g., wherein the one or more transducers are configured to deliver ultrasound energy to a vascular region resulting in pulse-echo data therefrom) and processing apparatus (e.g., including one or more programs executable by one or more processors of the system to perform one or more functions thereof and as described herein, such as control of data frame acquisition, speckle tracking, visualization, image generation, characteristic identification, etc.).

In other words, the processing apparatus (e.g., GPU, CPU, etc.) may be configured (e.g., operate under control of one or more programs) to, for example, control the capture of pulse-echo data at a frame rate such that measured displacement of a vessel wall defining at least one portion of a blood vessel in the vascular region and measured average blood flow through the at least one portion of the blood vessel have a quasi-periodic profile over time to allow motion tracking of both the vessel wall and the blood flow simultaneously; generate strain and shear strain image data for the region in which the at least one portion of the vessel is located using speckle tracking; and identify at least one vascular characteristic of the vascular region in which at least one portion of a blood vessel is located based on the strain and shear strain image data (e.g., wherein the at least one vascular characteristic comprises at least one of a flow characteristic associated with flow through the blood vessel, a structural characteristic associated with the blood vessel, and a hemodynamic characteristic associated with the blood vessel).

Further, for example, processing apparatus may be configured to use speckle tracking of one or more speckle regions of the vascular region in which at least one portion of the blood vessel is located to track motion of both the vessel wall defining the at least one portion of the blood vessel and the blood flow through the at least one portion of the blood vessel (e.g., wherein the pulse-echo data is captured at a frame rate such that displacement of the vessel wall defining the at least one portion of the blood vessel and blood flow through the at least one portion of the blood vessel are measurable simultaneously within a same periodic cycle corresponding to a cardiac pulse cycle and/or identify at least one vascular characteristic of the vascular region in which the at least one portion of the blood vessel is located based on the simultaneously measured displacement of the vessel wall and average blood flow. Further, for example, the processing apparatus is further operable (e.g., by executing one or more programs) to generate strain and shear strain image data for the region in which the at least one portion of the vessel is located using the speckle tracking (e.g., wherein the speckle tracking includes using multi-dimensional correlation of sampled pulse-echo data of the one or more speckle regions undergoing deformation in the region in which the at least one portion of a blood vessel is located, wherein the multi-dimensional correlation comprises determining a cross-correlation peak for the sampled pulse-echo data based on phase and magnitude gradients of the cross-correlated sampled pulse-echo data).

As shown in FIGS. 5A-5D, in one or more embodiments, the frame rate at which pulse echo data is acquired should be at least greater than 100 fps, and even greater than 200 fps. In at least one embodiment, the frame rate is greater than 300 fps. The frame rate should be sufficiently high for reliable motion tracking in both tissue and blood synchronously (e.g., such that measurements relating to the same are relevant to the same time frame or periodic cycle). For example, in one embodiment, the M2D mode allows for providing a high frame rate while maintaining the correlation at high levels to produce smooth and contiguous displacement/velocity fields (e.g., displacement of tissue, motion of blood flow) to allow for robust strain and shear strain determinations.

Figure 5A:
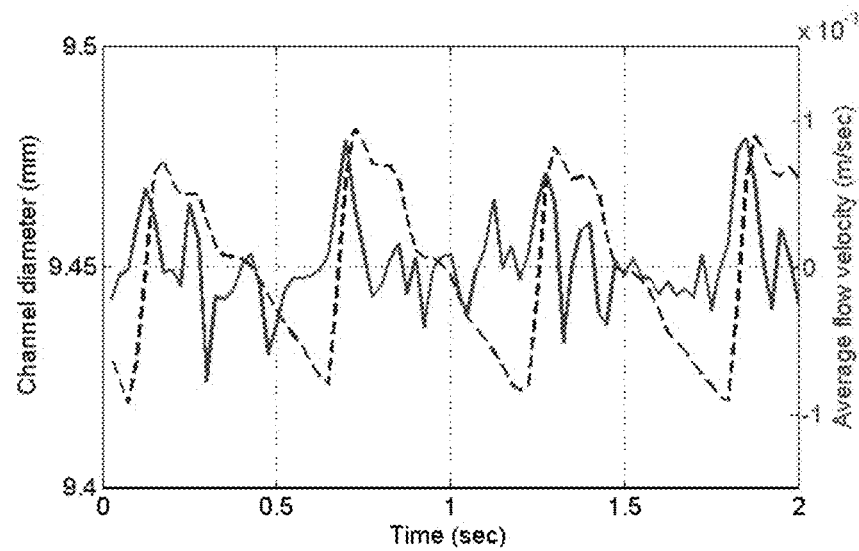
FIG. 5A-5D provides exemplary graphs showing channel diameter and average flow velocity over time for image data captured at various frame rates.
Figure 5B:
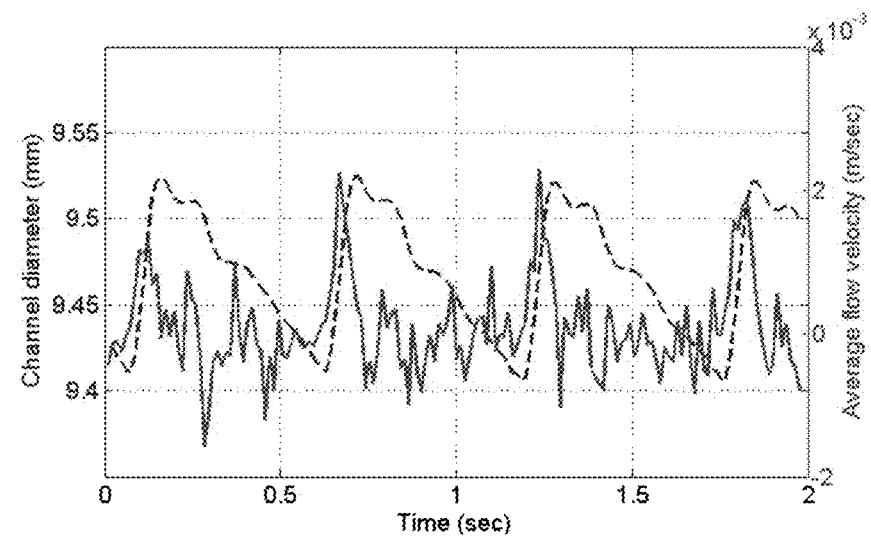
Figure 5C:
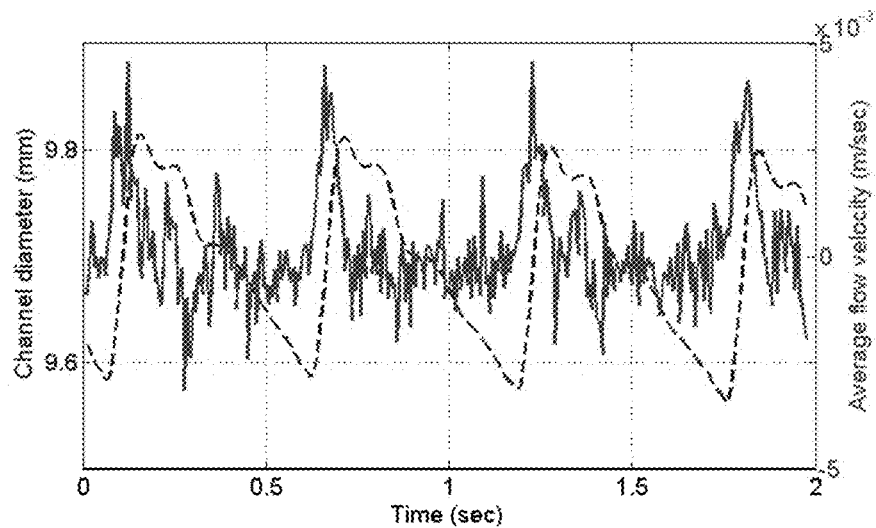
Figure 5D:
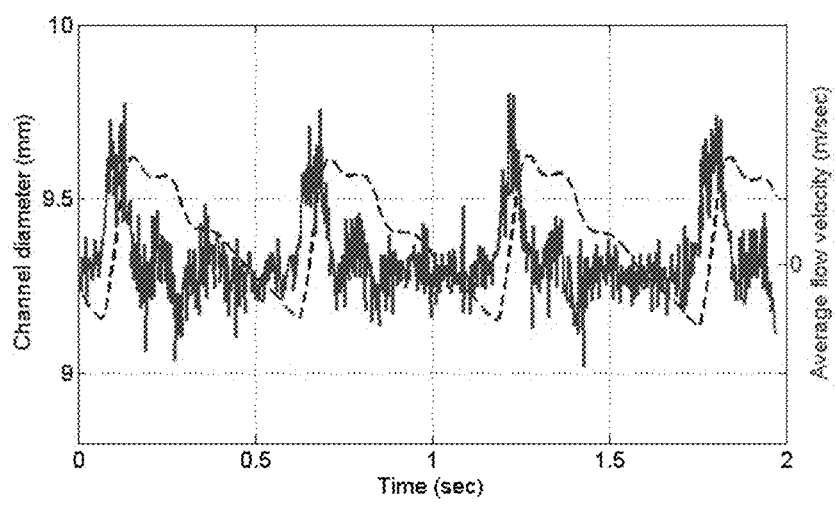

The frame rate for acquiring pulse-echo data should be adequate to provide displacement fields in both flow and tissue that are well-behaved. In one embodiment, such well-behaved displacement can be identified by the measurements of channel diameter related to tracking of tissue displacement (e.g., vessel wall displacement or motion) and average flow velocity related to the tracking of flow through the vessel (e.g., tracking of blood flow through the blood vessel) over time. As such, FIGS. 5A-5D show graphs of both the tracking of flow in a vessel (e.g., represented by the change of average flow velocity shown in solid lines) as well as the tracking of vessel tissue displacement (e.g., represented by change in channel diameter over time shown by dashed lines) for multiple frame rates. FIG. 5A shows determinations for a frame rate of 40 fps; FIG. 5B shows determinations for a frame rate of 81 fps; FIG. 5C shows determinations for a frame rate of 162 fps; and FIG. 5D shows determinations for a frame rate of 325 fps.

It is clear from FIGS. 5A and 5B, that such low frame rates (e.g., less than 100 fps) do not produce measured displacement of the vessel wall defining a blood vessel and measured average blood flow through the blood vessel which are well behaved. In other words, measurements of flow and tissue displacement (e.g., vessel wall displacement) could not be accurately measured simultaneously. For example, as clearly shown in FIGS. 5A and 5B, the blood flow is shown to be rather random throughout a periodic cycle of the displacement of the vessel wall represented by the channel diameter information (e.g., from peak to peak of the vessel wall displacement). In other words, such blood flow data is ridden with artifacts making an accurate flow determination difficult during the cycle. Even the vessel wall displacement information appears to include some artifacts.

However, discernible from FIGS. 5C and 5D, at higher frame rates (e.g., greater than 100 fps) the measured displacement of the vessel wall defining a blood vessel and measured average blood flow through the blood vessel are well behaved such that measurements of flow and tissue displacement (e.g., vessel wall displacement) could be accurately measured synchronously (e.g., corresponding to the same time). For example, as clearly shown in FIGS. 5C and 5D, the blood flow is shown to be much less random throughout a periodic cycle of the displacement of the vessel wall represented by the channel diameter information (e.g., from peak to peak of the vessel wall displacement). In other words, the measured displacement of the vessel wall defining a blood vessel and measured average blood flow through the blood vessel have a quasi-periodic profile over time which allows motion tracking of both the vessel wall and the blood flow simultaneously. Note the strong peaks for both the channel diameter and average flow velocity within the same periodic cycle (e.g., corresponding to the cardiac cycle).

As used herein, the term quasi-periodic profile is meant to reflect a profile that is substantially consistent over periodic cycles in the form of a regularized pattern, even though there will be some variation on a frame to frame basis, e.g., periodic cycles corresponding to cardiac cycles. For example, such a quasi-periodic profile for flow velocity may include strong peaks during each cycle indicating maximum flow followed by flow measurements that indicate little or no flow during the remainder of the cycle. Further, for example, such a quasi-periodic profile for channel diameter may include strong peaks during each cycle indicating maximum displacement of the vessel wall followed by measurements that indicate a relaxation of the vessel to a normal state during the remainder of the cycle. Such a frame rate that results in a quasi-periodic profile allows for tracking of flow and vessel displacement simultaneously, or in other words, synchronously with each other (e.g., in phase with each other).

The frame rate may vary depending on various factors. For example, the frame rate may be based on the vessel structure (e.g., carotid artery versus peripheral vein), timing of the periodic flow through the vessel (e.g., pulse cycle length), motion of the vessel structure (e.g., time for vessel to relax to normal); depth of the target vessel (e.g., deeper vessels may be imaged at lower frame rates), use of coded excitation (e.g., coded excitation may allow for increased frame rates), and the f-number of imaging focus (e.g., higher f-numbers may result in reduced lateral resolution), etc.

Still further, in one or more embodiments, higher frame rates may be accomplished when coded excitation ultrasound is used. Such coded excitation ultrasound is described, for example, in the literature and will not be discussed in detail herein. For example, one or more illustrative examples of coded excitation ultrasound which may be used in combination with the imaging method and/or systems described herein are provided in Shen et al., "A New Coded-Excitation Ultrasound Imaging System—Part I: Basic Principles," *IEEE Transactions on Ultrasonics, Ferroelectrics, and Frequency Control*, vol. 43, no. 1, pp. 131-140, January 1996); Shen et al., "A New Coded-Excitation Ultrasound Imaging System—Part II: Operator Design," *IEEE Transactions on Ultrasonics, Ferroelectrics, and Frequency Control*, vol. 43, no. 1, pp. 141-148, January 1996); and Shen et al., "Filter-Based Coded-Excitation System for High-Speed Ultrasound Imaging," *IEEE Transactions on Medical Imaging*, vol. 17, no. 6, pp. 923-934, December 1998), which are all incorporated herein by reference.

In one or more embodiments, the frame rate may be greater than 100 fps, greater than 200 fps, greater than 300 fps, greater than 500 fps, greater than 1000 fps, and even greater than 5000 fps. In other embodiments, the frame rate may be less than 5000 fps, less than 4000 fps, less than 3000 fps, less than 2000 fps, less than 1000 fps, less than 600 fps, less than 500 fps, less than 400 fps, less than 300 fps, or less than 200 fps. In at least one embodiment, the frame rate is within the range of 100 fps to 5000 fps.

As shown in the imaging method 30 in FIG. 2, speckle tracking is applied to the pulse-echo data (block 34). For example, strain and shear strain image data for the region in which at least one portion of the vessel is located may be generated using speckle tracking. In one or more embodiments, the speckle tracking may include using multi-dimensional correlation of sampled pulse-echo data of one or more speckle regions (e.g., windows) undergoing deformation in the region in which the at least one portion of a blood vessel is located. The multi-dimensional correlation may include determining a cross-correlation peak for the sampled pulse-echo data based on phase and magnitude gradients of the cross-correlated sampled pulse-echo data.

Such generation of strain and shear strain image data allows for the identification of at least one vascular characteristic of the region in which at least one portion of a blood vessel is located (block 36) (e.g., a flow characteristic associated with flow through the blood vessel, a structural characteristic associated with the blood vessel, a hemodynamic characteristic associated with the blood vessel, etc.). One or more types of strain and shear strain image data may be used and/or visualized to identify such vascular characteristics.

Strain calculations include performing band-limited gradient calculations on the 2D (or 3D) displacement fields obtained using speckle tracking (in 2D or 3D). Real-time speckle tracking on full image sizes (i.e., for every pixel of the RF echo data) may be achievable in the axial direction. 2D and 3D speckle tracking may be achieved in real time in a region of interest around the blood vessel. The strains and shear strains can be overlaid on B-mode or other ultrasound imaging formats. For example, information regarding such calculations are also found in Liu et al., "Real-Time 2-D Temperature Imaging Using Ultrasound," *IEEE Transac-* tions on Biomedical Engineering, vol. 57, no. 1, pp. 12-16 (January 2010), which is hereby incorporated by reference herein.

For example, generation of strain and shear strain image data for the region in which the at least one portion of the vessel is located using speckle tracking may include generation of at least one of axial strain and/or axial shear strain image data (e.g., axial relating to the axis through the vessel being imaged). Further, such generation of strain and shear strain image data may include generation of lateral strain and/or lateral shear strain image data. Such data may be visualized, for example, in both longitudinal views (e.g., along the blood vessel) or cross-section views (e.g., orthogonal to the axis of the blood vessel), as further provided herein.

For example, one or more types of strain and shear strain image data may be used and/or visualized to identify one or more vessel wall boundaries, including the vessel wall boundaries around the entire blood vessel (e.g., such boundaries may be visualized in cross-section and/or measured about the entire blood vessel). One or more other vascular characteristics may be identified, measured or calculated therefrom, such as tissue property within the one or more vessel wall boundaries, one or more portions of a plaque architecture adjacent the one or more vessel wall boundaries, and/or one or more hemodynamic measurements based on both the motion tracking of the vessel wall and the blood flow simultaneously.

Certain types of strain and shear strain image data may be more beneficial for imaging one or more portions of the blood vessel and flow therethrough than others. For example, axial strain image data may be beneficial in identifying a first set of opposing wall boundaries (e.g., on opposite sides of the vessel) while the axial shear strain image data may be beneficial in identifying a second set of opposing wall boundaries (e.g., on opposite sides of the vessel) such that the boundaries of the entire vessel (e.g., discernible in cross-section) can be identified. Further, the same is generally the case for lateral strain and lateral shear strain. Further, for example, the lateral shear strain may be beneficial in providing wall shear stress data (e.g., used for identification of possible plaque formation).

Further, for example, shear strain images further define the vessel walls, not only the proximal and distal walls, but also the side walls, which are hard to see on conventional ultrasound. (2D/3D+Time) calculations may also be used to refine the detection of the wall boundaries as a function of time during the heart cycle.

The speckle tracking applied to the pulse-echo data (block 34) may include using any multi-dimensional correlation of sampled pulse-echo data of one or more speckle regions (i.e., windows being tracked). For example, two-dimensional correlation of sampled pulse-echo data of one or more speckle regions may be used, as well as other multi-dimensional correlation techniques.

In one embodiment, for example, speckle tracking is performed as described in E. S. Ebbini, "Phase-coupled two-dimensional speckle tracking algorithm," *IEEE Trans. Ultrason., Ferroelect., Freq. Contr.*, vol. 53, no. 5, pp. 972-990, May 2006 (hereinafter "Ebbini 2006"), which is incorporated herein by reference. For example, in general, such speckle tracking includes coarsely searching the magnitude of the sampled pulse-echo data in a lateral and axial direction to locate a vicinity of the cross-correlation peak within the cross-correlated sampled pulse-echo data; determining, within the vicinity of the cross-correlation peak, at least two opposing gradient vectors in proximity to the cross-correlation peak; determining, within the vicinity of the cross-correlation peak, a zero-phase line of the cross-correlated sampled pulse-echo data; and using the at least two opposing gradient vectors in proximity to the cross-correlation peak and the zero-phase line to estimate the cross-correlation peak.

More specifically, as described in Ebbini (2006), a two-dimensional (2-D) speckle tracking method for displacement estimation based on the gradients of the magnitude and phase of 2-D complex correlation in a search region is provided. This approach couples the phase and magnitude gradients near the correlation peak to determine its coordinates with subsample accuracy in both axial and lateral directions. This is achieved with a minimum level of lateral interpolation determined from the angles between the magnitude and phase gradient vectors on the sampled (laterally interpolated) 2-D cross-correlation grid. One result behind this algorithm is that the magnitude gradient vectors' final approach to the true peak is orthogonal to the zero-phase contour. This leads to a 2-D robust projection on the zero-phase contour that results in subsample accuracy at interpolation levels well below those needed. Further, the approach includes a robust fast search algorithm that allows the localization of the true peak without the need for exhaustive search.

In other words, the speckle tracking uses the phase of the 2-D complex cross correlation for robust and efficient estimation of displacement from speckle data. This speckle tracking method finds the true peak of the 2-D complex cross correlation as a constrained optimization problem. The objective of this optimization problem is to find the coordinates of the axial and lateral lags at the true peak of the 2-D complex cross correlation subject to the zero-phase constraint. The basis for this formulation is shown mathematically from the inverse of the Fourier transform of the 2-D cross spectrum near the true correlation peak. This geometric approach finds both the axial and lateral displacement estimates with subsample accuracy. The method is based on the fact that the gradient vectors of the magnitude of the 2-D cross correlation approach the true peak along the orthogonal to the zero-phase contour. Knowing that the zero-phase contour also passes through the true peak, it is possible to locate this peak simply by finding the point on this contour at which the magnitude gradient vectors are orthogonal, provided these vectors originate from a grid point that is sufficiently close to the peak. One feature of this algorithm is that interpolation of the complex cross correlation is used at a minimum level that allows for a valid projection to be made. Therefore, the algorithm is computationally efficient in terms of determining the level of interpolation needed for subsample accuracy from the properties of the underlying 2-D, cross-correlation function, not from the desired lateral resolution.

The following is a mathematical basis for correlation-based 2-D speckle tracking and relates it to a 2-D cross spectrum approach. Thereafter, two implementations of a phase-coupled 2-D speckle tracking algorithm are then provided.

Let $s(x, z, t_0)$ be the analytic ultrasonic signal received from a 2-D region (e.g., speckle region or window) at time $t_0$ with spatial coordinates x and z representing the lateral and axial directions, respectively. The received signal model assumes a linear space-invariant imaging system with rectangular sampling (e.g., linear array). After undergoing translation $d_x$ and $d_z$ (respectively in the x and z directions), the received signal at time, $t_1$, $s(x, z, t_1) = s(x-d_x, z-d_x, t_0)$ has a 2-D Fourier transform:

$$S(k_x, k_z, t_1) = S(k_x, k_z, t_0)e^{-j(k_c d_{sc} + k_z d_y)}, \quad (1)$$

where $k_x$ and $k_z$ are the spatial frequency variables (in rad/m) in the x and z directions, respectively. The 2-D cross spectrum is given by:

$$\Gamma_{12}(k_x, k_z) = S(k_x, k_z, t_1)S^*(k_x, k_z, t_0) \quad (2)$$
$$= |S(k_x, k_z, t_0)|^2 e^{-j(k_x d_x + k_z d_z)}.$$

Motivated by this equation, one investigator developed an algorithm based on the 2-D cross spectrum for estimation of fine displacement in both the axial and lateral directions.

An iterative weighted least squares approach to estimate the slopes of the axial and lateral frequency components has been proposed. However, a more efficient solution to this problem can be obtained by finding the true peak of the 2-D cross-correlation function, given by (3) and (4), $$\gamma_{12}(l_x, l_z) = \frac{1}{4\pi^2}\int_{-\infty}^{\infty}\int_{-\infty}^{\infty}\Gamma_{12}(k_x, k_z)e^{j(k_x l_x + k_z l_z)}dk_x dk_z \quad (3)$$
$$= \frac{1}{4\pi^2}\int_{-\infty}^{\infty}\int_{-\infty}^{\infty}|S(k_x, k_z, t_0)|^2 \times$$
$$e^{j[k_x(l_x - d_x) + k_z(l_z - d_z)]}dk_x dk_z$$
$$= \gamma_{11}(l_x - d_x, l_y - d_z), \quad (4)$$

where $l_x$ and $l_z$ are the lags in the x and z directions, respectively. This function peaks at lag values equal to the shift values in both the axial and lateral directions. This result drives all correlation-based, 2-D displacement tracking methods. However, with the use of sampled correlation functions due to the discrete nature of the RF data collection, the true correlation peak must be found with subsample accuracy. This is especially true for the lateral displacement estimation in which the sampling interval (spacing between A-lines) is on the order of 10 times the axial sampling interval.

Insight into this problem can be obtained by evaluating the cross-correlation function in the vicinity of the true peak where $k_x(l_x - d_x) \approx 0$ and $k_z(l_z - d_z) \approx 0$, from (3):

$$\gamma_{12}(l_x, l_z) \approx \frac{1}{4\pi^2}\int_{-\infty}^{\infty}\int_{-\infty}^{\infty}|S(k_x, k_z, t_0)|^2(1 + j[k_x(l_x - d_x) + k_z(l_z - d_z)])dk_x dk_z \quad (5)$$
$$= \gamma_{11}(0, 0) + j[M_{xz}(l_x - d_x) + M_{zx}(l_z - d_z)],$$

where:

$$M_{xz} = \frac{1}{4\pi^2}\int_{-\infty}^{\infty}\int_{-\infty}^{\infty}|S(k_x, k_z, t_0)|^2 k_x dk_x dk_z, \quad (6)$$

$$M_{zx} = \frac{1}{4\pi^2}\int_{-\infty}^{\infty}\int_{-\infty}^{\infty}|S(k_x, k_z, t_0)|^2 k_z dk_x dk_z. \quad (7)$$

The factor $M_{xz}$ is related to the mean lateral frequency of the 2-D auto spectrum.

Similarly, the factor $M_{zx}$ is related to the mean axial frequency of the 2-D auto spectrum. Due to the fact that the axial component in many coherent imaging systems has a carrier and that the complex envelope is used, $|M_{zx}|\gg 0$. This modulation property does not exist for the lateral factor $M_{xz}$, and its magnitude is generally small. It is important to note, however, that in a speckle environment, $\oplus M_{xz}\oplus \neq 0$ (typically $|M_{zx}|\gg|M_{xz}|$). The result in (5) can be seen as a generalization of a 1-D speckle tracking case in which the slope of the phase curve is equal to the center frequency of the (analytic) echo signal [8]. In fact, expressing (4) in vector form (and including the quadratic phase term in the Taylor series expansion of the exponential), we get:

$$\gamma_{12}(l) = \frac{1}{4\pi^2}\int_{-\infty}^{\infty}\int_{-\infty}^{\infty}\Gamma_{12}(k)e^{jk'dx}dk \quad (8)$$
$$= \frac{1}{4\pi^2}\int_{-\infty}^{\infty}\int_{-\infty}^{\infty}|S(k, t_0)|^2 e^{jk'(l-dx)}dk$$
$$\approx \frac{1}{4\pi^2}\int_{-\infty}^{\infty}\int_{-\infty}^{\infty}|S(k, t_0)|^2(1 + jk'(l - dx) -$$
$$\frac{1}{2}(k'(l - dx))^2)dk$$
$$= \gamma_{11}(0, 0) - \frac{1}{2}(l - dx)'\begin{bmatrix}W_{xx} & W_{xz} \\ W_{zx} & W_{zz}\end{bmatrix}(l - dx) + \quad (9)$$
$$j[M_{xz} M_{zx}](l - dx),$$

where the elements $W_{xx}$, $W_{xz}$, $W_{zx}$, $W_{zz}$ are given by:

$$W_{xx} = \frac{1}{4\pi^2}\int_{-\infty}^{\infty}\int_{-\infty}^{\infty}|S(k_x, k_z, t_0)|^2 k_x^2 dk_x dk_z, \quad (10)$$

$$W_{zz} = \frac{1}{4\pi^2}\int_{-\infty}^{\infty}\int_{-\infty}^{\infty}|S(k_x, k_z, t_0)|^2 k_z^2 dk_x dk_z, \quad (11)$$

$$W_{xz} = W_{zx} \quad (12)$$
$$= \frac{1}{4\pi^2}\int_{-\infty}^{\infty}\int_{-\infty}^{\infty}|S(k_x, k_z, t_0)|^2 k_z k_x dk_x dk_z.$$

Note that $W_{xx}$ is related to the lateral frequency bandwidth of the imaging system. It is easy to see that $\gamma_{12}(d_x, d_z) = \gamma_{11}(0, 0) > \gamma_{12}(l_x, l_z) \forall (l_x, l_z) \neq (d_x, d_z)$. Also note that $\gamma_{12}(d_x, d_z)$ is real, which implies that the true peak of the 2-D cross correlation must lie on the zerophase contour defined by:

$$\angle\gamma_{12}(l_x, l_y) \approx M_{xz}(l_x - d_x) + M_{zx}(l_z - d_z), \quad (13)$$
$$= [M_{xz}M_{zx}](l - dx) = m'(l - dx).$$

However, based on the above approximation, the magnitude of the 2-D cross correlation is given by:

$$|\gamma_{12}(l)| = \sqrt{(\gamma_{11}(0,0) - (l-dx)'W(l-dx))^2 + (m'(l-dx))^2}, \quad (14)$$

for which the transpose of the gradient vector can be evaluated as shown in (15), which indicates that the gradient is identically zero at the true peak ($l = dx$) as expected.

$$\frac{\partial |\gamma_{12}(1)|}{\partial l} = \frac{-2(\gamma(0,0) - (1-dx)'W(1-dx))(1-dx)'W + (m'(1-dx))m'}{\sqrt{(\gamma_{11}(0,0) - (1-dx)'W(1-dx))^2 + (m'(1-dx))^2}} \quad (15)$$

Furthermore, the magnitude of the magnitude gradient near l=dx is proportional to the distance from the true peak, i.e., the closer the grid point to the true peak, the smaller the magnitude of the gradient. In addition, if the grid point is such that 1–dx is orthogonal to m (m'(1–dx)=0), then the magnitude gradient is orthogonal to m, and the true peak can be obtained by finding the intersection of the line along the magnitude gradient with the tangent to the zero phase contour. Of course, this is only valid when the grid point is sufficiently close to the true peak. This can be determined from the magnitude of the magnitude gradient on the grid. This result provides us with insight for approach to determine the true peak of the 2-D cross-correlation function from a grid of computed values around the peak. Specifically, by comparing the slope of the minimum magnitude gradient with the slope of the phase contour in the vicinity of the peak, one can determine whether the true peak is sufficiently close to the grid points to make a valid approximation.

This leads to algorithms as described herein for finding the true peak that are both robust and numerically efficient in the sense that interpolation is used at a minimum level to ensure the conditions of a valid projection onto the zero-phase contour. The formulation described herein also provides the basis for an optimization procedure of finding a point on a quadratic surface (magnitude of the 2-D cross correlation) subject to the zero-phase condition. This problem can be solved using the Lagrange multiplier method as described herein.

The above result can be easily extended to the case of affine transformation [13]:

$$s(x_1, t_1) = s(x_0(x_1), t_0), \quad (16)$$

where:

$$x_0 = Tx_1 - dx \quad (17)$$

$$\begin{bmatrix} x_1 \\ z_1 \end{bmatrix} = \begin{bmatrix} 1+e_{xx} & e_{xz} \\ e_{zx} & 1+e_{zz} \end{bmatrix} \begin{bmatrix} x_0 \\ z_0 \end{bmatrix} - \begin{bmatrix} dx \\ dz \end{bmatrix}, \quad (18)$$

which accounts for translation (dx), strain ($e_{xx}$ and $e_{zz}$), and shear strain ($e_{xz}$ and $e_{zx}$). In this case, we use the Fourier transform of the received signal at time $t_1$ in vector form:

$$S(k, t_1) = S(T'^{-1}k, t_0) e^{j(k^T {}^{-1}dx)} / |T|, \quad (19)$$

where T' is the transpose of T and |·| is the determinant of a matrix. Note that (19) is just a generalization of the scaled property of the Fourier transform in 1-D, which has previously been used in the analysis of decorrelation of ultrasonic echoes in the presence of strains. It is also consistent with the 2-D/3-D formulation shown in [5], which analyzes the combined effects of deformation and waveform warping on the variance of the displacement estimate.

It suggests that both axial and lateral strains can affect the displacement estimates based on phase matching alone. It also may provide an opportunity to directly (or iteratively) estimate the strains on the tissue region interrogated by the window. We note here that, in cases in which the strain parameters, $e_{xx}$, $e_{zz}$, $e_{xz}$, and $e_{zx}$, have non-negligible values, the zero-phase contour does not necessarily go through the true peak of the magnitude of the 2-D cross correlation. To illustrate this point, (19) can be written explicitly in terms of the shift and strain parameters as shown in (20), which shows that the scaling of the Fourier transform in the $k_x$ and $k_z$ coordinates is coupled through the shear strain parameters. Amplitude scaling leads to decorrelation effects previously reported for 1-D tracking. Furthermore, the estimated shift from the zero-phase contour is also coupled, i.e., a shift in the x direction contributes to the estimated shift in the z direction and vice versa (through the shear strain parameters). The simple result given by (5) is only approximately valid for infinitesimal strains within the tracking window. Fortunately, (20) provides a method to detect when the strain effects within the window are significant enough to affect the phase estimation.

$$S(k_x, k_z, t_1) = \frac{1}{|T|} S\left(\frac{(1+e_{zz})k_x - e_{zx}k_z}{|T|}, \frac{-e_{xz}k_x + (1+e_{xx})k_z}{|T|}, t_0\right) \cdot e^{-j\left(\frac{((1+e_{zz})dx - e_{xz}dz)k_x + ((1+e_{xx})dz - e_{zx}dx)k_z}{|T|}\right)} \quad (20)$$

In the speckle tracking method, one is interested in the use of phase-coupled approach in finding the true peak of the 2-D cross-correlation function when the tissue is undergoing displacement and/or infinitesimal strains. This can be considered a first step in estimating the displacement vectors needed in applications such as, for example, vector velocity estimation and elastography. Such applications may require displacement tracking based on the peak of the 2-D cross correlation as a common step, but they may differ in the deformation model parameters used. This can be done by implementing a post-processing step that extracts the deformation parameters from the shift estimation results obtained from finding the true peak of the 2-D cross correlation. Such post-processing depends on the specific problem to be determined.

An Exemplary Phase-Coupled 2-D, Speckle Tracking Algorithm

The steps of the exemplary speckle tracking algorithm are guided by the properties of the 2-D correlation of the speckle region undergoing motion and/or deformation. The magnitude of the 2-D correlation with the complex envelope has a well behaved peak with extent in axial and lateral directions proportional to the speckle cell size. The main idea is to use a fast search algorithm to find a correlation-based match within a search window (i.e., correlation values above a threshold). If the current search point is far from the correlation peak, a fast search can be used with axial and lateral steps on the order of one-half the extent of the correlation cell size in the axial and lateral directions. This allows the search to coarsely cover large regions without missing the true peak (if it exists). Once a match is found, the magnitude gradient of the cross correlation is used to find the peak cross correlation on the sampling grid (determined by the RF sampling frequency and spacing between the A-lines in the image). This is done by following a gradient ascent trajectory, which requires two to three correlation values to be computed for every point along the trajectory. Gradient search for the peak is very robust and efficient from any direction if search point is within the width of the correlation peak in the axial and lateral directions, e.g., within 3 dB from the peak. Once the grid-based correlation peak is found, a 3×3 correlation grid is calculated (centered at the peak). In the immediate vicinity of the correlation peak, the true peak can be determined from the magnitude gradient vectors and the zero-phase contour passing the true peak. From the 3×3 grid in the original sampling coordinates, a fine estimate of the true correlation peak is produced by coupling the phase of the 2-D cross correlation to the amplitude (gradients) in a way that will allow us to use (13).

Two exemplary approaches for obtaining the fine estimates are described in the following subsections.

A. Two-Dimensional Projection on the Zero-Phase Contour

This method interpolates the 3×3 grid near the true peak in the lateral lag direction by a sufficiently large factor (i.e., as small as possible) in order to estimate a magnitude gradient vector orthogonal to the zero-phase contour. The intersection of the magnitude gradient and the zerophase contour is the estimated true peak of the 2-D cross correlation.

The steps of this algorithm are outlined as follows.

Step 0: From the 2-D autocorrelation function at $t_0$, estimate the search step size $L_z$ and $L_x$ in the axial and lateral directions, directly. Typically, $L_z > L_x$ due to the finer sampling in the axial direction.

Step 1: Perform any fast search algorithm to find the vicinity of correlation peak (above a threshold) using $L_x$ and $L_z$ in a defined search region.

Step 2: Without any interpolation, compute the local magnitude gradient and move along the gradient ascent trajectory. This step stops when the peak point on the uninterpolated grid is reached.

Step 3: Once the maximum point on the uninterpolated grid is reached, compute cross-correlation values on 3×3 grid centered at the maximum. Interpolate the 3×3 grid laterally by a small factor (e.g., 8) and find the line equations for the two gradient vectors closest to the true peak, but pointing in opposite lateral directions. If this condition is not satisfied with the current interpolation factor, increase interpolation by two and repeat the test. If maximum interpolation factor is reached (e.g., 128) and correlation at the interpolated peak is below a threshold (e.g., 0.75) displacement estimate is declared invalid and assigned a value of NaN. Otherwise, proceed to Step 4.

Step 4: Find the line equations for the zero-phase line of the correlation function on the interpolated grid. The estimated true correlation peak is the point of intersection between the zero-phase line and the orthogonal line that passes through the point of intersection of the two maximum-slope lines from the magnitude gradient.

Figure 6A:
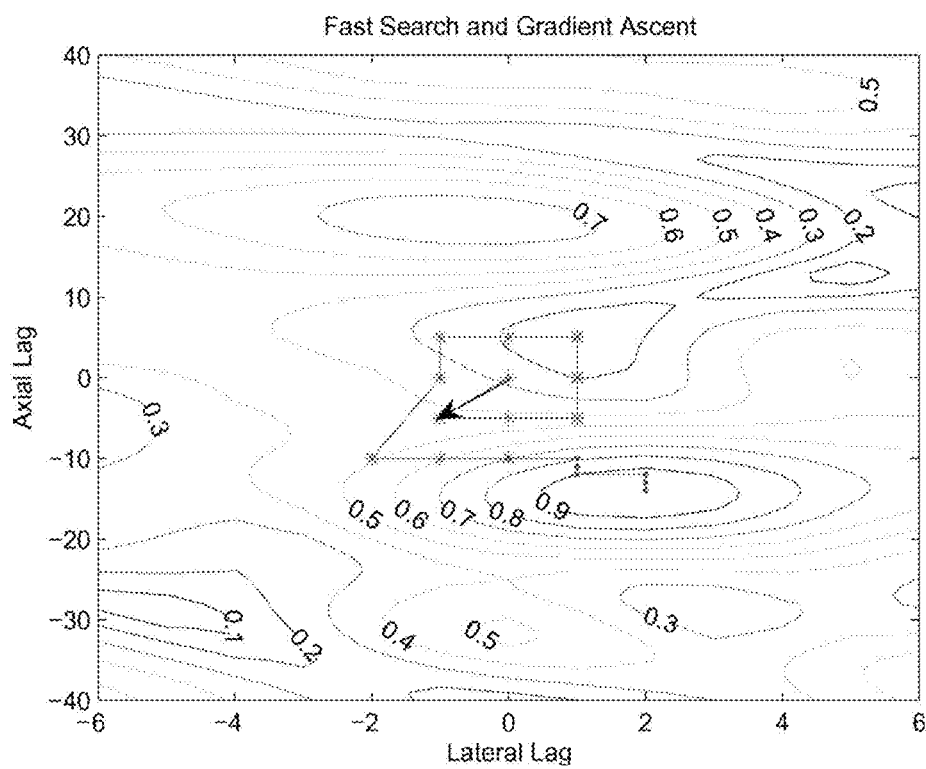
FIGS. 6A-6B shown graphs including contours of certain parameters of cross-correlations used to describe one exemplary embodiment of speckle tracking that may be used in an imaging method and/or system shown generally in FIGS. 1-2.

For illustration purposes, the search trajectory in FIG. 6A is based on $L_x=1$ and $L_z=5$ (from Step 0). FIG. 6A shows contours of the 2-D cross correlation with the search path shown [starting from (0,0) lag as indicated by the arrow]. The * indicates correlation lags tested by the fast-search algorithm and the • indicates lags tested by the gradient-ascent algorithm ($L_x=1$ and $L_z=5$). Note that the true correlation peak has a well behaved set of contours that distinguish it from several false peaks in the search region shown. Furthermore, the 0.7 contour extends by approximately 4 lateral lags and 10 axial lags (which justifies the choice of $L_x$ and $L_z$). Step 1 begins at lag (0,0) and tests the cross-correlation coefficient. If below the set threshold (0.65 in this case), it moves to the next point as indicated by the arrow (−1 lateral and −5 axial). If still below threshold, it tests correlation values along each pixel on the (predefined) trajectory. In this case, the predefined search trajectory is along rectangular counterclockwise loops (dimensions 2 $L_x*i+1 \times 2*L_z*i+1$ where i=0, 1, . . . , Imax is the loop number). The parameter $I_{max}$ defines the extent of the allowed search region to find a valid peak ($I_{max}=6$ for the search region shown in FIG. 6A).

In this search example, the eight lags on the first loop are tested, and no candidate peak is found (i.e., no correlation value >0.65). The algorithm jumps from the last point in the first loop (−1 lateral and 0 axial) to the first point in the second loop (−2 lateral and −10 axial) and moves counter clockwise along the lateral lag direction. This step stops once the threshold test is successful, i.e., correlation value at the current correlation lag above the chosen threshold. In FIG. 6A, this step stops at lateral lag 0 and axial lag −10 after a threshold of 0.65 was reached. Step 2 also is illustrated with the help of FIG. 6A. The • signs at (0, −10), (1, −10)(1, −11), (1, −12), (2, −12), (2, −13), (2, −14) are the grid points tested by the gradient ascent. The neighboring points of (2, −14) also are tested before declaring this point as the maximum point on the correlation grid.

Figure 6B:
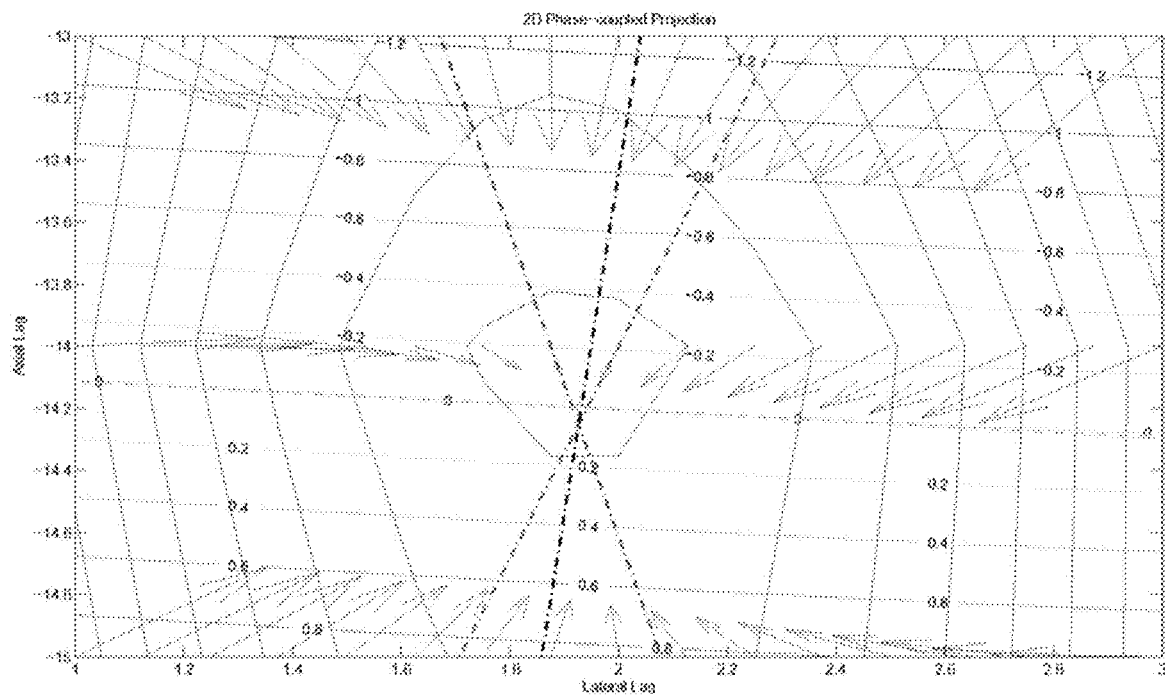

The final two steps of the algorithm may be illustrated with the help of FIG. 6B which shows the magnitude and phase contours of the interpolated 2-D cross correlation near the true peak. Further, FIG. 6B shows magnitude and phase contours of the 2-D cross correlation on the laterally-interpolated 3×3 grid in the vicinity of the correlation peak (between lags −13 and −15 axially and 1 and 3 laterally). The arrows represent the magnitude gradient vectors on the interpolated grid. Lateral interpolation by a factor of 16 is used in this case (with the interpolated grid points indicated by the arrow bases). The phase contours are labeled with phase values in radians and appear to be almost straight with a small tilt. The true peak is indicated by the open circle on the zero-phase line. The dash-dotted lines are the directions of the magnitude gradient vectors closest to the peak and the tangent and the orthogonal to the zero-phase line. In addition, one can see the magnitude gradient vectors pointing in the (general) direction of the true peak. An interpolation factor of 16 was used for this case between lateral lags 1 and 3 and axial lags −13 and −15 (i.e., centered at 2 lateral and −14 axial from Step 2). Four (thick dash-dotted) lines are drawn along the two closest magnitude gradient vectors, the tangent to the zero-phase line, and the orthogonal to the zero-phase passing through the point of intersection of the maximum-slope lines. The true correlation peak, indicated by the open circle, is the point of intersection of the latter with the zero-phase line.

The final step in the projection on zero-phase algorithm is an approximation of the magnitude gradient vector orthogonal to the zero-phase contour at the true peak. The approximation error depends on the level of interpolation used and can be controlled by using a lateral interpolation factor just enough to ensure that at least one of the two magnitude-gradient vectors used in the final approximation is not substantially parallel to the zero-phase contour near the true peak. In general, this condition is needed only when the axial shift is practically equal to integer multiple of the axial sampling interval. For example, in FIG. 6B one can see the magnitude gradient vectors at axial lag −14 approaching from the right are almost parallel to the zero-phase line. The interpolation factor of 16 used here was just enough to produce a valid projection. A valid projection is one in which the two magnitude gradient vectors closest to the peak intersect the tangent of the zero-phase line at points in which the tangent approximates the phase contour well. The key point here, however, is that the interpolation can be performed adaptively, thus minimizing any unnecessary calculations in the displacement estimation algorithm. In addition to the computational advantage of this approach, one can reduce or eliminate the error due to interpolation.

It should be noted that one or more different steps may be implemented in the method, and the specific steps provided herein are not take to be limiting on the disclosure. For example, the exemplary search algorithm may be implemented using one or more other digital signal processing approaches. Further, for example, for template matching, one can use the autocorrelation sequence in the vicinity of the (0,0) lag. A related issue is the declaration of an invalid estimate based on the correlation threshold in Step 3 and assigning a value of NaN. This can be thought of as a flag to be used in subsequent processing if necessary. For example, one may use an adaptive window size to maximize the composite signal-to-noise ratio (SNR). Alternatively, one may use an explicit deformation model similar to that described by (19).

Further, the present disclosure is not limited to use of 2D speckle tracking. For example, other multi-dimensional tracking methods, such as 3D speckle tracking methods may also be applicable in one or more embodiments herein.

B. Surface Polynomial Fit with Phase Constraints

The 2-D phase projection approach described above can be thought of as an efficient method for implementation of an optimization procedure for finding the true peak of the complex 2-D cross correlation. The peak finding problem can be cast as finding the coefficients of a polynomial fit to the surface of the magnitude of the 2-D cross correlation in the vicinity of the true peak. The nominal and interpolated contour plots shown in FIGS. 6A and 6B are obtained from actual imaging data and are representative of what can be expected from a standard imaging scanner. It is quite clear that the surface near the true correlation peak is well behaved and appears to be quadratic in the lx, lz space. A polynomial fit to this (smooth) surface is given by:

$$q(l_x, l_z) = al_x^2 + bl_z^2 + cl_x l_z + dl_x + el_z + f, \quad (21)$$

where $l_x$ and $l_z$ represent lateral and axial lags, respectively, and q is the magnitude of the 2-D, complex cross correlation in the vicinity of the true peak. It is possible to solve for the polynomial coefficients by minimizing the square error:

$$J(\theta) = \sum_{i=1}^{N} (q(l_{x_i}, l_{z_i}) - |\gamma_{12}(l_{x_i}, l_{z_i})|)^2, \quad (22)$$

where $\theta = [a, b, c, d, e, f]'$ and N is number of points on the grid (in this case N=9).

This amounts to solving the over-determined system of equations:

$$\hat{q} = A\theta \quad (23)$$

$$\begin{bmatrix} |\gamma_{12}(l_{x_1}, l_{z_1})| \\ |\gamma_{12}(l_{x_2}, l_{z_2})| \\ \vdots \\ |\gamma_{12}(l_{x_N}, l_{z_N})| \end{bmatrix} = \begin{bmatrix} l_{x_1}^2 & l_{z_1}^2 & l_{x_1}l_{z_1} & l_{x_1} & l_{z_1} & 1 \\ l_{x_2}^2 & l_{z_2}^2 & l_{x_2}l_{z_2} & l_{x_2} & l_{z_2} & 1 \\ \vdots & \vdots & \vdots & \vdots & \vdots & \vdots \\ l_{x_N}^2 & l_{z_N}^2 & l_{x_N}l_{z_N} & l_{x_N} & l_{z_N} & 1 \end{bmatrix} \begin{bmatrix} a \\ b \\ c \\ d \\ e \\ f \end{bmatrix}. \quad (24)$$

This results in:

$$J(\theta) = (\hat{q} - A\theta)'(\hat{q} - A\theta) \quad (25)$$

$$= \hat{q}'\hat{q} - 2\hat{q}A\theta + \theta'A'A\theta. \quad (26)$$

By taking the gradient of this quadratic function with respect to the real vector θ and equating to zero, we obtain the solution:

$$\hat{\theta} = (A'A)^{-1}A'\hat{q}, \quad (27)$$

which is valid when the matrix A is well conditioned. If this is not the case, then a regularized solution (e.g., using singular value decomposition) is sought [17]. Once the coefficients θ are obtained, it is a simple matter to obtain $l_{max}$ and $l_{max}$ by analytically evaluating the gradients:

$$\frac{\partial q}{\partial l_x} = 2al_x + cl_z + d, \quad (28)$$

$$\frac{\partial q}{\partial l_z} = cl_x + 2bl_z + e, \quad (29)$$

and solving the matrix equation:

$$\begin{bmatrix} l_{x_{max}} \\ l_{z_{max}} \end{bmatrix} = \begin{bmatrix} 2a & c \\ c & 2b \end{bmatrix}^{-1} \begin{bmatrix} -d \\ -e \end{bmatrix}. \quad (30)$$

However, this solution may amount to a form of interpolation based on magnitude only, which may result in unacceptably high levels of bias and variance in the estimation of the true correlation peak, especially in the axial direction. This is due to the almost flat nature of the surface described by q in the axial direction (axial extent of only ±1 lag samples). However, q typically has a distinct peak in the lateral direction, and the derivative in this direction yields a reliable estimate of the peak. It is known that the analytic nature of ultrasonic echo signal allows for high subsample accuracy in axial shift estimation by using complex cross correlation without interpolation. An improved solution may be obtained if the lateral estimate from surface fitting solution described by (30) with the axial estimate obtained from the analytic RF data.

Accounting for phase information in 2-D can be done easily by using (13) as a constraint in conjunction with an appropriate cost function (e.g., using the Lagrange multiplier method). To do this, we recognize that the polynomial fit function given in (21) is itself a quadratic cost function in $l_x$ and $l_z$. That is, one can rewrite (21) in the form:

$$q(l_x - dx_0, l_z - dz_0) = l'R1, \quad (31)$$

$$= l' \begin{bmatrix} a & \frac{c}{2} \\ \frac{c}{2} & b \end{bmatrix} 1,$$

where $dx_0$ and $dz_0$ are the coordinates of the center of the 3×3 grid in the vicinity of the true peak and $1 = [l_x - dx_0, l_z - dz_0]'$. The elements of R are obtained from the solution to least squares problem in (23). This can be shown by expanding the translated vector form in (31) and comparing with the coefficients of $l^2_x$, $l^2_z$ and $l_x l_z$ in (21). The optimization problem is to find the subsample shift vector $\delta l=[\delta_x, \delta_z]'$ (note that $l_{max}=[dx_0, dz_0]'+[\delta_x, \delta_z]'$) that minimizes (31) subject to the constraints:

m'm=1, which implies $m_x=M_{xz}/\sqrt{M_{xx}^2+M_{zz}^2}$ and $m_z=M_{zx}/\sqrt{M_{xz}^2+M_{zx}^2}$ $\delta l'm=\delta_x m_x+\delta_z m_z=0$.

The first constraint is just a normalization that is typically used in eigenvalue problems. The second constraint restricts the solution vector to be orthogonal to the zerophase line at the true peak (13). The elements of m are obtained from the center frequency values in (6) and (7).

The constraints above allow us to define a new cost function in terms of the Lagrange multipliers, $\lambda$ and $\mu$:

$J(\delta l)=\delta l'R\delta l-\lambda(\delta l'\delta l)+\mu \delta l'm.$  (32)

The solution to this problem can be obtained by taking the gradient of J with respect to $\delta l$:

$$\frac{\partial J}{\partial \delta 1} = 2R\delta 1 - 2\lambda \delta 1 + \mu m.$$  (33)

Multiplying by m' and solving for $$\mu = -2m'R\delta 1 - 2\lambda m'\delta 1$$  (34)

$$= -2m'R\delta 1,$$  (35)

where the orthogonality constraint was used to drop the second term in (34). Substituting $\mu$ back in (33), we obtain the eigenvalue problem:

$2R\delta l-2\lambda \delta l-2m'R\delta l=0$ $\Rightarrow (I-mm')R\delta l=\lambda \delta l.$  (36)

The solution to this eigenvalue problem is the eigenvector associated with the maximum eigenvalue of the matrix (I−mm')R. The Lagrange multiplier, $\lambda$, is the eigenvalue, which appropriately scales the eigenvector to give the true lag (at the true maximum). The projection matrix, (I−mm'), serves to align the solution obtained based on the magnitude-only method to be orthogonal to the observed slope of the zero-phase contour. Thus the coupling between the phase and magnitude characteristics for finding the true peak of the 2-D cross correlation is complete.

Various steps, routines, or processes may be implemented with the exemplary speckle tracking methods described herein (such as those described in Ebbini (2006)), that further assist in providing useful image data or enhancement of image data. For example, when performing speckle tracking of speckle regions in the region in which at least one portion of a blood vessel is located, if the speckle region (i.e., window or speckle cell) being tracked is partially within the vessel wall defining the at least one portion of the blood vessel and partially outside of the vessel wall (e.g., lying partially in the blood within the vessel or lying partially outside of the boundaries of the vessel wall), the speckle tracking process may be difficult to carry out or result in data that is inaccurate (e.g., difficult to cross correlate, etc.). As such, at least in one embodiment, once a vascular characteristic is identified or determined (e.g., the identification of one or more boundaries (or portions thereof) of the vessel based on speckle tracking), the vascular characteristic may be used in performing the speckle tracking method.

For example, one or more vessel wall boundaries may be identified based on the speckle tracking of one or more speckle regions. Once such boundaries are identified, they can be used in the speckle tracking process. In one or more embodiments, for example, a characteristic of the one or more speckle regions (e.g., location, size, shape, etc.) may be modified based on the at least one identified vascular characteristic (e.g., such as the identification of vessel wall boundaries). For example, the location of at least one of the one or more speckle regions being tracked may be modified (e.g., or any other characteristic of one or more speckle regions, such as size, or shape, may be modified) based on the one or more vessel wall boundaries identified (e.g., such that the speckle region being tracked is entirely within or outside of the vessel wall). In other words, if the speckle tracking process determines that a speckle region or window being tracked is partially within the vessel wall defining the at least one portion of the blood vessel and partially outside of the vessel wall (e.g., lying partially in the blood within the vessel or lying partially outside of the boundaries of the vessel wall), then the speckle region location may be modified or otherwise adjusted such the speckle region is entirely located within the vessel wall or outside of the vessel wall. Further, the size or shape (e.g., narrowness or width or length) of the speckle region tracked may be modified during the speckle tracking such that the speckle region is entirely located within the vessel wall or outside of the vessel wall, or provides quality estimates, e.g., of displacement. In other words the speckle region is modified such that it falls entirely outside the vessel wall, entirely within the vessel wall, or entirely within the blood, based on the one or more boundaries determined for the vessel (e.g., by prior speckle tracking and generation of strain and/or shear strain image data for the region in which the at least one portion of the vessel is located).

For example, generally, tracking windows are designed to optimize or achieve a tradeoff between spatial resolution (e.g., generally improved by reducing the window size) and reducing the variance of the displacement estimates (e.g., generally, by increasing the window size). For example, in one embodiment, for a uniform speckle region, the signal-to-noise (SNR) of the echo data, together with the transducer bandwidth, are the primary factors in selecting the window size. Furthermore, in the absence of severe deformation, windows are designed to be approximately square, i.e., approximately the same axial and lateral dimensions. Near the vessel wall, especially on the lumen side, many assumptions may be violated. High frame rate imaging (e.g., M2D mode imaging) is provided to mitigate some of these effects, but there may also be a need to account directly for deformations within the tracking window (e.g., part of the window being in the vessel and part in the blood leading to deformation issues). In such cases, one may apply adaptive window size and shape design or selection algorithms that will produce optimal estimates (e.g., best possible displacement estimate). The 2D phase-coupled algorithm provides feedback on the quality of the estimates (e.g., figures of merit). These figures of merit may be used in characterizing the quality of the estimate obtained, for example, using different windows with the same height, but different width and vice versa. As such, it is possible to run these windows in parallel and implement a voting scheme that selects the estimates with the highest figures of merit and reject or weigh down (e.g., apply a lower weighting factor) the estimates with lower figures of merit.

Still further, vessel wall echo reverberations may corrupt pulse-echo data received from the blood. As such, in one or more embodiments of speckle tracking of one or more speckle regions within the blood, the speckle tracking may remove echo components in the pulse-echo data due to reflection at the vessel wall when performing such speckle tracking of the pulse-echo data from the one or more speckle regions in the blood (e.g., using a dereverberation filter).

In other words, as described herein, various speckle tracking methods (e.g., two-dimensional speckle tracking methods) can be used to image tissue motion and deformations in the vicinity of blood vessels (e.g., for use in detecting and staging of vascular disease). However, in one or more embodiments, vessel wall echo reverberations may overwhelm the echoes (scattering) from the blood and result in loss of flow information in large regions within the vessel. One embodiment that may be used to correct for such reverberations includes use of a time-varying dereverberation inverse filter for echo data within the vessel (e.g., echo data from the blood). The design for such a filter may be influenced by the fact that the reverberation pattern varies significantly with the pulsatory motion of the vessel wall. Minute changes in the location/orientation of the vessel wall with respect to the imaging beam result in measurable changes in the speckle-specular echo mixture at the vessel wall and the observed periodicities in the reverberation pattern within the vessel. Therefore, a time-varying inverse filter may be used to remove the reverberation components appropriately during the heart cycle.

Speckle tracking (e.g., two-dimensional speckle tracking) can be used for the analysis of tissue motion and deformation, especially in vascular imaging applications. In addition to the direct measurements and/or characterization of the vessel dynamics, such speckle tracking may provide tissue displacement fields and underlying anatomical information suitable for important challenge areas such as computational fluid dynamics.

For example, as described herein, simultaneous estimation of tissue motion/deformation and blood flow vector velocity in a blood vessel (e.g., the human carotid artery) using pulse-echo diagnostic ultrasound can be performed (e.g., using phase-coupled two-dimensional speckle tracking which achieves subsample displacement estimation accuracy in both axial and lateral directions together with a high frame rate (e.g., 325 frames per second) M2D imaging mode both lateral flow velocity and wall motion can be estimated simultaneously thus providing pressure (through vessel diameter) and flow (through vector velocity)). Such measurements can provide the basis for hemodynamic computations that may be used in the assessment of vessel wall compliance, an important indicator of the health of the vessel as described herein. Further, as described herein, axial and lateral displacement fields are well-behaved and allow for strain and shear strain calculations in both tissue and blood. Together with anatomical image information, these velocity/strain fields may provide input for computational fluid dynamic models, which may allow for inverse calculations suitable for the assessment of the health of the vasculature and surrounding tissue (e.g. detection and staging of atherosclerosis).

One possible limitation of two-dimensional speckle tracking methods based on pulse-echo ultrasound is the reverberation components associated with strong specular reflectors. Reverberation produces clutter signal components that mix with back scattering components from regions distal to the specular reflector. This is significant in blood vessels where the scattering from blood is typically 30-40 dB below the specular reflection from the vessel wall. For applications where both the tissue motion and blood velocity vectors are important, however, the clutter due to reverberation from the region within the vessel walls should be minimized. An algorithm for dereverberation of pulse-echo ultrasound data to restore echoes from the blood scattering region prior to two-dimensional speckle tracking may be used to address such reverberations. Due to the changes in the scattering characteristics of the vessel wall during the different phases of the heart cycle, it is observed that the reverberation signal components are non-stationary, which indicates that a time-varying inverse filter for dereverberation may be needed. One possible filter design approach may utilize short-range correlation for the echo signal from the wall and the long-range correlation of the echo signal from the proximal wall and the vessel region. Periodicities in the correlation functions are attributed to the vessel wall architecture and multilayer tissue structure resulting in distinct specular components (e.g. adventia).

The following provides one or more implementations of dereverberation or examples testing the same. Such specific implementations or examples are not to be taken as being limiting to the present disclosure.

Exemplary Dereverberation Filtering Information

Data Acquisition for the example Dereverberation Filtering

A Sonix RP (Ultrasonix, Canada) ultrasound scanner loaded with a program used for M2D pulse-echo data collection. Collected data is then streamlined to a controller PC through Gigabit Ethernet for real-time data processing. The data processing computer can easily handle the intensive computations required by high resolution (both spatial and temporal) speckle tracking and separable 2D post filtering by utilizing a many core GPU (nVIDIA, Santa Clara, Calif.). A linear array probe (LA14-5/38) was used to acquire all data of this example. The center frequency of the transmit pulse on the probe was 7.5 MHz.

Received Signal Model

A received signal model for pulse-echo beamformed ultrasound data obtained from a typical scanner and typical vascular probe such as those described above is provided. The echo data forming one image line is given by $$x_r(t, l) = x_c(t, l) + x_i(t, l) \quad (1)$$

where $x_c(t; l)$ represents the coherent echo component from depth $z=c/t$ in image line $l$ and $x_i(t; l)$ is the incoherent echo component from the same location. At the vessel wall, the coherent component is largely due to specular reflection from the multi-layered vessel and supporting structure. For simplicity, assume a single layer in a homogeneous medium and a narrowband model:

$$x_c(t, l) = R_{tw} p\left(t - \frac{2z_0}{c}\right) + \sum_{k=1}^{\infty} \alpha_k p\left(t - \frac{2z_0}{c} - \frac{2kd_w}{c}\right) \quad (2)$$

where $p(t) = a(t)e^{j(\omega_0 t + \theta(t))}$ is the analytic transmitted ultrasound pulse, $R_{tw}$ is the reflection coefficient, and $d_w$ is the vessel wall thickness. In (2), $R_{tw}$ represents the tissue-wall reflection coefficient and $a_k$ is a function of the wall-tissue reflection and transmission coefficients. The reflection coefficients are typically small (e.g. <10%) and the series in (2) is practically 2 to 4 terms for each layer. Unfortunately, the reverberation terms interfere with the echo components from the blood in the vessel. Despite their rapid decay, their amplitude remains high enough to mask the echoes from the blood in a region that extends several millimeters inside the vessel. A dereverberation filter can be used to unmask the echoes from the blood and allow the two-dimensional speckle tracking to estimate vector velocity inside the vessel.

Inverse Filter Design for Echo Dereverberation

The correlation function of the coherent echo component exhibits secondary peaks at $\tau_k$=2kdw/c. The amplitude of these peaks diminishes exponentially with k (due to multiple reflection within the wall). These secondary peaks can be estimated from the auto correlation function of the echo data after baseband conversion. Results from actual vascular imaging experiments suggest that a Gaussian mixture model (GMM) may be most appropriate for modeling the probability density function (pdf) of the clean echo data. The GMM is also motivated by a number of hypotheses on the scattering by blood (e.g. due to flow or red blood cell aggregation). An infinite impulse response (IIR) model is assumed for the dereverberation inverse filter $$y[n] = x[n] - \sum_{k=1}^{N} a_k y[n-k] \qquad (3)$$

The coefficients, $\{a_k\}_{k=1}^{N}$ can be obtained by maximizing the log-likelihood with respect to the GMMs in the flow channel:

$$\mathcal{L} = \frac{1}{N_y} \sum_{n=n_0}^{n_0+N_y-1} \log\left(\sum_{i=1}^{N_g} \frac{w_i}{\sqrt{2\pi\sigma_i^2}} \exp\left(-\frac{(y[n]-\mu_i)^2}{2\sigma_i^2}\right)\right), \qquad (4)$$

where $N_g$ is the number of Gaussian densities in the GMM (each represented by $\{w_i; \mu_i, \sigma_i\}$) and $N_y$ is the length of output test sequence. The parameters of the IIR inverse filter can be obtained by maximizing $\mathcal{L}$ in (4) by partial derivatives with respect to $\{a_k\}_{k=1}^{N-1}$, $$\frac{\partial \mathcal{L}}{\partial a_k} = \frac{1}{N_y} \sum_{n=n_0}^{n_0+N_y-1} \sum_{i=1}^{N_g} \frac{\mathcal{E}_{i,n}}{\mathcal{E}_n} \frac{(y[n]-\mu_i)y[n-k]}{\sigma_i^2} \qquad (5)$$

where $\mathcal{E}_{i,n}$ and $\mathcal{E}_n$ are the ith term inside the inner summation in (4) and the inner summation, respectively. The parameters of the filter can be obtained iteratively through $$a_k[m+1] = a_k[m] + \delta \frac{\partial \mathcal{L}}{\partial a_k[m]} \qquad (6)$$

where m is the iteration index and d is chosen sufficiently small to allow for fine convergence (at the expense of convergence speed). In at least one embodiment, (5) can be simplified if the GMM is dominated by one distribution, which is often the case. At any rate, an empirical values of δ=0:01 result in convergence within 10 iterations or less.

Model-order Selection: The parameter N in (3) can be determined from the identification of secondary peaks in the autocorrelation function of the complex envelope of the echo data from the proximal vessel wall and from the vessel including the proximal wall. Periodicities in these correlation functions are identifiable with the wall (and supporting-tissue) architecture, which is primarily responsible for reverberation within the vessel. For the carotid artery of an typical human subject, the order varies depending on the phase of the cardiac cycle with a range of 20-45 (lower orders when the vessel wall is maximally stretched). A maximum value, $N_{max}$ on the model order could be set from the observation of the periodicities throughout the heart cycle.

Reverberation-Free Training Data

Obtaining reverberation-free echo data can be accomplished by tilting the imaging transducer to avoid specular reflections from the vessel wall (after identifying the vessel wall). In practice, a very small tilt is sufficient to significantly remove the specular echo and maintain a good view of the vessel. Color flow or power Doppler mode can be used to define the flow region for extracting the training echo data. Once this is achieved, the imaging transducer is returned to a position where the vessel boundaries can be best defined from specular reflections. It is also possible to get reverberation-free data from corrupted views by carefully selecting regions where the reverberation components are not present.

For example, a blood vessel with 6-mm diameter may provide 2 mm region of reverberation-free echo data at its distal end. One can use the latter approach to identify the GMM during a typical heart cycle. Based on actual echo data from a human subject, the value of $N_g$ in (4) is typically 3 to 4, all with zero mean.

Time-Varying Filter Design Algorithm

Based on the above derivation and facts about the data acquisition model for beamformed echo data from typical vascular imaging ultrasound, the following filter design steps are provided. For image line 1 and image frame p, Step 0 Detect the proximal vessel wall from complex envelope data Step 1 Determine the IIR model order, N, from the short range and long-range correlation functions.

Step 2 Determine the GMM parameters from the reverberation free segment of the vessel echo data.

Step 3 Determine the filter coefficients using the maximum likelihood algorithm (Equations 4-6).

Step 4 Apply the IIR filter to vessel data with appropriate initial conditions to avoid breaks in the echo data.

Step 5 Compute long-range correlation function on y[n]. If reverberation still detectable, While $N<N_{max}$ GoTo Step 3. Otherwise Stop.

Results and Discussion Regarding Example:

Data Collection—The Sonix RP was used to collect M2D mode data from imaging the right carotid artery of a healthy volunteer. Real-time beamformed RF data was collected at a frame rate of 325 fps and processed off-line to produce images similar to those shown in FIGS. 16A-16B, which shows lateral (FIG. 16A) and axial displacements (FIG. 16B) of the carotid artery color-coded and overlaid on the B-mode gray scale images. The displacement fields were estimated using the phase coupled two-dimensional speckle tracking algorithm described in Ebbini 2006.

Figure 17A:
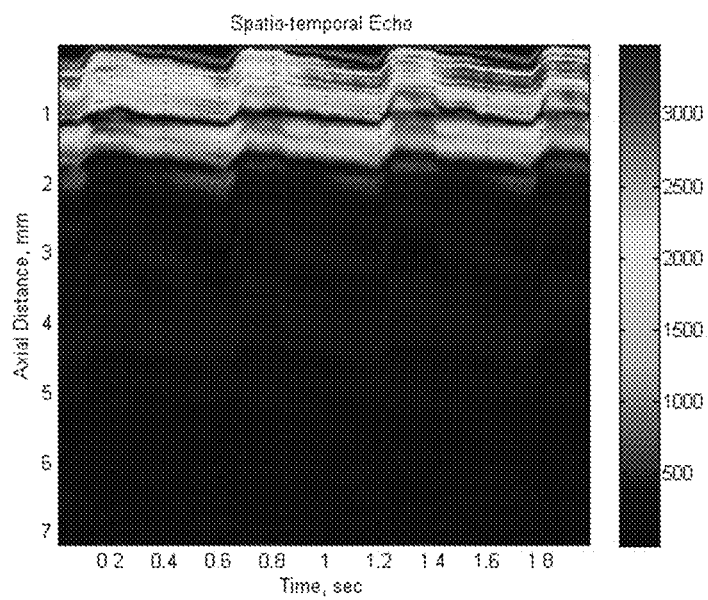
FIGS. 17A-17B show spatio-temporal maps relating to dereverberation filtering examples.

Approximately 1.9 seconds (642 frames) of data was acquired capturing more than three heart cycles to allow for modeling the dynamics of echoes and reverberation from the vessel, primarily due to the proximal wall. Spatio-temporal maps of the echoes from the vessel (proximal wall through the vessel, but excluding the distal wall) are shown in FIG. 17A. The image shows the envelope of the RF data from one image line (approximately at the center of the images). This is referred to as M-mode ultrasound and it allows for the analysis of wall motion in cardiac and vascular imaging application.

Figure 17B:
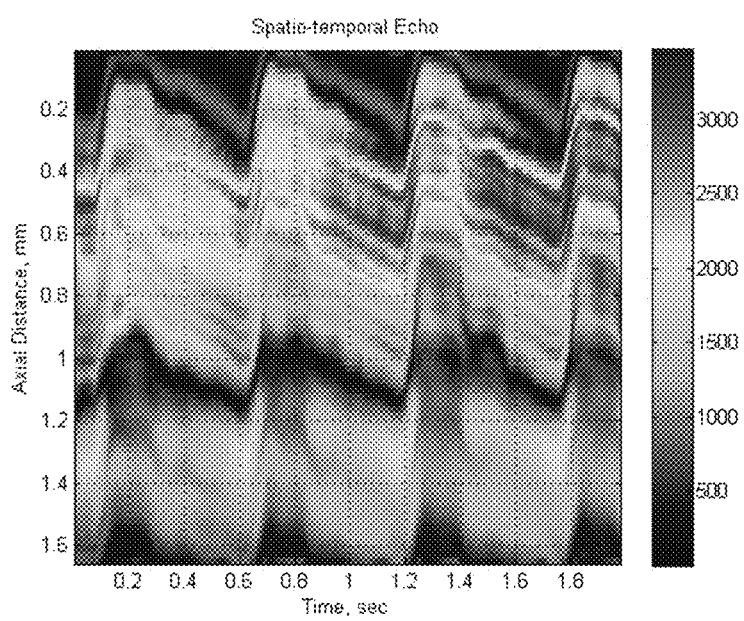

FIG. 17B shows an M-mode image of the echoes from the proximal wall only during the acquisition period. The image illustrates the dynamics of the wall echoes during the heart cycle. For example, for the first few lines (0<t<0:1 s), the wall represents a purely specular reflector. On the other hand, the wall echo appears less organized when the wall undergoes expansion due to pressure changes in the vessel. Examining the envelope in the vessel shown in FIG. 17A, one can see a strong reverberation pattern down to about 4 mm into the vessel. This pattern masks any scattering from the blood and makes it difficult, if not impossible, to estimate the flow velocity vectors in a large region within the vessel.

Figure 18A:
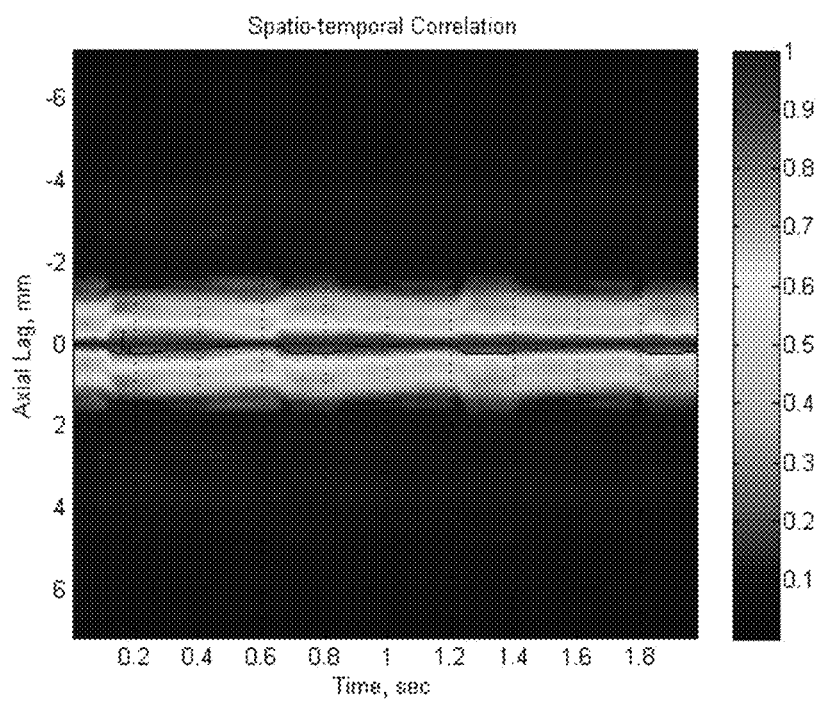
FIGS. 18A-18B show spatio-temporal maps relating to dereverberation filtering examples.
Figure 18B:
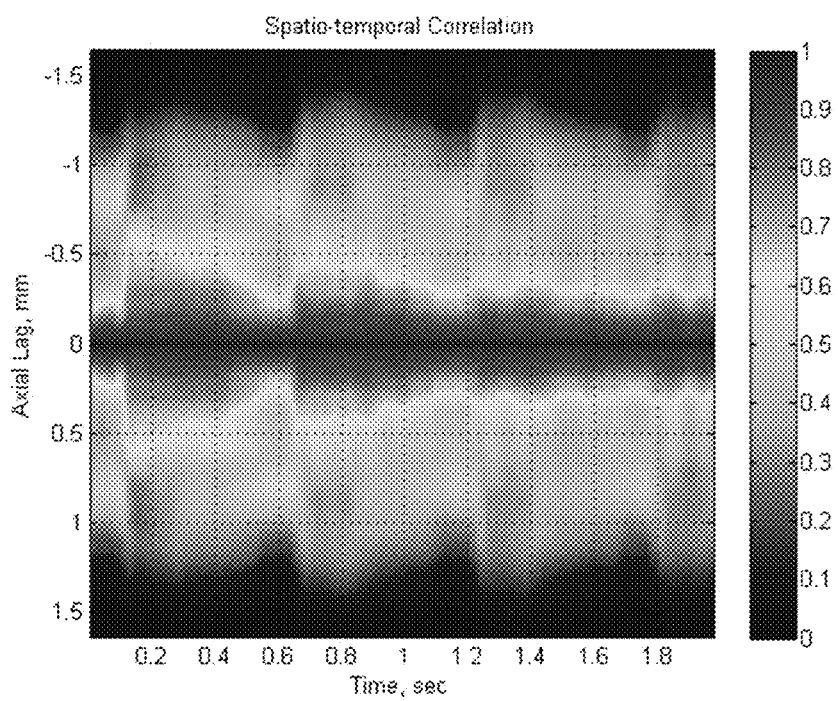

FIGS. 18A-18B show spatio-temporal maps of normalized correlation function of the complex envelope from the vessel including the proximal wall (FIG. 18A—a long range correlation) and proximal wall only (FIG. 18B—a short range correlation) corresponding to the M-mode images shown in FIGS. 17A-17B. One can see the strong secondary peaks ≈∓0:8 mm when the vessel wall is not stretched and behaves as a specular reflector. On the other hand, this peak is diminished and the main lobe of the correlation function is broadened when the vessel wall is stretched. This result demonstrates that a time-varying dereverberation filter will be beneficial.

Figure 19A:
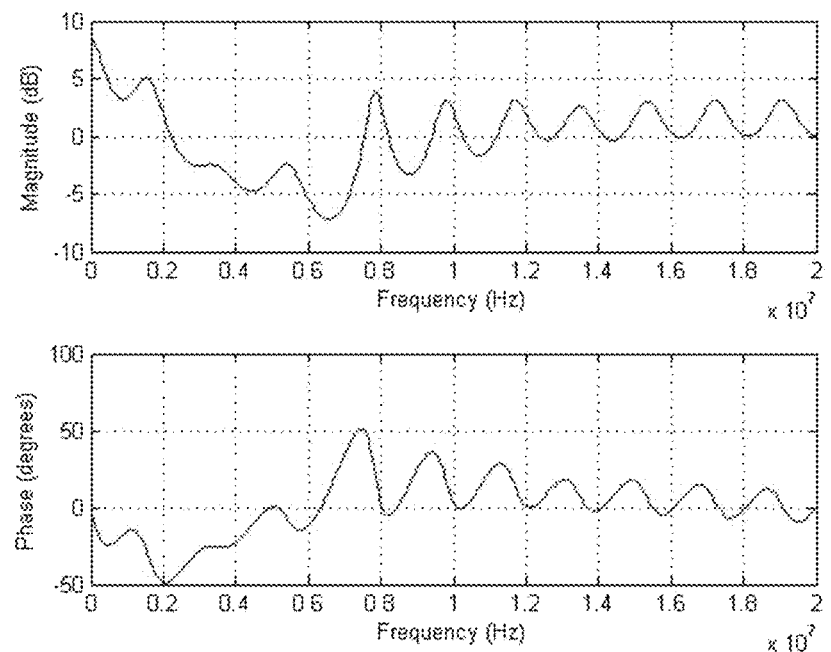
FIGS. 19A-19D show graphs relating to dereverberation filtering results of examples presented herein.
Figure 19B:
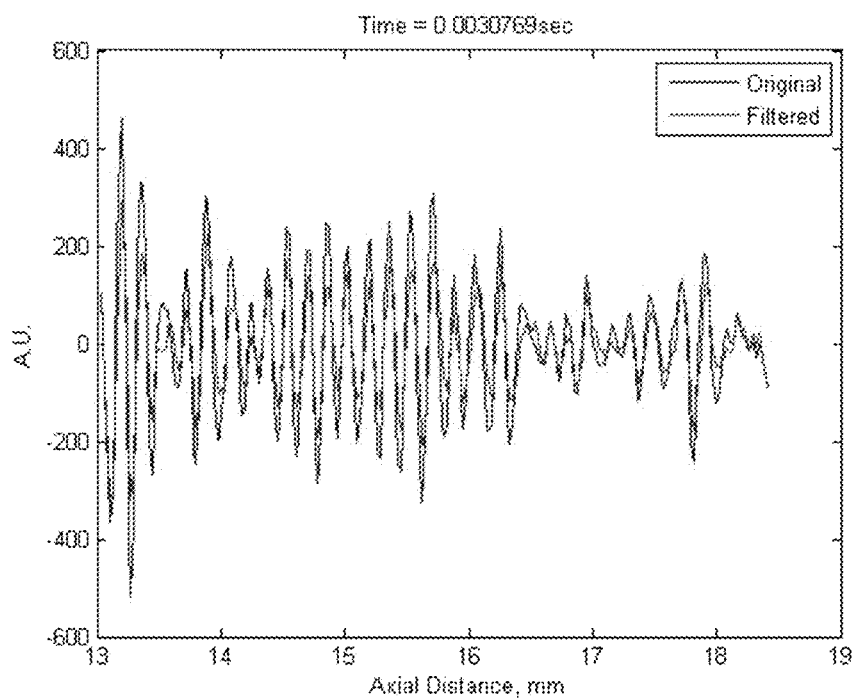
Figure 19C:
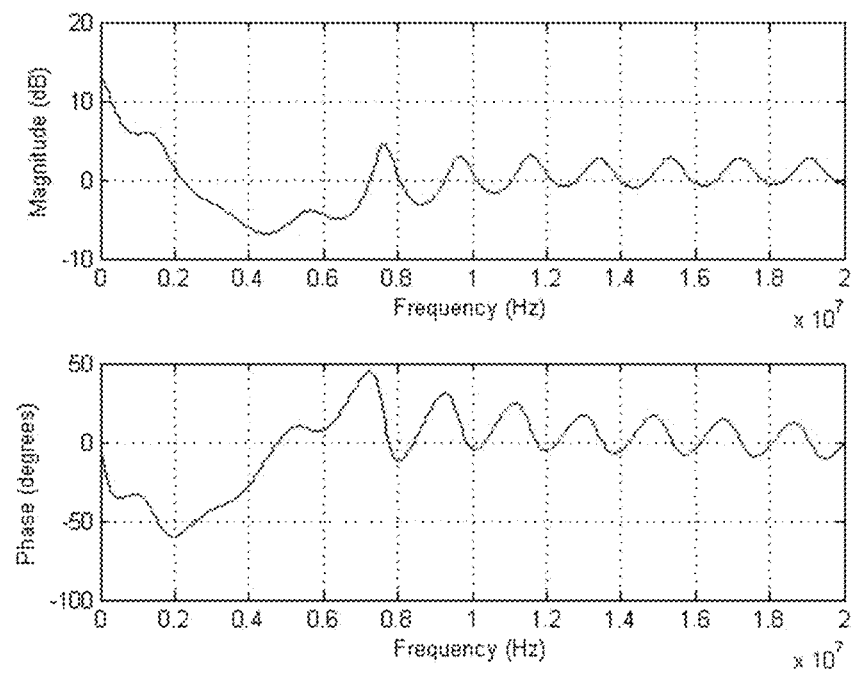
Figure 19D:
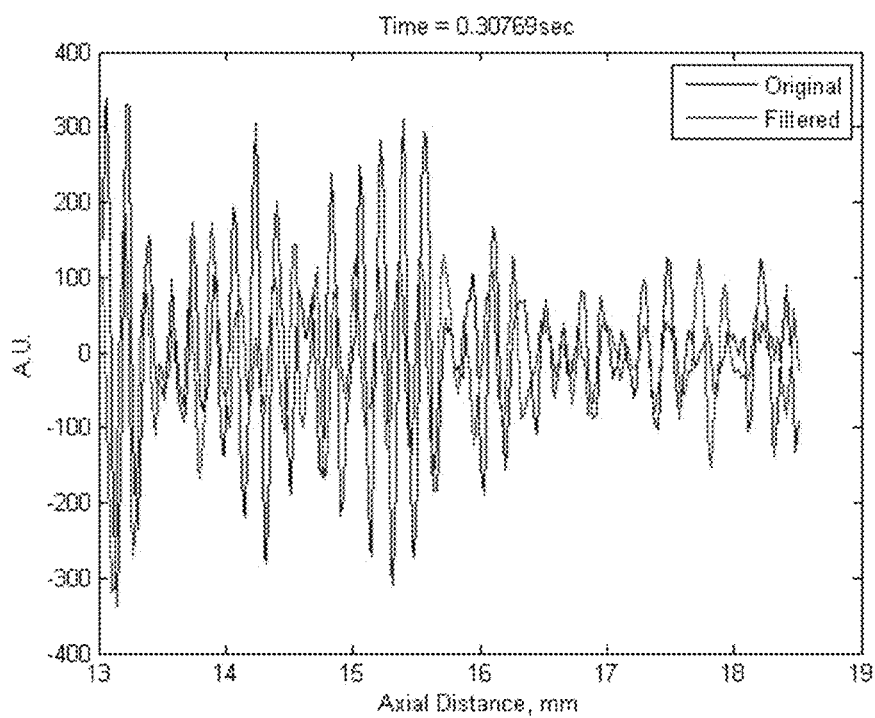

FIGS. 19A-19D illustrate the performance of the dereverberation filters obtained through the proposed maximum likelihood algorithm. Using short-range and long-range correlation data, the filter order was determined to be 21 for two frames (Frame 1 at t=0.003 s and Frame 100 at t=0.31 sec). The GMM models were estimated from the vessel data near the distal wall using $N_g$=3. $N_y$=50 was used in both cases and δ=0:005. Convergence was achieved in 7 and 9 iterations for Frame 1 and Frame 100 data, respectively. The magnitude response of both filters demonstrate inverse filtering and dereverberation characteristics; signal bandwidth 2-6 MHz is inverted and ripple throughout. FIGS. 19A-19D represent the dereverberation filters and vessel data with and without filtering for Filter Frame 1 (FIGS. 19A-19B) and Filter Frame 100 (FIGS. 19C-19D).

Results from vascular imaging experiment from a healthy volunteer demonstrate the feasibility of dereverberation of echo data from blood vessels using time-varying inverse dereverberation filters to account for the time-varying nature of the reverberation components during the heart cycle. Such filtering may for more accurate vector velocity estimation in the vessel using speckle tracking (e.g., two-dimensional speckle tracking) methods. The exemplary algorithm is robust and computationally efficient and requires minimal training making it well-suited for real-time ultrasound imaging applications.

The following provides one or more implementations of vascular imaging and characterization of vessel wall dynamics or examples testing the same, such as generally described herein. Such specific implementations or examples are not to be taken as being limiting to the present disclosure.

Generally, a method for simultaneous imaging of tissue motion and flow with subsample accuracy in both axial and lateral directions is illustrated. The method utilizes a phase-coupled 2D speckle tracking approach, which employs the true 2D complex cross correlation to find sub-pixel displacements in both axial and lateral directions. The imaging sequence on a Sonix RP scanner has been modified to allow high frame rate 2D data collection in a limited field of view covering the region of interest (M2D-mode). Together with the robust 2D speckle tracking method, M2D imaging allows for capturing the full dynamics of the flow and wall/tissue motion, even when the flow is primarily in the lateral direction (with respect to the imaging beam). The fine vector displacement estimates in both axial and lateral directions are shown to allow for smooth and contiguous strain and shear strain calculations with minimal filtering. The quality of the displacement and strain fields is demonstrated by experimental results from a flow phantom (ATS Model 524) and in vivo images of the carotid artery in a healthy volunteer. The results demonstrate simultaneous imaging of the vector flow field and the wall/tissue motion and the corresponding strains at high spatial and temporal sampling. This may provide an essential tool in modeling the fluid-solid interactions between the blood and blood vessel.

Materials and Methods for an Exemplary Imaging Method

Phase-Coupled 2D Speckle Tracking—The phase-coupled 2D speckle tracking algorithm used is described in Ebbini 2006 and also at least partially described herein. The speckle tracking method is based on the gradients of the magnitude and phase of 2D complex correlation in a search region. This approach couples the phase and magnitude gradients near the correlation peak to determine its coordinates with subsample accuracy in both axial and lateral directions. This is achieved with a minimum level of lateral interpolation determined from the angles between the magnitude and phase gradient vectors on the sampled (laterally interpolated) 2D cross-correlation grid. One result behind this algorithm is that the magnitude gradient vectors' final approach to the true peak is orthogonal to the zero-phase contour. This leads to a 2D robust projection on the zero-phase contour that results in subsample accuracy at interpolation levels well below those needed using previously proposed methods. It is shown that estimated 2D vector displacement fields obtained using the phase-coupled technique display a full range of values covering the dynamic range without evidence of quantization. In comparison, a previously published method using 1D phase-projection after lateral interpolation produces severely quantized lateral displacement fields (at the same levels of interpolation as the 2D, phase-coupled method).

Data Acquisition—A Sonix RP (Ultrasonix, Canada) ultrasound scanner loaded with a program used for high frame-rate M2D pulse-echo data collection is used. Collected data is then streamlined to a controller PC through Gigabit Ethernet for real-time data processing. The data processing computer can easily handle the intensive computations required by high resolution (both spatial and temporal) speckle tracking and separable 2D post filtering by utilizing a many core GPU (nVIDIA, Santa Clara, Calif.). A linear array probe (LA14-5/38) was used to acquire all data shown in this paper. The center frequency of the transmit pulse on the probe was 7.5 MHz.

Experiments using the ATS Model 524 flow phantom and a Cole-Parmer MasterFlex roller pump were conducted to illustrate the displacement tracking in axial and lateral directions. M2D data was collected using the Sonix RP scanner at a frame rate of 111 fps. Images of a 4-mm flow channel in the ATS phantom were collected under controlled fluid flow with an appropriate speed setting of the Master-Flex pump to mimic typical blood flow rates (e.g. 336 ml/min) in carotid arteries. Cellulose microspheres were diluted in water to produce linear scattering from the flow channel during data collection (pure water was also imaged as a control to determine the channel boundaries as a ground truth).

Strain Computation—Strain and shear strain calculations were performed using MATLAB's gradient command on the axial and lateral displacement fields obtained using the 2D speckle tracking algorithm. The strain and shear strain computations are followed by a simple Gaussian lowpass filter with size of 3×3 and standard deviation of 1, i.e. minimal post filtering of the strain and shear strain fields.

Results and Discussion Regarding the Exemplary Imaging Method

Experimental Phantom Result

Figure 8A:
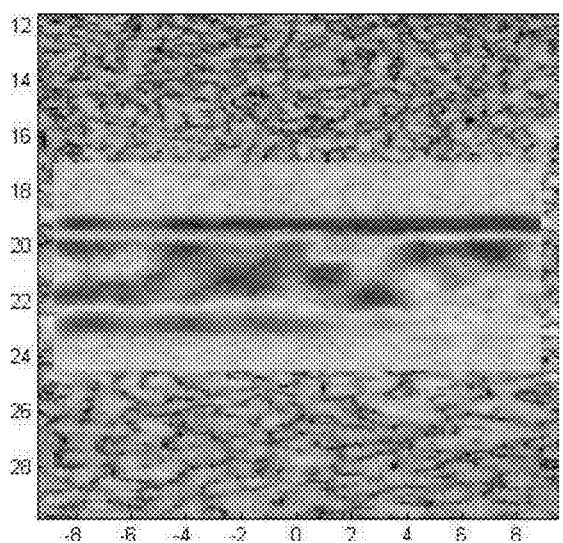
FIGS. 8A-8B show axial stain and axial shear strain images of flow channel walls relating to examples carried out and described at least in part herein.
Figure 8B:
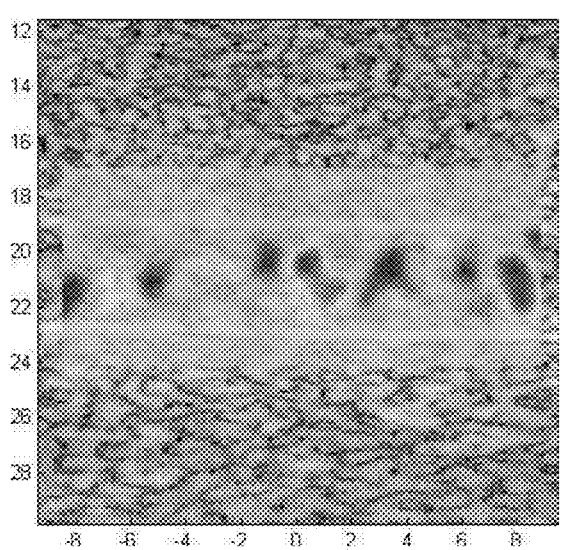
Figure 9A:
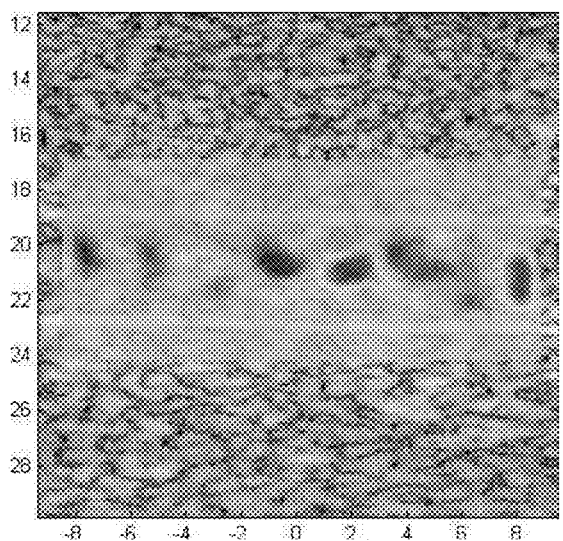
FIGS. 9A-9B show lateral stain and lateral shear strain images of flow channel walls relating to examples carried out and described at least in part herein.
Figure 9B:
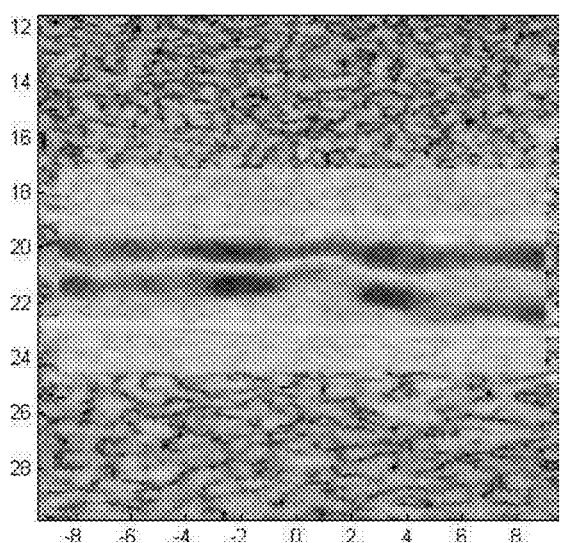

The 4-mm flow channel was imaged using the LA14-5 probe with the channel axis perpendicular to the beam axis, i.e. lateral flow. Typical examples of the resulting strain and shear strain fields are shown in FIGS. 8A-8B and FIGS. 9A-9B. FIGS. 8A-8B show axial strain and axial shear strain of the 4-mm flow channel longitudinal walls, respectively. FIGS. 9A-9B show lateral strain and lateral shear strain of the 4-mm flow channel longitudinal walls, respectively. One can see the smoothness of the strain fields which demonstrates the well-behaved nature of the displacement fields. At the same time, one can appreciate the clear demarcation between the channel and the surrounding tissue-mimicking material.

Figure 10:
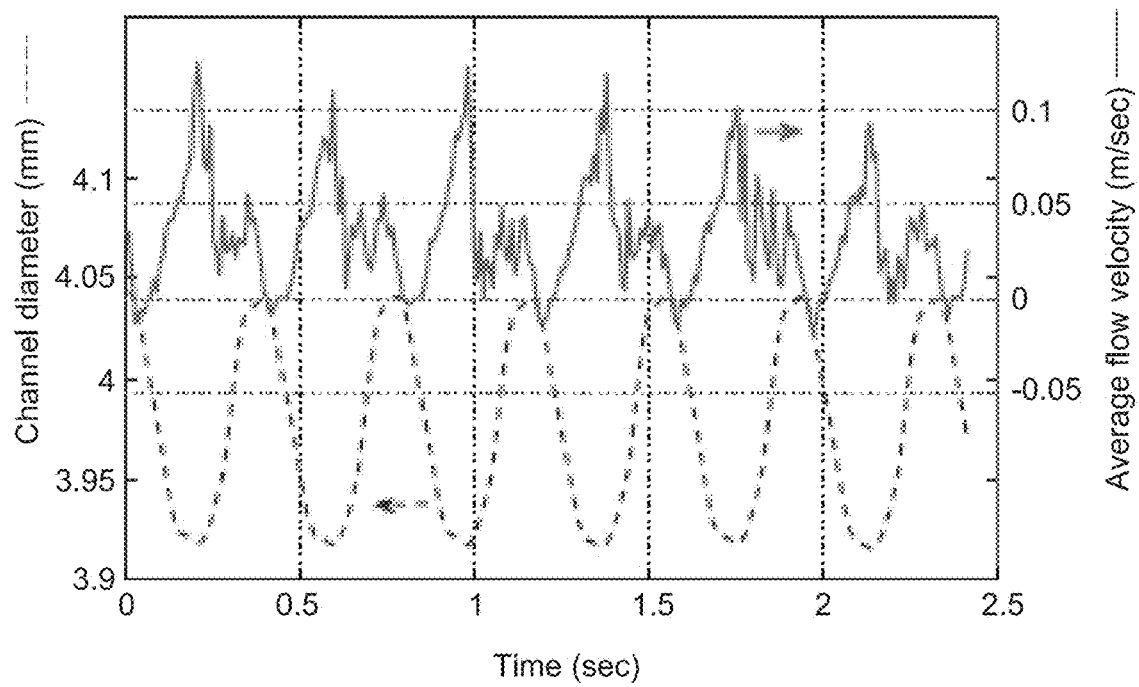
FIG. 10 shows a graph of channel diameter computed from tracked channel wall displacements over time and average flow velocity obtained from tracked fluid displacements over time within a flow channel relating to an example carried out and described at least in part herein.

The dynamics of the estimated vector flow field are illustrated by the result in FIG. 10 which shows a plot of the periodic channel diameter (obtained from the axial component at the channel walls computed from the tracked channel wall displacement) and the corresponding average lateral flow velocity in the channel for several cycles of pump operation (i.e., within the 4 mm flow channel in the ATS phantom). The result shows clearly the quasi-periodic nature of the observed flow velocity and the phase relationship between the diameter (pressure in the channel) and flow. Note that the small negative component in the flow velocity occurs right after the diameter reaches its maximum value (i.e. minimum pressure in the channel). This "back up" of the fluid in the channel was easily observed in B-mode movies, but the wall motion was much more subtle (<150 mm) and was only seen in the axial displacement field.

Figure 11:
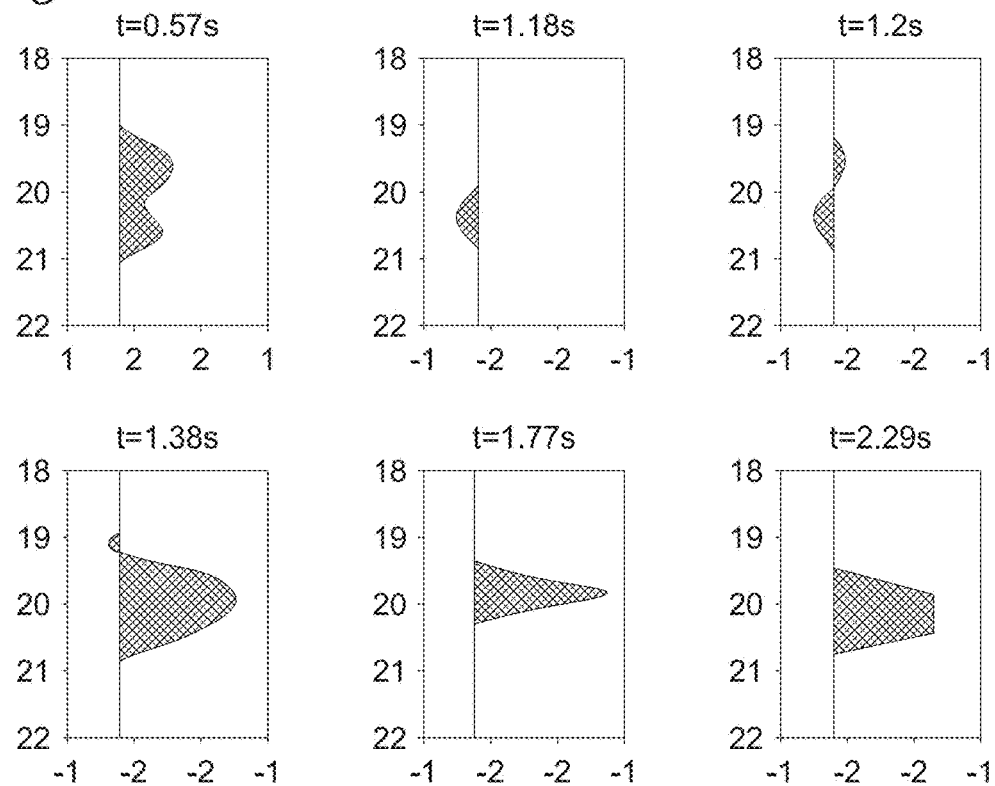
FIG. 11 shows graphs of total displacement vector waveforms with a channel at different time instances relating to an example carried out and described at least in part herein.

The dynamic behavior of the lateral flow along the axis of the imaging beam (at a lateral distance of −3.2 mm) is illustrated by FIG. 11. One can see the smooth, well-behaved nature of the lateral displacement fields consistent with the quasi-periodic pattern shown in FIG. 10. It is noted that the results shown in FIG. 11 are minimally processed, i.e., the continuity and the high SNR of the vector displacement estimation in the fluid and the surrounding tissue is a direct consequence of the proper application of the phase-coupled 2D speckle tracking method.

In Vivo Experiment

Figure 12A:
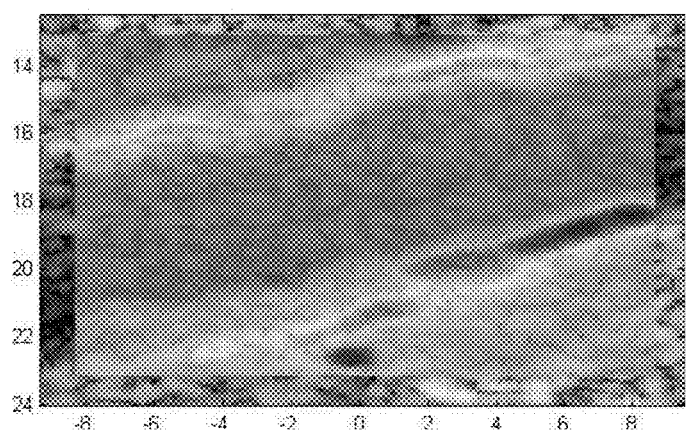
FIGS. 12A-12B show axial stain and axial shear strain images of carotid artery longitudinal vessel walls relating to examples carried out and described at least in part herein.
Figure 12B:
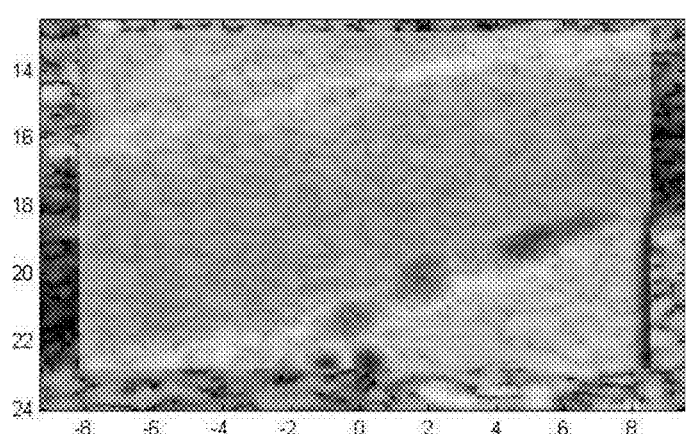
Figure 13A:
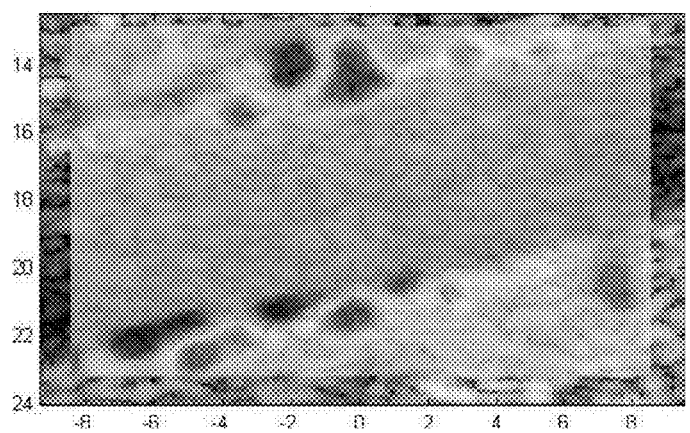
FIGS. 13A-13B show lateral stain and lateral shear strain images of carotid artery longitudinal vessel walls relating to examples carried out and described at least in part herein.
Figure 13B:
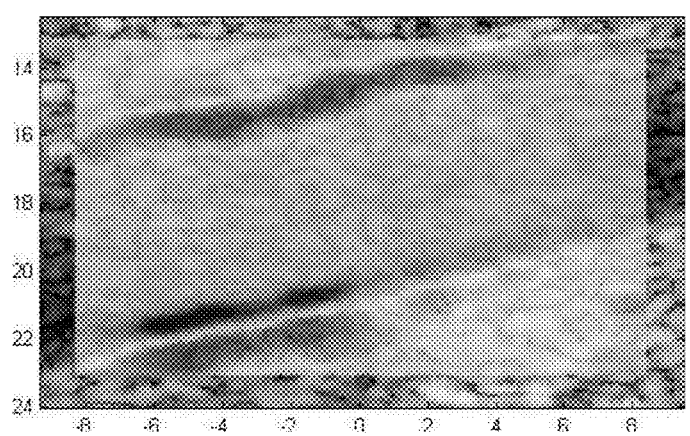

A segment of the carotid artery of a healthy volunteer was imaged using the LA14-5 probe at 111 fps. As in the phantom case, the axial and lateral displacement fields were contiguous throughout the region of interest and allowed for the computation of the strain and shear strain fields shown in FIGS. 12A-12B and FIGS. 13A-13B. FIGS. 12A-12B show axial strain and axial shear strain of the carotid artery longitudinal vessel walls, respectively. FIGS. 13A-13B show lateral strain and lateral shear strain of the carotid artery longitudinal vessel walls, respectively. One can see the clear demarcation between the vessel and the wall/perivascular tissue in the axial strain and lateral shear strain images. Also, the pulsation effect can be appreciated from the axial shear strain and lateral strain images. These results demonstrate reliable estimation of the vector motion fields (axial and lateral) and their utility in obtaining realistic strain and shear strain fields.

Figure 14A:
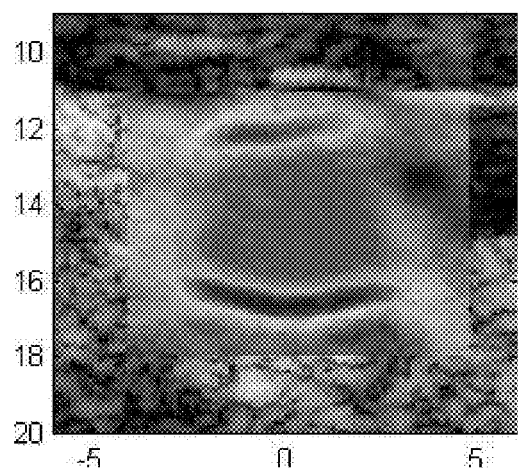
FIGS. 14A-14B show axial stain and axial shear strain images of carotid artery cross-sectional vessel walls relating to examples carried out and described at least in part herein.
Figure 14B:
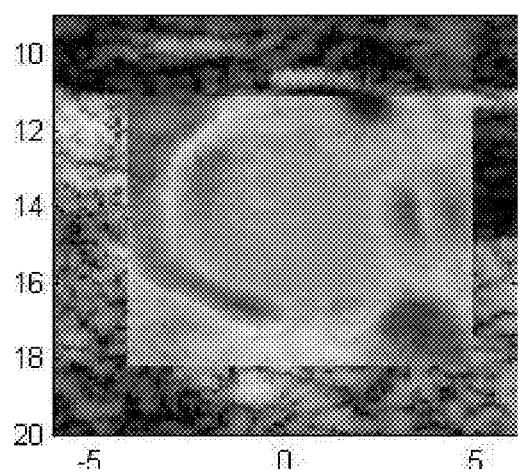
Figure 15A:
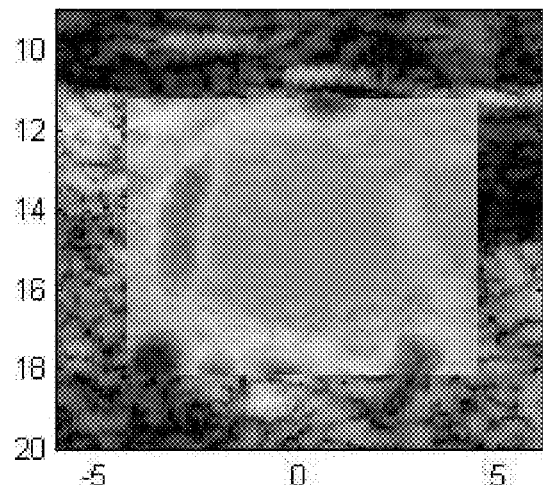
FIGS. 15A-15B show lateral stain and lateral shear strain images of carotid artery cross-sectional vessel walls relating to examples carried out and described at least in part herein.
Figure 15B:
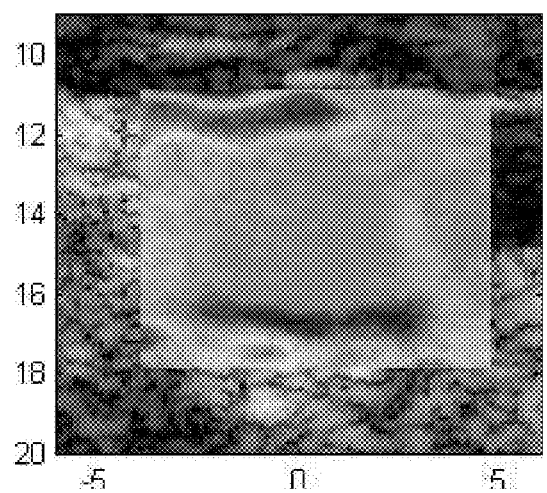
Figure 16A:
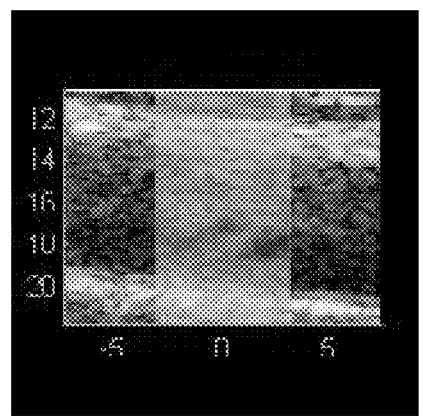
FIGS. 16A-16B show lateral and axial displacements relating to dereverberation filtering examples.
Figure 16B:
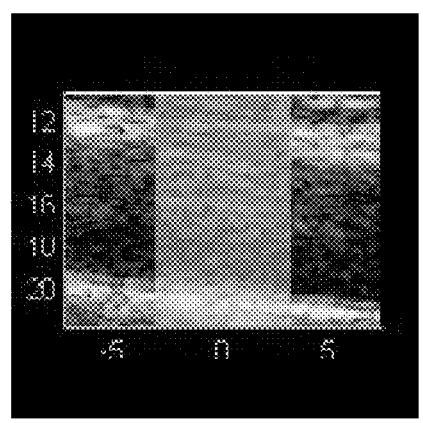

Finally, we show a cross sectional view of the strain fields around the carotid artery of a healthy volunteer. The strains and shear strains in both axial and lateral directions are shown in FIGS. 14A-14B and FIGS. 15A-15B, respectively. FIGS. 14A-14B show axial strain and axial shear strain of the carotid artery cross-sectional vessel walls, respectively. FIGS. 15A-15B show lateral strain and lateral shear strain of the carotid artery cross-sectional vessel walls, respectively Examining FIGS. 14A-14B one can observe that the motion in the axial direction produced a strain in the axial direction at the wall (FIG. 14A) and a shear component to the lateral direction (FIG. 14B). The direction of the strains in this case depicts an expanding vessel. Similarly, the motion in the lateral direction produced a strain in the lateral direction (FIG. 15A) and a shear component to the axial direction as in (FIG. 15B). Movies of the strain and shear strain fields have showed the dynamics of wall movement clearly (such not presentable in this application). In addition to the wall dynamics, the strain images provide a tool for identifying the boundaries of the vessel in both axial and lateral directions. The latter is generally difficult to determine from B-mode images.

As a result of the example, a method for imaging the displacement and strain fields in the vicinity of flow channels has been demonstrated experimentally in a flow phantom and in vivo imaging of the carotid artery of healthy volunteer. The results show that, at sufficiently high frame rates, speckle tracking methods produce well-behaved displacement estimates of both the tissue motion and flow in the channel. These displacement fields are well suited for strain and shear strain calculations with minimum filtering. Further, it has been demonstrated that time waveforms of flow velocity and pressure to follow the periodic motion of the roller pump in the phantom experiments. Furthermore, the axial wall displacements (indicative of pressure) and average lateral flow velocity in the channel have a clear phase relationship. This indicates that the method used may be useful in obtaining the full dynamic motion fields suitable for use in solid-fluid interface modeling of vascular mechanics.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. An imaging method comprising:
   providing ultrasound pulse-echo data of a region in which at least one portion of a blood vessel is located, wherein the pulse-echo data comprises pulse-echo data at a frame rate such that measured displacement of the vessel wall defining the at least one portion of the blood vessel and measured average blood flow through the at least one portion of the blood vessel have a quasi-periodic profile over time to allow motion tracking of both the vessel wall and the blood flow simultaneously;
   generating strain and shear strain image data for the region in which the at least one portion of the blood vessel is located using speckle tracking, wherein the speckle tracking comprises using multi-dimensional correlation of pulse-echo data of one or more speckle regions undergoing deformation in the region in which the at least one portion of the blood vessel is located, wherein the multi-dimensional correlation comprises performing a cross-correlation on the pulse-echo data and determining a cross-correlation peak for the pulse-echo data based on phase and magnitude gradients of the cross-correlated pulse-echo data; and identifying at least one vascular characteristic of the region in which the at least one portion of the blood vessel is located based on the strain and shear strain image data, wherein the at least one vascular characteristic comprises at least one of a flow characteristic associated with flow through the blood vessel, a structural characteristic associated with the blood vessel, and a hemodynamic characteristic associated with the blood vessel.

2. The method of claim 1, wherein identifying at least one vascular characteristic comprises at least one of identifying one or more vessel wall boundaries of the vessel wall, identifying the one or more vessel wall boundaries of the vessel wall and measuring tissue property within the one or more vessel wall boundaries, and calculating one or more hemodynamic measurements based on both the motion tracking motion of the vessel wall and the blood flow simultaneously.

3. The method of claim 2, wherein identifying the one or more vessel wall boundaries of the vessel wall comprises identifying vessel wall boundaries around the entire blood vessel in the region.

4. The method of claim 2, wherein identifying at least one vascular characteristic comprises identifying one or more portions of a plaque architecture adjacent the one or more vessel wall boundaries.

5. The method of claim 1, wherein the speckle tracking further comprises modifying a characteristic of at least one speckle region of the one or more speckle regions being tracked based on the one or more vessel wall boundaries of the vessel wall identified such that the at least one speckle region is entirely within or outside of the vessel wall.

6. The method of claim 1, wherein using multi-dimensional correlation of pulse-echo data of the one or more speckle regions comprises using two-dimensional correlation of pulse-echo data of the one or more speckle regions.

7. The method of claim 1, wherein determining the cross-correlation peak comprises:
coarsely searching the magnitude of the pulse-echo data in a lateral and axial direction to locate a vicinity of the cross-correlation peak within the cross-correlated pulse-echo data;
determining, within a vicinity of the cross-correlation peak, at least two opposing gradient vectors in proximity to the cross-correlation peak;
determining, within the vicinity of the cross-correlation peak, a zero-phase line of the cross-correlated pulse-echo data; and
using the at least two opposing gradient vectors in proximity to the cross-correlation peak and the zero-phase line to estimate the cross-correlation peak.

8. The method of claim 1, wherein the method further comprises delivering therapy to a patient based on the identification of the at least one vascular characteristic of the region in which the at least one portion of the blood vessel is located.

9. The method of claim 1, wherein the method further comprises using ultrasonic energy to deliver therapy based on the identification of the at least one vascular characteristic of the region in which the at least one portion of the blood vessel is located.

10. The method of claim 9, wherein the method further comprises providing at least one transducer configured to transmit and receive ultrasonic energy, wherein using ultrasonic energy to deliver therapy based on the identification of the at least one vascular characteristic of the region in which the at least one portion of the blood vessel is located comprises using the at least one transducer to obtain the pulse-echo data and to generate the ultrasonic energy to deliver therapy.

11. The method of claim 1, wherein generating strain and shear strain image data for the region in which the at least one portion of the blood vessel is located using two-dimensional speckle tracking comprises generating at least one of axial strain and axial shear strain image data and/or lateral strain and lateral shear strain image data.

12. The method of claim 1, wherein providing the ultrasound pulse-echo data of the region in which the at least one portion of the blood vessel is located comprises using coded excitation.

13. The method of claim 1, wherein the method further comprises applying a dereverberation filter to the pulse-echo data from the one or more speckle regions in the blood to remove echo components in the pulse-echo data due to reflection at the vessel wall when performing the speckle tracking of the pulse-echo data from the one or more speckle regions in the blood.

14. The method of claim 1, comprising simultaneously measuring the displacement of the vessel wall and the average blood flow through the at least one portion of the blood vessel based on the strain and shear strain image data.

15. An imaging method comprising:
providing ultrasound pulse-echo data of a region in which at least one portion of a blood vessel is located;
using speckle tracking of one or more speckle regions of the region in which at least one portion of the blood vessel is located to track motion of both the vessel wall defining the at least one portion of the blood vessel and blood flow through the at least one portion of the blood vessel, wherein providing the pulse-echo data comprises providing the ultrasound pulse-echo data at a frame rate such that displacement of the vessel wall defining the at least one portion of the blood vessel and the blood flow through the at least one portion of the blood vessel are measurable simultaneously within a same periodic cycle corresponding to a cardiac pulse cycle;
measuring average blood flow; and
identifying at least one vascular characteristic of the region in which the at least one portion of the blood vessel is located based on the simultaneously measured displacement of the vessel wall and the average blood flow.

16. The method of claim 15, wherein the method further comprises generating strain and shear strain image data for the region in which the at least one portion of the blood vessel is located using the speckle tracking, wherein the speckle tracking comprises using multi-dimensional correlation of sampled pulse-echo data of the one or more speckle regions undergoing deformation in the region in which the at least one portion of the blood vessel is located, wherein the multi-dimensional correlation comprises performing a cross-correlation on the sampled pulse-echo data and determining a cross-correlation peak for the sampled pulse-echo data based on phase and magnitude gradients of the cross-correlated sampled pulse-echo data.

17. The method of claim 15, wherein identifying at least one vascular characteristic comprises at least one of identifying one or more vessel wall boundaries, measuring tissue property within the one or more vessel wall boundaries, and calculating one or more hemodynamic measurements based on both tracking the motion of the vessel wall and the blood flow simultaneously.

18. The method of claim 15, wherein the method further comprises delivering therapy to a patient based on the identification of the at least one vascular characteristic of the region in which the at least one portion of the blood vessel is located.

19. An imaging method comprising:
providing ultrasound pulse-echo data of a region in which at least one portion of a blood vessel is located;
using speckle tracking of one or more speckle regions of the region in which the at least one portion of the blood vessel is located to track motion of at least one of the vessel wall defining the at least one portion of the blood vessel and blood flow through the at least one portion of the blood vessel;
identifying one or more vessel wall boundaries of the vessel wall based on the speckle tracking of the one or more speckle regions; and
modifying at least one characteristic of at least one speckle region of the one or more speckle regions being tracked based on the one or more vessel wall boundaries identified such that the at least one speckle region is entirely within or outside of the vessel wall.

20. The method of claim 19, modifying at least one characteristic of at least one of the one or more speckle regions being tracked comprises modifying at least one of location, size, or shape based on the one or more vessel wall boundaries identified such that the at least one speckle region is entirely within or outside of the vessel wall.

21. The method of claim 19, wherein identifying the one or more vessel wall boundaries comprises identifying vessel wall boundaries around the entire blood vessel in the region.

22. An imaging method comprising:
providing ultrasound pulse-echo data of a region in which at least one portion of a blood vessel is located;
using speckle tracking of one or more speckle regions of the region in which at least one portion of the blood vessel is located to track motion of at least blood flow through the at least one portion of the blood vessel; and
removing echo components in the pulse-echo data due to reflection at a vessel wall defining the at least one portion of the blood vessel when performing the speckle tracking of the pulse-echo data from the one or more speckle regions in the blood in the at least one portion of the blood vessel
wherein removing echo components in the pulse-echo data due to reflection at the vessel wall comprises using a time-varying inverse filter to reduce the components in the pulse-echo data due to reflection at the vessel wall.

23. The method of claim 22, wherein using the speckle tracking comprises using speckle tracking of the one or more speckle regions of the region in which the at least one portion of the blood vessel is located to track motion of both the vessel wall defining the at least one portion of the blood vessel and the blood flow through the at least one portion of the blood vessel.

24. The method of claim 22, wherein the method further comprises generating strain and shear strain image data for the region in which the at least one portion of the blood vessel is located using the speckle tracking, wherein the speckle tracking comprises using multi-dimensional correlation of sampled pulse-echo data of the one or more speckle regions undergoing deformation in the region in which the at least one portion of the blood vessel is located, wherein the multi-dimensional correlation comprises performing a cross-correlation on the sampled pulse-echo data and determining a cross-correlation peak for the sampled pulse-echo data based on phase and magnitude gradients of the cross-correlated sampled pulse-echo data.

* * * * *